US006383814B1

(12) United States Patent
Lee et al.

(10) Patent No.: US 6,383,814 B1
(45) Date of Patent: *May 7, 2002

(54) CATIONIC AMPHIPHILES FOR INTRACELLULAR DELIVERY OF THERAPEUTIC MOLECULES

(75) Inventors: Edward R. Lee, Natick; David J. Harris, Lexington; Craig S. Siegel, Woburn; Mathieu B. Lane, Cambridge; Shirley C. Hubbard, Belmont; Seng H. Cheng, Wellesley; Simon J. Eastman, Marlborough; John Marshall, Milford; Ronald K Scheule, Hopkinton; Nelson S. Yew, West Upton, all of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/228,232

(22) Filed: Jan. 11, 1999

Related U.S. Application Data

(63) Continuation of application No. 08/668,676, filed on Jun. 25, 1996, now abandoned, which is a continuation of application No. 08/564,087, filed on Oct. 20, 1995, now Pat. No. 5,840,710, which is a continuation-in-part of application No. 08/540,867, filed on Oct. 11, 1995, now Pat. No. 5,747,471, which is a continuation-in-part of application No. 08/352,479, filed on Dec. 9, 1994, now Pat. No. 5,650,096.
(60) Provisional application No. 60/004,399, filed on Sep. 27, 1995, and provisional application No. 60/004,344, filed on Sep. 26, 1995.

(51) Int. Cl.⁷ ........................ C12N 15/88; A61K 48/00; A61K 9/127
(52) U.S. Cl. .................... 435/458; 435/320.1; 424/450; 514/44
(58) Field of Search .............................. 435/320.1, 325, 435/455, 459; 424/450; 514/44

(56) References Cited

U.S. PATENT DOCUMENTS

| | | | |
|---|---|---|---|
| 4,394,448 A | 7/1983 | Szoka et al. | 435/455 |
| 4,544,545 A | 10/1985 | Ryan et al. | 424/1.1 |
| 4,897,355 A | 1/1990 | Eppstein et al. | 435/325 |
| 4,958,013 A | 9/1990 | Letsinger et al. | 536/27 |
| 4,971,803 A | 11/1990 | Li et al. | 424/450 |
| 5,004,737 A | 4/1991 | Kim et al. | 514/182 |
| 5,043,164 A | 8/1991 | Huang et al. | 424/423 |

(List continued on next page.)

FOREIGN PATENT DOCUMENTS

| | | |
|---|---|---|
| EP | 0446017 A1 | 9/1991 |
| EP | 0490379 A3 | 6/1992 |
| JP | 61-7292 | 1/1986 |
| WO | WO 88/00824 | 2/1988 |
| WO | WO 91/16024 | 1/1991 |
| WO | WO 93/24640 | 1/1993 |
| WO | WO 93/05162 | 3/1993 |
| WO | WO 94/05624 | 3/1994 |
| WO | WO 94/20520 | 9/1994 |
| WO | WO 94/21115 | 9/1994 |
| WO | WO 95/02698 | 1/1995 |
| WO | WO 95/14380 | 6/1995 |
| WO | WO 95/14381 | 6/1995 |
| WO | WO 95/14651 | 6/1995 |
| WO | WO 95/17378 | 6/1995 |
| WO | WO 95/21812 | 8/1995 |
| WO | WO 95/24222 | 9/1995 |
| WO | WO 95/31557 | 11/1995 |
| WO | WO 95/32299 | 11/1995 |
| WO | WO 96/03977 | 2/1996 |
| WO | WO 96/10038 | 4/1996 |
| WO | WO 96/17823 | 6/1996 |
| WO | WO 96/18372 | 6/1996 |
| WO | WO 96/20208 | 7/1996 |
| WO | WO 96/25508 | 8/1996 |
| WO | WO 96/32102 | 10/1996 |
| WO | WO 97/29118 | 8/1997 |
| WO | WO 97/31934 | 9/1997 |
| WO | WO 97/45442 | 12/1997 |

OTHER PUBLICATIONS

Zalipsky et al., FEBS Letters 353, 71–74, 1994.*
Papahadjopoulos et al., PNAS, vol. 88, pp. 11460–11464, 1991.*
Blume et al, Biochimica et Biophysica Acta, 1029, 91–97, 1990.*
Klibanov e al., FEBS, vol. 268, 1, 235–237, 1990.*

(List continued on next page.)

Primary Examiner—Dave Trong Nguyen
(74) Attorney, Agent, or Firm—Finnegan, Henderson, Farabow, Garrett and Dunner, LLP

(57) ABSTRACT

Novel cationic amphiphiles are provided that facilitate transport of biologically active (therapeutic) molecules into cells. The amphiphiles contain lipophilic groups derived from steroids, from mono or dialkylamines, or from alkyl or acyl groups; and cationic groups, protonatable at physiological pH, derived from amines, alkylamines or polyalkylamines. There are provided also therapeutic compositions prepared typically by contacting a dispersion of one or more cationic amphiphiles with the therapeutic molecules. Therapeutic molecules that can be delivered into cells according to the practice of the invention include DNA, RNA, and polypeptides. Representative uses of the therapeutic compositions of the invention include providing gene therapy, and delivery of antisense polynucleotides or biologically active polypeptides to cells. With respect to therapeutic compositions for gene therapy, the DNA is provided typically in the form of a plasmid for complexing with the cationic amphiphile.

Novel and highly effective plasmid constructs are also disclosed, including those that are particularly effective at providing gene therapy for clinical conditions complicated by inflammation. Additionally, targeting of organs for gene therapy by intravenous administration of therapeutic compositions is described.

16 Claims, 23 Drawing Sheets

U.S. PATENT DOCUMENTS

| | | | |
|---|---|---|---|
| 5,171,678 A | 12/1992 | Behr et al. | 435/455 |
| 5,240,842 A * | 8/1993 | Mets | 435/455 |
| 5,264,618 A | 11/1993 | Felgner et al. | 560/224 |
| 5,283,185 A | 2/1994 | Epand et al. | 435/455 |
| 5,334,761 A | 8/1994 | Gebeyehu et al. | 564/197 |
| 5,356,633 A * | 10/1994 | Woodle | 424/450 |
| 5,416,203 A | 5/1995 | Letsinger et al. | 536/25.34 |
| 5,496,731 A | 3/1996 | Xu et al. | 424/302.1 |
| 5,585,362 A * | 12/1996 | Wilson et al. | 514/44 |
| 5,614,503 A | 3/1997 | Chaudhary et al. | 514/44 |
| 5,641,662 A * | 6/1997 | Debs et al. | 435/455 |
| 5,643,599 A * | 7/1997 | Lee et al. | 424/450 |
| 5,676,954 A | 10/1997 | Brigham | 424/450 |
| 5,703,055 A | 12/1997 | Felgner et al. | 514/44 |
| 5,756,353 A * | 5/1998 | Debs | 435/375 |
| 5,789,244 A | 8/1998 | Heidrum et al. | 424/93.21 |
| 5,795,587 A | 8/1998 | Gao et al. | 424/450 |
| 5,820,873 A * | 10/1998 | Choi et al. | 424/283.1 |
| 5,853,752 A * | 12/1998 | Unger et al. | 424/450 |
| 5,869,040 A | 2/1999 | Oin | 424/93.21 |
| 5,885,613 A * | 3/1999 | Holland et al. | 424/450 |
| 5,965,542 A * | 10/1999 | Wasan et al. | 514/44 |
| 5,989,540 A * | 11/1999 | Carter | 424/93.2 |
| 6,001,644 A * | 12/1999 | Debs et al. | 435/320.1 |

OTHER PUBLICATIONS

J. Harms et al., "Interferon-y Inhibits Transgene Expression Driven by SV40 or CMV Promoters but Augments Expression Driven by the Mammalian MHC I Promoter," *Human Gene Therapy*, 6 (1995), pp. 1291–1297.

C. Kunsch et al., "NF-κB Subunit–Specific Regulation of the Interleukin–8 Promoter," *Molecular and Cellular Biology*, 13 (1993), pp. 6137–6146.

T. Libermann et al., "Activation of the Interleukin–6 Gene Expression through the NF-κB Transcription Factor," *Molecular and Cellular Biology*, 10 (1990), pp. 2327–2334.

N. Mukaida et al., "Cooperative Interaction of Nuclear Factor-κB- and Cis—Regulatory Enhancer Binding Protein–like Factor Binding Elements in Activating the Interleukin–8 Gene by Pro–inflammatory Cytokines," *The Journal of Biological Chemistry*, 265 (1990), pp. 21128–21133.

H. Nakarnura et al., "Interleukin–8 Gene Expression in Human Bronchial Epithelial Cells," *The Journal of Biological Chemistry*, 266 (1991), pp. 19611–19617.

J. Nakano et al., "Endotoxin and Pro–inflammatory Cytokines Stimulate Endothelin–1 Expression and Release by Airway Epithelial Cells," *Clinical and Experimental Allergy*, 24 (1994), pp. 330–336.

A. Ray et al., "Activation of the Human 'β$_2$–interferon/Hepatocyte–stimulating Factor/Interleukin 6' Promoter by Cytokines, Viruses, and Second Messenger Agonists," *Proceedings of the National Academy of Sciences USA*, 85 (1988), pp. 6701–6705.

R. Robbins et al., "Inducible Nitric Oxide Synthase is Increased in Murine Lung Epithelial Cells By Cytokine Stimulation," *Biochemical and Biophysical Research Communications*, 198 (1994), pp. 835–843.

C. Ruef et al., "Regulation of Cytokine Secretion by Cystic Fibrosis Airway Epithelial Cells," *European Respiratory Journal*, 6 (1993), pp. 1429–1436.

A. Schuster et al., "Cytokines in Nuetrophil–dominated Airway Inflammation in Patients with Cystic Fibrosis," *European Archives of Otorhinolaryngology*, 252 (suppl. 1), (1995), pp. S59–S60.

J. Guy–Caffey et al., "Novel Polyaminolipids Enhance the Cellular Uptake of Oligonucleotides," *The Journal of Biological Chemistry*, 270 (1995), pp. 31391–31396.

J. Janne, et al., "Polyamines: From Molecular Biology to Clinical Applications," *Annals of Medicine*, 23 (1991), pp. 241–259.

N. Caplen, et al., "Liposome Mediated CFTR Gene Transfer to the Nasal Epithelium of Patients With Cystic Fibrosis," *Nature Medicine*, 1 (1995), pp. 39–46.

J–S. Remy et al., "Gene Transfer with a Series of Lipophilic DNA Binding Molecules," *Bioconjugate Chemistry*, 5 (1994), pp. 647–654.

J–P. Behr, "Gene Transfer with Synthetic Cationic Amphiphiles: Prospects for Gene Therapy," *Bioconjugate Chemistry*, 5 (1994), pp. 382–389.

J. Felgner, et al., "Enhanced Gene Delivery and Mechanism Studies with a Novel Series of Cationic Lipid Formulations," *The Journal of Biological Chemistry*, 269 (1994), pp. 2550–2561.

Barthel et al., "Gene Transfer Optimization with Lipospermine–Coated DNA," *DNA and Cell Biology*, 12 (1993), pp. 553–560.

J–P. Behr, "Synthetic Gene–Transfer Vectors," *Accounts of Chemical Research*, 26 (1993), pp. 274 –278.

P. Hoet, et al., "Kinetics and Cellular Localization of Putrescine Uptake in Human Lung Tissue," *Thorax*, 48 (1993), pp. 1235–1241.

J. Felgner, et al., "Cationic Lipid–Mediated Delivery of Polynucleotides," *Methods (A Companion to Methods in Enzymology)*, 5 (1993), pp. 67–75.

X. Gao, et al., "A Novel Cationic Liposome Reagent for Efficient Transfection of Mammalian Cells," *Biochemical and Biophysical Research Communications*, 179 (1991), pp. 280–285.

J. Rose, et al., "A New Cationic Liposome Reagent Mediating Nearly Quantitative Transfection of Animal Cells," *Biotechniques*, 10 (1991), pp. 520–525.

J. Loeffler, et al., "Lipopolyamine–Mediated Transfection Allows Gene Expression Studies in Primary Neuronal Cells," *Journal of Neurochemistry*, 54 (1990), pp. 1812–1815.

J. Cheetam, et al., "Cholesterol Sulfate Inhibits the Fusion of Sendai Virus to Biological and Model Membranes," *The Journal of Biological Chemistry*, 265 (1990), pp. 12404–12409.

J–P. Behr, et al., "Efficient Gene Transfer into Mammalian Primary Endocrine Cells with Lipopolyamine–Coated DNA," *Proceedings of the National Academy of Science USA*, 86 (1989), pp. 6982–6986.

R. Letsinger, et al., "Cholesteryl–Conjugated Oligonucleotides: Synthesis, Properties, and Activity as Inhibitors of Replication of Human Immunodeficiency Virus in Cell Culture," *Proceedings of the National Academy of Sciences USA*, 86 (1989), pp. 6553–6556.

L. Stamatatos, et al., "Interactions of Cationic Lipid Vesicles with Negatively Charged Phospholipid Vesicles and Biological Membranes," *Biochemistry*, 27 (1988), pp. 3917–3925.

P. Felgner, et al., "Lipofection: A Highly Efficient, Lipid–Mediated DNA–Transfection Procedure," *Proceedings of the National Academy of Sciences USA*, 84 (1987), pp. 7413–7417.

R. Rando, et al., "The Synthesis and Properties of a Functional Fluorescent Cholesterol Analog," *Biochemica et Biophysica Acta*, 684 (1982), pp. 12–20.

A. Pegg, "Polyamine Metabolism and its Importance in Neoplastic Growth and as a Target for Chemotherapy," *Cancer Research*, 48 (1988), pp. 759–774.

R. Kameji, et al., "Spermidine Uptake by Type II Pulmonary Epithelial Cells in Primary Culture," *American Journal of Physiology*, 256 (1989), pp. C161–C167.

K. Patel et al., "Modification of Vesicle Surfaces with Amphiphilic Sterols. Effect on Permeability and In Vivo Tissue Distribution," *Biochimica et Biophysica Acta*, 814 (1985), pp. 256–264.

K. Moore et al., "Squalamine: An Aminosterol Antibiotic from the Shark", *Proceedings of the National Academy of Sciences USA*, 90 (1993), pp. 1354–1358.

X. Zhou et al., "DNA Transfection Mediated by Cationic Liposomes Containing Lipopolylysine: Characterization and Mechanism of Action," *Biochimica et Biophysica Acta*, 1189, 1994, pp. 195–203.

A. Tari et al., "Structure and Function Relationship of Phosphatidylglycerol in the Stabilization of the Phosphatidylethanolamine Bilayer," *Biochemistry*, 29, 1989, pp. 7708–7712.

H. Farhood et al., "The Role of Dioleoyl Phosphatidylethanolamine in Cationic Liposome Mediated Gene Transfer," *Biochemica et Biophysica Acta*, 1235, 1995, pp. 289–295.

P. Brown et al., "Role of Head Group Structure in the Phase Behavior of Amino Phospholipids. 2. Lamellar and Nonlamellar Phases of Unsaturated Phosphatidylethanolamine Analogues," *Biochemistry*, 25, 1986, pp. 4259–4267.

S. Walker et al., "Cationic Facial Amphiphiles: A Promising Class of Transfection Agents," *Proceedings of the National Academy of Sciences USA*, 93, 1996, pp. 1585–1590.

R. Leventis et al., "Interactions of Mammalian Cells with Lipid Dispersions Containing Novel Metabolizable Cationic Amphiphiles," *Biochemica et Biophysica Acta*, 1023, 1990, pp. 123–132.

Bennett et al., "Cholesterol Enhances Cationic Liposome–Mediated DNA Transfection of Human Respiratory Epithelial Cells," *Bioscience Reports*, vol. 15, No. 1 (1995).

Li et al., "DC–Chol Lipid System in Gene Transfer," Journal of Controlled Release, 39, 373–381 (1996).

Behr et al., "Efficient Gene Transfer into Mammalian Primary Endocrine Cells with Lipopoly–amine–coated DNA," *Proc. Natl. Acad. Sci.*, vol. 86, pp. 6982–6986 (1989).

Egilmez et al., "Evaluation and Optimization of Different Cationic Liposome Formulations for in Vivo Gene Transfer," *Biochemical and Biophysical Research Communication*, 221, 169–173 (1996).

Guo et al., "Cationic Liposome Containing Noncytotoxic Phospholipid and Cholesterol Derivatives," *Journal of Liposomes Research*, 3(1), pp. 51–70 (1993).

Moradpour et al., "Efficient Gene Transfer into Mammalian Cells with Cholesteryl–Spermidine," *Biochemical and Piophysical Research Communcations*, 221, pp. 82–88 (1986).

Takeuchi et al., "Effect of Zeta Potential of Cationic Liposomes Containing Cationic Cholesterol Deratives on Gene Transfection," *FEBS Letters*, 397, pp. 207–209 (1996).

Liu et al., "New Cationic Lipid Formulations for Gene Transfer," *Pharmaceuticals Research*, vol. 13, No. 12 (1996).

Lee et al., "Detailed Analysis of Structures and Formulations of Cationic Lipids for Efficient Gene Transfer to the Lung," Human Gene Therapy, 7, pp. 1701–1717 (1996).

Vigneron et al., "Guanidinium–cholesterol Cationic Lipids: Efficient Vectors for the Transfection of Eukaryotic Cells," *Proc. Natl. Acad. Sci.*, vol. 93, pp. 9682–9686 (1996).

Weignberg, Robert A., "The Retinoblastoma Protein and Cell Cycle Control," *Cell*, vol. 81, pp. 323–330 (1995).

Zalipsky et al., Long Circulating, Cationic Liposomes Containing Amino–PEG–Phosphatidylethanolamine, *FEBS Letters*, 353, 71–74 (1994).

Woodle et al., "Sterically Stabilized Liposome Therapeutics," *Advanced Drug Delivery Reviews*, 16, 249–265 (1995).

Sunamoto et al., *Abstr. Pap. Chem. Soc.: 200 Meet., Pt. 2*, POLY 44, (1990), Biotechds Database, AN 91–03655, (1990).

Zelphati et al., "Liposomes as a Carrier for Intracellular Delivery of Antisense Oligonucleotides: a Real or Magic Bullet," *J. of Controlled Release*, 41, 99–119 (1996).

Ledley, "Nonviral Gene Therapy: The Promise of Genes as Pharmaceutical Products," *Human Gene Therapy*, 6, pp. 1129–1144 (1995).

T. Standiford et al., "Interleukin–8 Gene Expression by a Pulmonary Epithelial Cell Line—A Model for Cytokine Networks in the Lung" *Journal of Clinical Investigation*, 86 (1990), pp. 1945–1953.

A. Stadnyk, "Cytokine Production By Epithelial Cells," *The FASEB Journal 8*, (1994), pp. 1041–1047.

K. Adler et al., "Interactions Between Respiratory Epithelial Cells and Cytokines: Relationships to Lung Inflammation," *Annals of the New York Academy of Sciences*, 725 (1994), pp. 128–145.

Crystal, "Transfer of Genes to Humans: Early Lessons and Obstacles to Success," *Science*, vol. 270, pp. 404–410 (1995).

K. Brigham et al., "In Vivo Transfection of Murine Lungs with a Functioning Prokaryotic Gene Using a Loposome Vehicle," *The AmericanJournal of Medical Sciences*, 298, pp. 278–281 (1989).

M. Stewart et al., "Gene Transfer In Vivo with DNA–Liposome Complexes: Safety and Acute Toxicity in Mice," *Human Gene Therapy*, 3, pp. 267–275 (1992).

H. San et al., "Safety and Short–Term Toxicity of a Novel Cationic Lipid Formulation for Human Gene Therapy," *Human Gene Therpay*, 4, pp. 781–788 (1993).

K. Brigham et al., "Rapid Communication: Expression of Human Growth Hormone Fusion Genes in Cultured Lung Endothelial Cells and in the Lungs of Mice," *American Journal of Respiratory Cell & Molecular Biology*, 8, pp. 209–213 (1993).

A. Canonico et al., "Aerosol and Intravenous Transfection of Human α1–Antitrypsin Gene to Lungs of Rabbits," *American Journal of Respiratory Cell & Molecular Biology*, 10, pp. 24–29 (1994).

J. Conary et al., "Protection of Rbbit Lungs from Endotoxin Injury by In Vivo Hyperexpression of the Prostaglandin G/H Synthase Gene," *The Journal of Clinical Investigation*, 93, pp. 1834–1840 (1994).

Y. Liu et al., "Cationic Liposome–mediated Intravenous Gene Delivery," *The Journal of Biological Chemistry*, 270, pp. 24864–24870 (1995).

G. McLachlan et al., "Evaluation In Vitro and In Vivo of Cationic Liposome–expression Construct Complexes for Cystic Fibrosis Gene Therapy," *Gene Therapy,* 2, pp. 614–622 (1995).

M. Tsukamoto et al., "Gene Transfer and Expression in Progeny After Intravenous DNA Injection into Pregnant Mice," *Nature Genetics,* 9, pp. 243–248 (1995).

R. Mahato et al., "In Vivo Disposition Characteristics of Plamsid DNA Complexed with Cationic Liposomes," *Journal of Drug Targeting,* 3, pp. 149–157 (1995).

D. Lew et al., "Cancer Gene Therapy Using Plasmid DNA: Pharmacokinetic Study of DNA Following Injection in Mice," *Human Gene Therapy,* 6, pp. 553–564 (1995).

A. Thierry et al., "Systemic Gene Therapy: Biodistribution and Long–term Expression of Transgene in Mice," *Proceedings of the National Academy of Sciences USA,* 92, pp. 9742–9746 (1995).

* cited by examiner

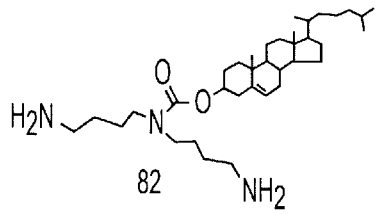
N,N BIS (4-AMINOBUTYL) CHOLESTERYL CARBAMATE
82

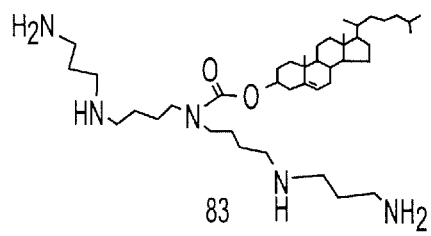
83
N,N-BIS (N'-3-AMINOPROPYL-N''-4-AMINOBUTYL) CHOLESTERYL CARBAMATE

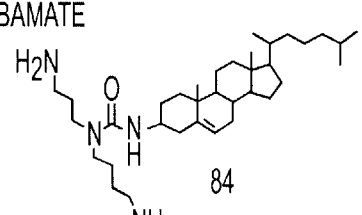
84
N$^4$-SPERMIDINE CHOLESTERYL UREA

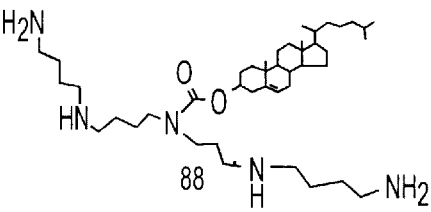
88

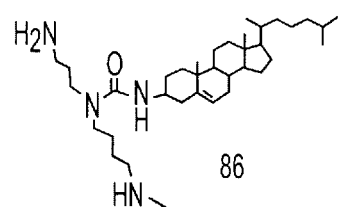
86
N$^4$-SPERMINE CHOLESTERYL UREA

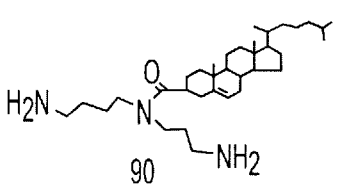
90
N$^4$ SPERMIDINE CHOLESTERYLCARBOXAMIDE

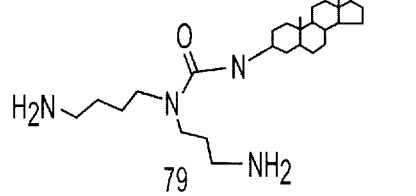
79
N$^4$-SPERMIDINE DIHYDRO CHOLESTERYL UREA

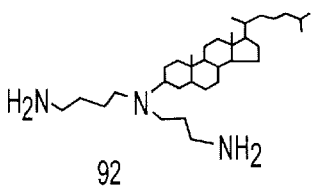
92

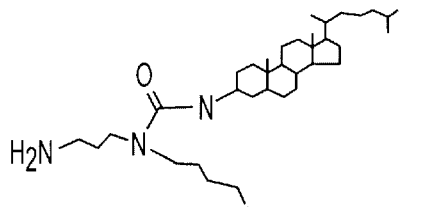
81
N$^4$-SPERMINE DIHYDRO CHOLESTERYL UREA

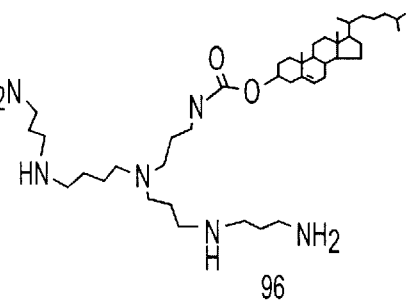
96
N-[N$^1$,N$^4$,N$^8$-TRIS (3-AMINOPROPYL) SPERMIDINE] CHOLESTERYL CARBAMATE

FIG. 1B

ERGOSTEROL (DOUBLE BONDS AS SHOWN)
ERGOSTEROL B1 (Δ, 8, 9; Δ 14, 15; Δ 22, 23)
ERGOSTEROL B1 (Δ, 6, 7; Δ 8, 14; Δ 22, 23)
ERGOSTEROL B1 (Δ, 7, 8; Δ 14, 15; Δ 22, 23)
LUMISTEROL (9β-H ISOMER OF ERGOSTEROL)

CHOLIC ACID r$^1$, r$^2$ = OH
DESOXYCHOLIC ACID r$^1$ = H, r$^2$ = OH
CHENODESOXYCHOLIC ACID r$^1$ = OH, r$^2$ = H
LITHOCHOLIC ACID r$^1$, r$^2$ = H

ANDROSTERONE

CHOLIC ACID DERIVATIVE $r^1, r^2$ = OH
DESOXYCHOLIC ACID DERIVATIVE $r^1$ = H, $r^2$ = OH
CHENODESOXYCHOLIC ACID DERIVATIVE $r^1$ = OH, $r^2$ = H
LITHOCHOLIC ACID DERIVATIVE $r^1, r^2$ = H

N1, N8 - BIS(ARGININE CARBOXAMIDE)-
N4-SPERMIDINE CHOLESTERY CARBARNATE

| LIPID # | OPT. RATIO | IN VITRO | IN VIVO |
|---|---|---|---|
| 53 | 1/1 | 4.2 | 20 |
| 65 | 1/2 | 2 | 20 |
| 67 | 1/2 | 4.8 | 150 |
| 69 | 2/1 | 2 | 2 |
| 70 | 1/1 | 1 | ND |
| 71 | 1/1 | 2.4 | 3 |
| 72 | 1/2 | 0.7 | 0.5 |
| 75 | 2/1 | 5 | 80 |
| 78 | 1/1 | 2.3 | 75 |
| 79 | 1/2 | 0.8 | ND |
| 81 | 1/2 | 0.7 | ND |
| 82 | 1/1 | 3.8 | 5 |
| 83 | 1/2 | 4 | 20 |
| 84 | 1/2 | 0.4 | 1 |
| 86 | 1/2 | 0.5 | ND |
| 88 |  |  | ND |
| 90 | 1/1 | 1.8 | 80 |
| 91 | 1/2 | 2.1 | 30 |
| 92 | 1/2 | 0.5 | ND |
| 96 | 1/2 | 5 | 45 |
| 101 | 2/1 | 1.5 | 1 |
| 104 | 2/1 | 0.7 | 0 |
| 106 | 1/2 | 1.6 | 6 |
| 107 | 1/1 | 1.3 |  |

FIG. 13

| LIPID # | OPT. RATIO | IN VITRO | IN VIVO |
|---|---|---|---|
| 87 | | | |
| 91 | 1\2 | 2.1 | 30 |
| 93 | 1\2 | 2.7 | |
| 95 | 1\2 | 3.7 | 70 |
| 97 | 1\1 | 0.4 | ND |
| 99 | 1\1 | 0 | ND |
| 100 | 1\1 | 0.1 | ND |
| 103 | | | |

*FIG. 14*

| LIPID # | OPT. RATIO | IN VITRO | IN VIVO |
|---|---|---|---|
| 64 | 1\1 | 2.1 | 1 |
| 76 | 1\1 | 1 | ND |
| 85 | 1\1 | 1.5 | 1 |
| 89 | 1\1 | 9 | 15 |
| 94 | 1\1 | 2 | 60 |
| 98 | 1\1 | 1.9 | |
| 102 | 1\2 | 10 | 40 |
| 105 | 1\2 | 3 | |
| 110 | 2\1 | 0.9 | |
| 111 | | | |

CATIONIC AMPHIPHILES FOR INTRACELLULAR DELIVERY OF THERAPEUTIC MOLECULES

This application is a continuation of U.S. patent application Ser. No. 08/668,676, filed Jun. 25, 1996, now abandoned, itself a continuation of U.S. Pat. application Ser. No. 08/564,087 entitled "Cationic Amphiphiles Containing Ester or Ether-Linked Lipophilic Groups for Intracellular Delivery of Therapeutic Molecules," filed on Oct. 20, 1995, and issued on Nov. 24, 1998, as U.S. Pat. No. 5,840,710, itself a continuation-in-part of U.S. patent application Ser. No. 08/540,867, entitled "Cationic Amphiphiles Containing Steroid Lipophilic Groups for Intracellular Delivery of Therapeutic Molecules," filed Oct. 11, 1995, and issued on May 5, 1998, as U.S. Pat. No. 5,747,471, itself being a continuation-in-part of U.S. application Ser. No. 08/352,479, entitled "Cationic Amphiphiles for Intracellular Delivery of Therapeutic Molecules," filed Dec. 9, 1994, and issued on Jul. 22, 1997, as U.S. Pat. No. 5,650,096. This application also claims the priority of (1) U.S. provisional patent application 60/004,344, filed Sept. 26, 1995, entitled "Molecular Model of Cationic Lipid/DNA Complexes," and (2) U.S. provisional application 60/004,399, filed Sept. 27, 1995, and entitled "Intravenous Delivery of Therapeutic Compositions for Gene Therapy." The complete text, claims and drawings of all of the above patents and applications are incorporated herein by reference.

BACKGROUND OF THE INVENTION

The present invention relates to novel cationic amphiphilic compounds that facilitate the intracellular delivery of biologically active (therapeutic) molecules. The present invention relates also to pharmaceutical compositions that comprise such cationic amphiphiles, and that are useful to deliver into the cells of patients therapeutically effective amounts of biologically active molecules. The novel cationic amphiphilic compounds of the invention are particularly useful in relation to gene therapy.

Effective therapeutic use of many types of biologically active molecules has not been achieved simply because methods are not available to cause delivery of therapeutically effective amounts of such substances into the particular cells of a patient for which treatment therewith would provide therapeutic benefit. Efficient delivery of therapeutically sufficient amounts of such molecules into cells has often proved difficult, if not impossible, since, for example, the cell membrane presents a selectively-permeable barrier. Additionally, even when biologically active molecules successfully enter targeted cells, they may be degraded directly in the cell cytoplasm or even transported to structures in the the cell, such as lysosomal compartments, specialized for degradative processes. Thus both the nature of substances that are allowed to enter cells, and the amounts thereof that ultimately arrive at targeted locations within cells, at which they can provide therapeutic benefit, are strictly limited.

Although such selectivity is generally necessary in order that proper cell function can be maintained, it comes with the disadvantage that many therapeutically valuable substances (or therapeutically effective amounts thereof) are excluded. Additionally, the complex structure, behavior, and environment presented by an intact tissue that is targeted for intracellular delivery of biologically active molecules often interfere substantially with such delivery, in comparison with the case presented by populations of cells cultured in vitro.

Examples of biologically active molecules for which effective targeting to a patients' tissues is often not achieved: (1) numerous proteins induding immunoglobin proteins, (2) polynucleotides such as genomic DNA, cDNA, or mRNA (3) antisense polynucleotides; and (4) many low molecular weight compounds, whether synthetic or naturally occurring, such as the peptide hormones and antibiotics.

One of the fundamental challenges now facing medical practicioners is that although the defective genes that are associated with numerous inherited diseases (or that represent disease risk factors including for various cancers) have been isolated and characterized, methods to correct the disease states themselves by providing patients with normal copies of such genes (the technique of gene therapy) are substantially lacking. Accordingly, the development of improved methods of intracellular delivery therefor is of great medical importance.

Examples of diseases that it is hoped can be treated by gene therapy include inherited disorders such as cystic fibrosis, Gaucher's disease, Fabry's disease, and muscular dystrophy. Representative of acquired disorders that can be treated are: (1) for cancers—multiple myeloma, leukemias, melanomas, ovarian carcinoma and small cell lung cancer; (2) for cardiovascular conditions—progressive heart failure, restenosis, and hemophilias; and (3) for neurological conditions—traumatic brain injury.

Gene therapy requires successful transfection of target cells in a patient. Transfection may generally be defined as the process of introducing an expressible polynudleotide (for example a gene, a CDNA, or an mRNA patterned thereon) into a cell. Successful expression of the encoding polynucleotide leads to production in the cells of a normal protein and leads to correction of the disease state associated with the abnormal gene. Therapies based on providing such proteins directly to target cells (protein replacement therapy) are often ineffective for the reasons mentioned above.

Cystic fibrosis, a common lethal genetic disorder, is a particular example of a disease that is a target for gene therapy. The disease is caused by the presence of one or more mutations in the gene that encodes a protein known as cystic fibrosis transmembrane conductance regulator ("CFTR"), and which regulates the movement of ions (and therefore fluid) across the cell membrane of epithelial cells, induding lung epithelial cells. Abnormal ion transport in airway cells leads to abnormal mucous secretion, inflammation and infection, tissue damage, and eventually death.

It is widely hoped that gene therapy will provide a long lasting and predictable form of therapy for certain disease states, and it is likely the only form of therapy suitable for many inhereted diseases. There remains however a critical need to develop compounds that faciliate entry of functional genes into cells, and whose activity in this regard is sufficient to provide for in vivo delivery of genes or other such biologically active therapeutic molecules in concentrations thereof that are sufficient for intracellular therapeutic effect.

Reported Developments

In as much as compounds designed to facilitate intracellular delivery of biologically active molecules must interact with both non-polar and polar environments (in or on, for example, the plasma membrane, tissue fluids, compartments within the cell, and the biologically active molecule itself), such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One particularly important class of such amphiphiles is the cationic amphiphiles. In general, cationic amphiphiles have polar groups that are capable of being positively charged at or around physiological pH, and this property is understood in the art to be important in defining how the amphiphiles interact with the many types of biologically active (therapeutic) molecules including, for example, negatively charged polynucleotides such as DNA.

Examples of cationic amphiphilic compounds that have both polar and non-polar domains and that are stated to be useful in relation to intracellular delivery of biologically active molecules are found, for example, in the following references, which contain also useful discussion of (1) the properties of such compounds that are understood in the art as making them suitable for such applications, and (2) the nature of structures, as understood in the art, that are formed by complexing of such amphiphiles with therapeutic molecules intended for intracellular delivery.

(1) Felgner, et al., *Proc. Natl. Acad. Sci. USA*, 84,7413–7417 (1987) disclose use of positively-charged synthetic cationic lipids including N-[1(2,3-dioleyloxy)propyl]-N,N,N-trimetylammonium chloride ("DOTMA"), to form lipid/DNA complexes suitable for transfections. See also Felgner et al., *The Journal of Biological Chemisty*, 269 (4), 2550–2561 (1994).

(2) Behr et al., *Proc. Natl. Acad. Sci. USA*, 86,6982–6986 (1989) disclose numerous amphiphiles including dioctadecylamidologlycylspermine ("DOGS").

(3) U.S. Pat. No. 5,283,185 to Epand et al. describes additional classes and species of amphiphiles including 3β [N-($N^1$,$N^1$-dimethylaminoethane)-carbamoyl] cholesterol, termed "DC-chol".

(4) Additional compounds that facilitate transport of biologically active molecules into cells are disclosed in U.S. Pat. No. 5,264,618 to Felgner et al. See also Felgner et al., *The Journal Of Biological Chemistry*, 269(4), pp. 2550–2561 (1994) for disclosure therein of further compounds including "DMRIE" 1,2-dimyristyloxypropyl-3-dimethyl-hydroxyethyl ammonium bromide, which is discussed below.

(5) Reference to amphiphiles suitable for intracellular delivery of biologically active molecules is also found in U.S. Pat. No. 5,334,761 to Gebeyehu et al., and in Felgner et al., *Metods*(Methods in Enzymology), 5,67–75 (1993).

Although the compounds mentioned in the above-identified references have been demonstrated to facilitate (although in many such cases only in vitro) the entry of biologically active molecules into cells, it is believed that the uptake efficiencies provided thereby are insufficient to support numerous therapeutic applications, particulary gene therapy. Additionally, since the above-identified compounds are understood to have only modest activity, substantial quantities thereof must be used leading to concerns about the toxicity of such compounds or of the metabolites thereof. Accordingly there is a need to develop a "second generation" of cationic amphiphiles whose activity is so sufficient that successful therapies can be achieved therewith.

SUMMARY OF THE INVENTION

This invention provides for cationic amphiphiles that are particularly effective to facilitate transport of biologically active molecules into cells; The cationic amphiphiles of the invention are divided into four (4) groups, although it will be seen that there are certain structural and functional features that many of the amphiphiles share.

Accordingly, there are provided cationic amphiphiles of Group I (see FIG. 1, panels A, B, and C) capable of facilitating transport of biologically active molecules into cells, said amphiphiles having the structure (I),

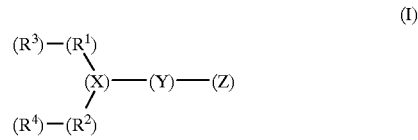

wherein:

Z is a steroid;

X is a carbon atom or a nitrogen atom;

Y is a short linking group, or Y is absent;

$R^3$ is H, or a saturated or unsaturated aliphatic group;

$R^1$ is —NH—, an alkylamine, or a polyalkylamine;

$R^4$ is H, or a saturated or unsaturated aliphatic group;

$R^2$ is —NH—, an alkylamine, or a polyalkylamine;

and wherein $R^1$ is the same or is different from $R^2$, except that both $R^1$ and $R^2$ cannot be —NH—.

In one preferred embodiment, the steroid component "Z" is selected from the group consisting of 3-sterols, wherein said sterol molecule is linked by the 3-O-group thereof, or by N— in replacement thereof, to Y (or directly to X, if Y is absent). According to this aspect of the invention, particularly effective amphiphiles include, for example, spermidine cholesterol carbamate ($N^4$-spermidine cholesteryl carbamate, amphiphile No. 53), and spermine cholesterol carbamate ($N^4$-spermine cholesteryl carbamate, amphiphile No. 67), and amphiphiles patterned thereon.

In a further preferred embodiment, the steroid group is linked to Y (or directly to X, if Y is absent) from ring position 17 of the steroid nucleus (see FIGS. 1 and 22), or from the arm that normally extends from position 17 in many steroids (see the structure of cholesterol in FIG. 1), or from any shortened form of said arm.

In other preferred embodiments, within linking group Y are contained no more than about thee or four atoms that themselves form a bridge of covalent bonds between X and Z. In a specific preferred embodiment of the invention, Y is a linking group wherein no more than one atom of said group forms a bond with both X and Z, or Y is absent.

Representative amphiphiles provided according to Group I include:

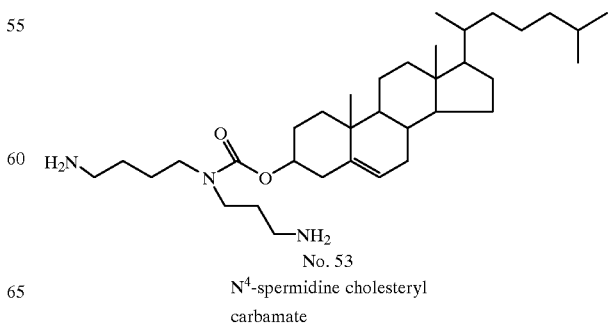

No. 53
$N^4$-spermidine cholesteryl carbamate

-continued

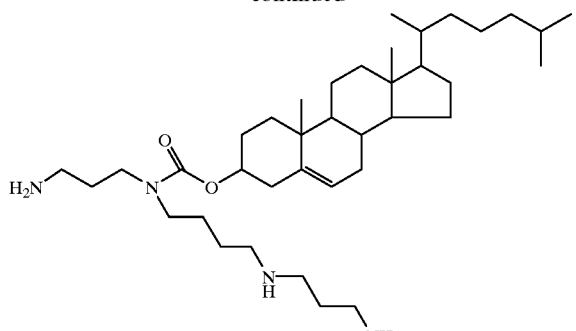

No. 67
$N^4$-spermine cholesteryl carbamate

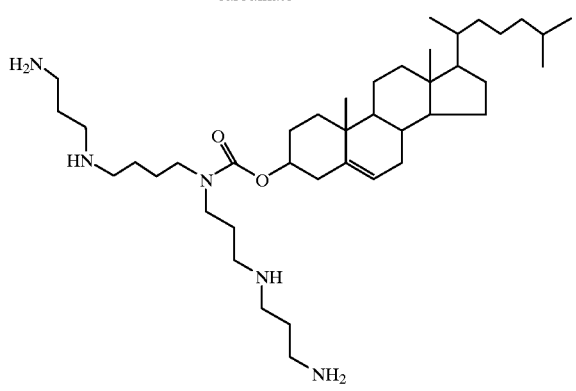

No. 75
$N^1$, $N^8$-Bis (3-aminopropyl)-$N^4$-spermidine cholesteryl carbamate

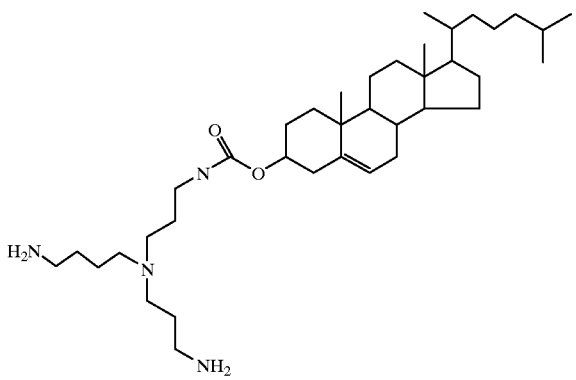

No. 78
N($N^4$-3-aminopropylspermidine) cholesteryl carbamate

Additionally there are provided cationic amphiphiles of Group II (see FIG. 5) capable of facilitating transport of biologically active molecules into cells said amphiphiles having the structure (II), $$(R^3)-(R^1) \atop (R^4)-(R^2)} (X)-(Y)-(Z) \quad (II)$$

wherein:
Z is a steroid;

X is a carbon atom or a nitrogen atom;
Y is a linking group or Y is absent,
$R^3$ is an amino acid, a derivatized amino acid, H or alkyl;
$R^1$ is —NH—, an alkylamine, or a polyalkylamine;
$R^4$ is an amino acid, a derivatized amino acid, H or alkyl;
$R^2$ is —NH—, an alkylamine, or a polyalkylamine;
and wherein $R^1$ is the same or is different from $R^2$, except that both $R^1$ and $R^2$ cannot be —NH—.

Representative amphiphiles provided according to Group II include:

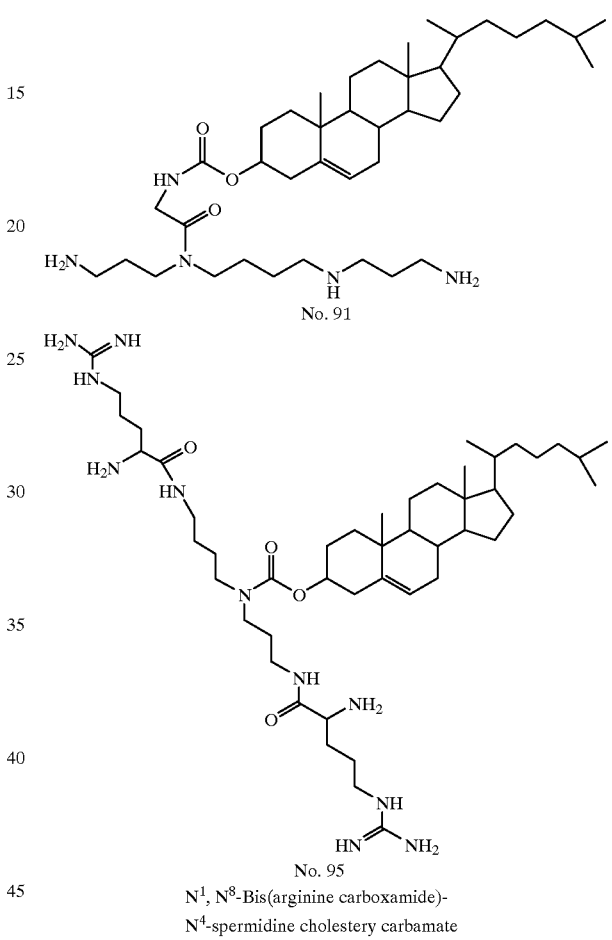

No. 91

No. 95
$N^1$, $N^8$-Bis(arginine carboxamide)-$N^4$-spermidine cholestery carbamate Additionally there are provided cationic amphiphiles of Group III (see FIG. 6) capable of facilitating transport of biologically active molecules into cells said amphiphiles having the structure (III),

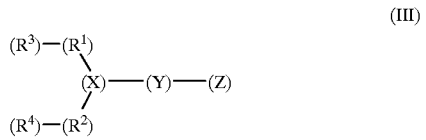

wherein:
Z is an alkylamine or a dialkylamine, linked by the N-atom thereof, to Y (or directly to X, if Y is absent), wherein if Z is a dialkylamine, the alkyl groups thereof can be the same or different;
X is a carbon atom or a nitrogen atom;
Y is a short linking group, or Y is absent;

$R^3$ is H, or a saturated or unsaturated aliphatic group;

$R^1$ is —NH—, an alkylamine, or a polyalkylamine;

$R^4$ is H, or a saturated or unsaturated aliphatic group;

$R^2$ is —NH—, alkylamine, or a polyalkylamine;

and wherein $R^1$ is the same or is different from $R^2$, except that both $R^1$ and $R^2$ cannot be —NH—.

With respect to amphiphiles provided according to Structure (III), it is again preferred that within holding group Y there are contained no more than about three or four atoms that themselves form a bridge of covalent bonds between X and Z. In a specific preferred embodiment of the invention, Y is a linking group, such as >C=O, wherein no more than one atom of said group forms a bond with both X and Z, or Y is absent.

Representative amphiphiles provided according to Group III include:.

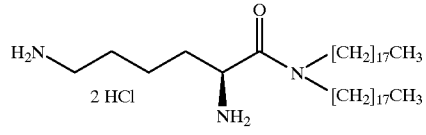

No. 43
N,N-dioctadecyllysineamide diHCl salt

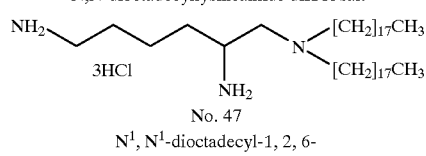

No. 47
$N^1, N^1$-dioctadecyl-1, 2, 6-triaminohexane tri HCl salt

Additionally there are provided cationic amphiphiles of Group IV (see FIG. 7) capable of facilitating transport of biologically active molecules into cells said amphiphiles having the structure (IV),

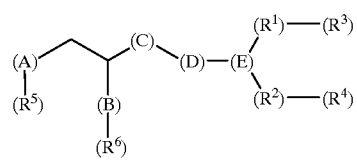

wherein:

A and B are independently O, N or S;

$R^5$ and $R^6$ are independently alkyl or acyl groups and may be saturated or contain sites of unsaturation;

C is selected from the group consisting of —CH$_2$—, >C=O, and >C=S;

E is a carbon atom or a nitrogen atom;

D is a linking group such as —NH(C=O)— or —O(C=O)—, or D is absent;

$R^3$ is H, or a saturated or unsaturated aliphatic group;

$R^1$ is —NH—, an alkylamine, or a polyalkylamine;

$R^4$ is H, or a saturated or unsaturated aliphatic group;

$R^2$ is —NH—, an alkylamine, or a polyalkylamine;

and wherein $R^1$ is the same or is different from $R^2$, except that both $R^1$ and $R^2$ cannot be —NH—.

Representative amphiphiles of Group IV include:

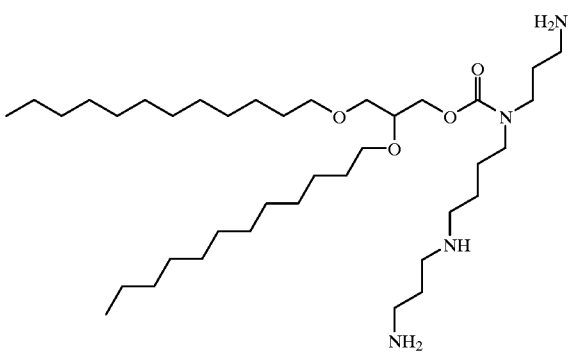

No. 89
1-($N^4$-spermine)-2, 3-dilauryl-glycerol carbamate

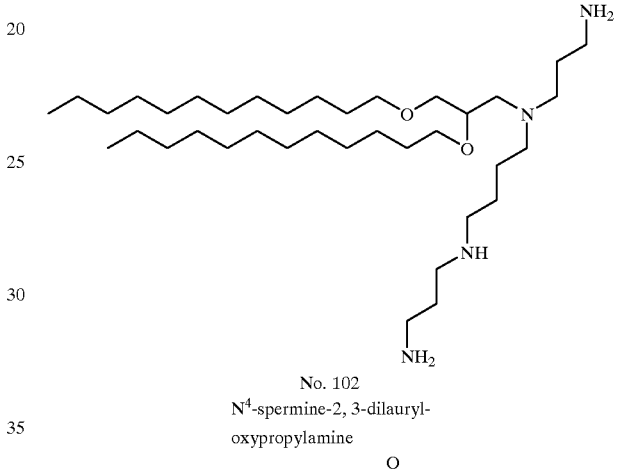

No. 102
$N^4$-spermine-2, 3-dilauryl-oxypropylamine

The invention provides also for pharmaceutical compositions that comprise one or more cationic amphiphiles, and one or more biologically active molecules, wherein said compositions facilitate intracellular delivery in the tissues of patients of therapeutically effective amounts of the biologically active molecules. The pharmaceutical compositions of the invention may be formulated to contain one or more additional physiologically acceptable substances that stabilize the compositions for storage and/or contribute to the successful intracellular delivery of the biologically active molecules.

In a further aspect, the invention provides a method for facilitating the transfer of biologically active molecules into cells comprising the steps of preparing a dispersion of a cationic amphiphile of the invention; contacting said dispersion with a biologically active molecule to form a complex between said amphiphile and said molecule, and contacting cells with said complex thereby facilitating transfer of said biologically-active molecule into the cells.

For pharmaceutical use, the cationic amphiphile(s) of the invention may be formulated with one or more additional cationic amphiphiles including those known in the art, or with neutral co-lipids such as dioleoylphosphatidylethanolamine, ("DOPE"), to facilitate delivery to cells of the biologically active molecules. Additionally, compositions that comprise one or more cationic amphiphiles of the invention can be used to introduce biologically active molecules into plant cells, such as plant cells in tissue culture.

Additionally, the present application provides for novel plasmids suitable for complexing with the amphiphiles of the invention in order to treat patients by gene therapy, so that a high level of expression of the appropriate therapeutic transgene can be achieved. Representative examples thereof include the plasmid pCMVHI and pCFI. pCF1 plasmid contains the enhancer/promoter region from the immediate early gene of cytomegalovirus. The plamid also contains a hybrid intron located between the promoter and the transgene cDNA. The polyadenylation signal of the bovine growth hormone gene was selected for placement downstream from the transgene. These and other features contribute substantially to the improved transgene expression possible with this plasmid.

Further enhancements in plasmid performance are made possible by the provision of replicating episomal plasmids. Additional therapeutic enhancements are made possible by providing plasmids in which expression of the therapeutic transgene is placed under the control of a transcriptional promoter that is sensitive to the concentration of inflammation-related substances in the target tissue. Such plasmids are of particular use for the treatment of clinical cases in which inflammation is a major complication.

In a still further embodiment of the invention, particular organs or tissues may be targeted for gene therapy, by intravenous administration of amphiphile/transgene complexes, by adjusting the ratio of amphiphile to DNA in such complexes, and by adjusting the apparent charge or zeta potential thereof.

Further additional and representative aspects of the invention are described according to the Detailed Description of the Invention which follows directly.

BRIEF DESCRIPTION OF THE DRAWINGS

FIG. 13 provides relative transfection efficiencies for Group I amphiphiles.

FIG. 14 provides relative transfection efficiencies for Group II amphiphiles.

FIG. 15 provides relative transfection efficiencies for Group IV amphiphiles.

FIG. 18 (panel B) provides a map of pCF2/CAT plasmid.

FIG. 19 (panel B) shows a plot of chloride ion transport using pCMV-b-galactosidase control.

DETAILED DESCRIPTION OF THE INVENTION

Figure 1A:
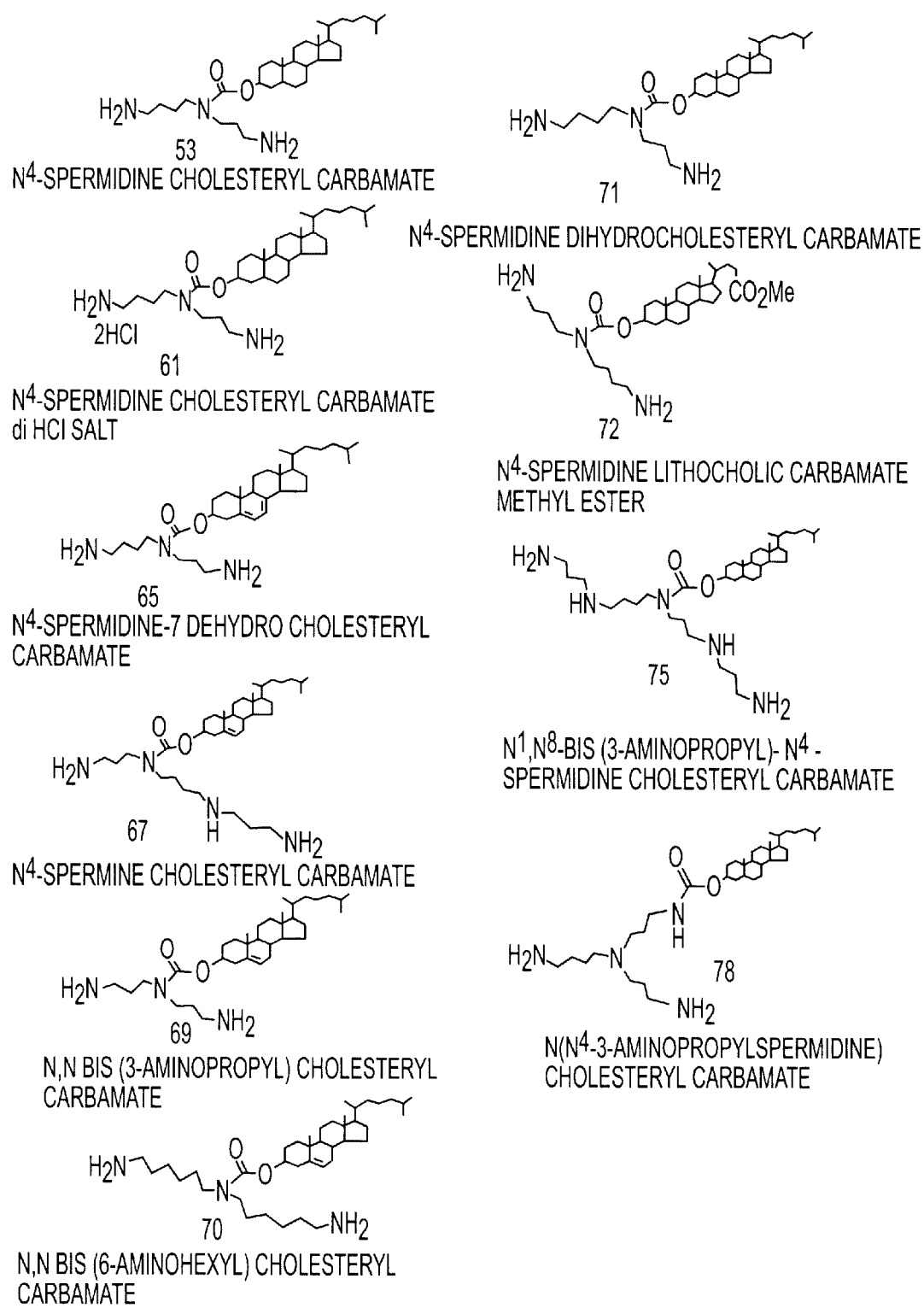
FIGS. 1a, 1b and 1c depict representative Group I cationic amphophiles.

Information Concerning the Structure of Cationic Amphiphiles of the Invention

This invention provides for cationic amphiphile compounds, and compositions containing them, that are useful to facilitate transport of biologically active molecules into cells. The amphiphiles are particularly useful in facilitating the transport of biologically active polynucleotides into cells, and in particular to the cells of patients for the purpose of gene therapy.

Cationic amphiphiles according to the practice of the invention possess several novel features. These features may be seen in comparison with, for example, cationic amphiphile structures such as those disclosed in U.S. Pat. No. 5,283,185 to Epand et al., a representative structure of which is is $3\beta$ [N-($N^1,N^1$-dimethylaminoethane)-carbamoyl] cholestrol, commonly known as "DC-chol", and to those disclosed by Behr et al. *Proc. Natl. Acad. Sci., USA*, 86, 6982–6986 (1989), a representative structure of which is dioctadecylamidologlycylspermine ("DOGS").

Cationic amphiphiles of the present invention contain distinctive structural features: (1) the presence of a lipophilic group which is connected directly, or through a linking group, to two cationic groups (see below) that themselves comprise amino, alkylamine or polyalkylamine groups, there resulting an overall and novel "T-shaped" structure; and (2) in many cases, and in comparison with numerous art-recognized amphiphiles, the use of a relatively short linking group to bring into close proximity the lipophllic and cationic regions of the amphiphile. Without being limited as to theory, it is believed that these features contribute substantially to the transfection-enhancing capability of these compounds. As an example of this, FIG. 10 below demonstrates the very substantial in vivo transfection-enhancing capability of spermidine cholesterol carbamate (a novel amphiphile of the invention) in comparsion to DC-chol and DMRIE—two well recognized transfectants.

In connection with the practice of the present invention, it is noted that "cationic" means that the R groups, as defined herein, tend to have one or more positive charges in a solution that is at or near physiological pH. Such cationic character may enhance interaction of the amphiphile with therapeutic molecules (such as nucleic acids) or with cell structures (such as plasma membrane glycoproteins) thereby contributing to successful entry of the therapeutic molecules into cells, or processing within subcompartments (such as the nucleus) thereof. In this regard, the reader is referred to the numerous theories in the art concerning transfection-enhancing function of cationic amphiphiles, none of which is to be taken as limiting on the practice of the present invention.

Biological molecules for which transport into cells can be facilitated according to the practice of the invention include, for example, genomic DNA, cDNA, mRNA, antisense RNA or DNA, polypeptides and small molecular weight drugs or hormones. Representative examples thereof are mentioned below in connection with the description of therapeutic (pharmaceutical) compositions of the invention.

In an important embodiment of the invention the biologically active molecule is an encoding polynucleotide that is expressed when placed in the cells of a patient leading to the correction of a metabolic defect. In a particularly important example, the polynucleotide encodes for a polypeptide having an amino acid sequence sufficiently duplicative of that of human cystic fibrosis transmembrane regulator ("CFTR") to allow possession of the biological property of epithelial cell anion channel regulation.

As aforementioned, characteristic and novel features of the amphiphiles of the invention include first, that the linking group that connects the two cationic amine groups to lipophilic group is very short, or absent entirely, and second, that the resultant linking of the the two cationic R groups to the lipophilic group forms a T-shaped structure when viewed from the position of atom "X" (a carbon or nitrogen atom) as depicted, for example, in Structures (I), (II), (III) and (IV, see atom "E").

As examples of the cationic amphiphiles of the invention, both spermidine cholesterol carbamate ($N^4$-spermidine cholesteryl carbamate) and spermine cholesterol carbamate ($N^4$-spermine cholestryl carbamate) have been determined to be superior transfectants in vivo in comparison with non "T-shaped" amphiphiles having otherwise equivalent amounts of cationic alkylamine structure. Superior performance (see also Example 3) has been determined for:

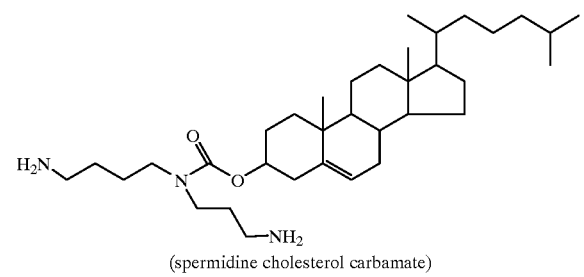
(spermidine cholesterol carbamate)

in comparison with, for example,

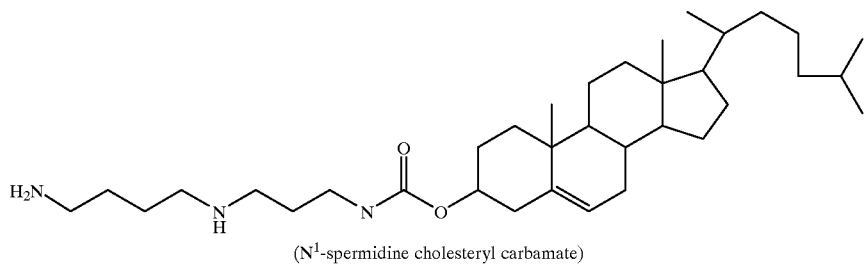
($N^1$-spermidine cholesteryl carbamate)

Additionally, superior performance has been determined for

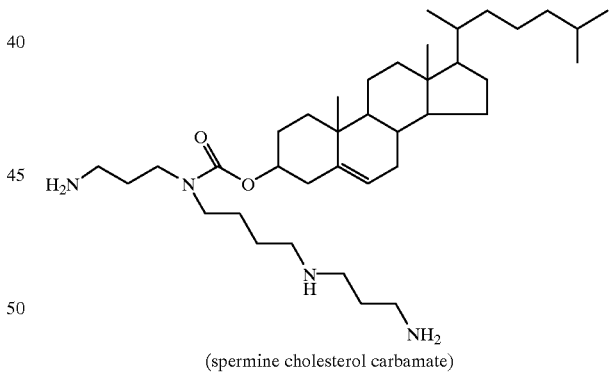
(spermine cholesterol carbamate)

in comparison with, for example,

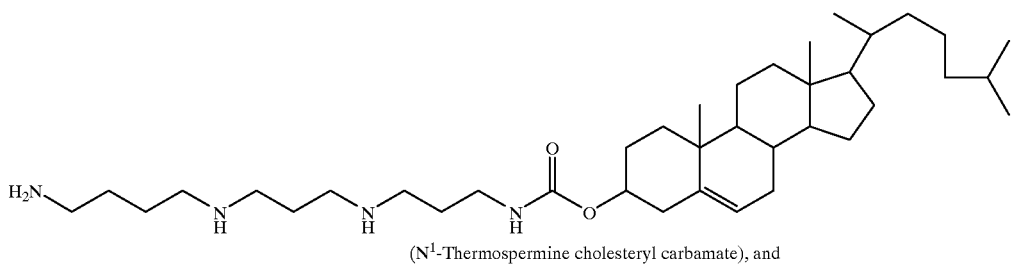
($N^1$-Thermospermine cholesteryl carbamate), and

-continued

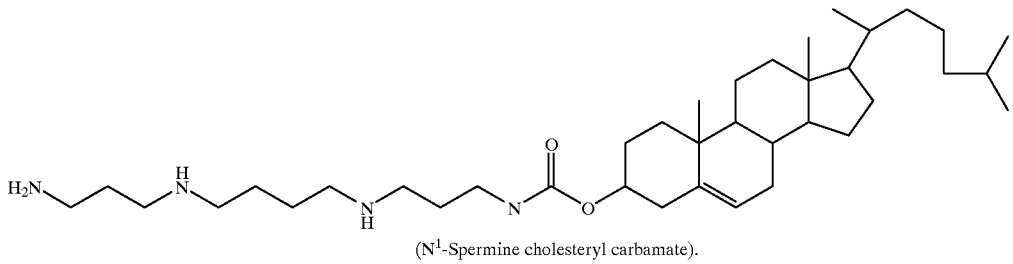

($N^1$-Spermine cholesteryl carbamate).

Applicants have also noted that numerous of the cationic amphiphiles of the invention have structural features in common with naturally occurring polyamines such as spermine and spermidine (including N-atom spacing). In this regard, the structure of amphiphiles 53, 67, 78, 90, and 91 are representative. As can be seen by examination of the data in FIGS. 13, 14 and 15, the placement of the nitrogen atoms in the polar head groups of the amphiphiles such that they are separated by one or more combinations of 3 and 4 carbon atoms leads to high in vivo transfection efficiency for plasmid transgenes complexed therewith. Applicants have also noted that these in-common structural features may have a useful effect upon the binding of the amphiphiles to DNA, and on interaction with cell surface polyamine receptors. Interaction with cell polyamine receptors may be particularly important with respect to the treatment of cancer cells by gene therapy, since the DNA replication requirements of such cells may lead to high level expression of such receptors.

Group I Amphiphiles

In connection with the design of the Group I amphiphiles of the invention, the following considerations are of note. Many of these design features are then discussed in connection with the other amphiphiles of the invention, those classified under Groups II, II and IV.

Accordingly, there are provided cationic amphiphiles of Group I (see FIG. 1, panels A, B, and C) capable of facilitating transport of biologically active molecules into cells, said amphiphiles having the structure (I),

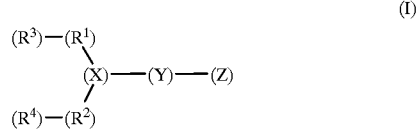

(I)

wherein:
Z is a steroid;
X is a carbon atom or a nitrogen atom;
Y is a short linking group, or Y is absent;
$R^3$ is H, or a saturated or unsaturated aliphatic group;
$R^1$ is —NH—, an alkylamine, or a polyalkylamine;
$R^4$ is H, or a saturated or unsaturated aliphatic group;
$R^2$ is —NH—, an alkylamine, or a polyalkylamine;
and wherein $R^1$ is the same or is different from $R^2$, except that both $R^1$ and $R^2$ cannot be —NH—.

The Linking Group

Preferably the linking group that connects the lipophilic group to the two cationic R groups is relatively short. It is preferred that within linking group Y are contained no more than about three or four atoms that themselves form a bridge of covalent bonds between X and Z Examples of Y groups include——$(CH_2)_2$—; —$(CH_2)_3$—; —$(CH_2)$—$(C=O)$—; —$(CH_2)_n$—NH—$(C=O)$— where n is preferably 4 or less. Additional linking groups useful in the practice of the invention are those patterned on small amino adds such as glycinyl, alanyl, beta-alanyl, serinyl, and the like.

With respect to the above representations, the left hand side thereof—as depicted—is intended to bond to atom "X", and the right hand side thereof to group "Z" (see structure I).

In certain preferred embodiments of the invention, Y is a linking group wherein no more than one atom of this group forms a bond with both "X" and "Z". Examples of preferred linking groups include —$CH_2$—, >C=S, and >C=O. Alternatively, the linking group "Y" may be absent entirely.

As aforementioned (see Structure I, directly above), "X" forms a connecting point in the amphiphiles to which is also attached the two cationic R groups. As can be seen therein (see also FIG. 1), the placement of the nitrogen atom that represents "X" dearly causes the molecule to assume a T-shape.

Steroid Lipophilic Groups

Cationic amphiphiles according to the practice of the invention may include a variety of structures as lipophilic group. Steroids represent a preferred group of such structures.

With respect to the design and orientation of steroids as lipophilic groups according to the practice of the invention, the following considerations are of note. Steroids are widely distributed in the animal, microbial and plant kingdoms. They may be defined as solid alcohols that typically contain, as their basic skeleton, 17 carbon atoms arranged in the form of a perhydrocyclopentenophenanthrene ring system. Accordingly, such compounds include bile acids, cholesterol and related substances, vitamin D, certain insect molting hormones, certain sex hormones, corticoid hormones, certain antibiotics, and derivatives of all of the above wherein additional rings are added or are deleted from the basic structure. [see Natural Products Chemistry, K. Nakanashi et al. eds., Academic Press, Inc., New York (1974), volume 1, at Chapter 6 for a further discussion of the broad classes of molecules that are understood in the art to be steroids]. Additionally, for the purposes of the invention, the term steroid is used broadly to include related molecules derived from multiple isoprenoid units, such as vitamin E. Steroids representative of those useful in the practice of the invention are shown in FIGS. 1, 2, 3 and 5.

As elaborated below, certain preferred amphiphiles of the invention include a steroid component "Z" that is selected from the group consisting of 3-sterols, wherein said sterol molecule is linked by the 3-O— group thereof, or by N— in replacement thereof, to Y (see FIG. 1). Such structures include, for example, spermidine cholesterol carbamate, spermine cholesterol carbamate, spermidine 7-dehydrocholesteryl carbamate, lysine 3-N- dihydrocholesteryl carbamate, spendine cholestamine urea, and N-3-aminopropyl-N-4-aminobutylcholestamine.

In a further preferred embodiment, the steroid group is linked to Y (or directly to X if Y is absent) from ring position 17 of the steroid nucleus (see FIGS. 1 and 3), or from the arm that normally extends from position 17 in many steroids (see FIGS. 1 and 3), or from any shortened form of said arm.

Figure 2A:
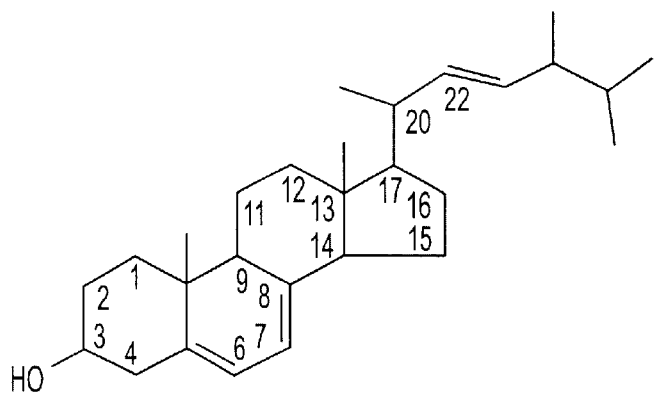
FIG. 2 depicts representative steroid lipophilic groups.
Figure 2B:
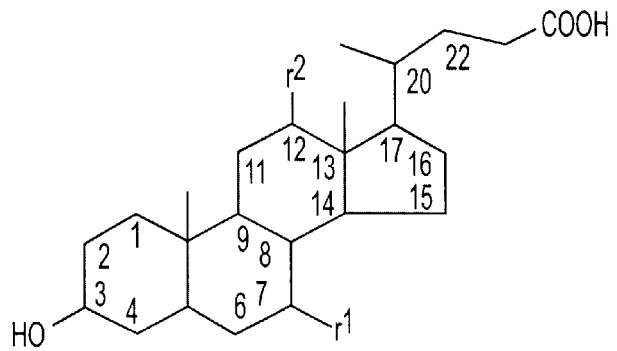
Figure 2C:
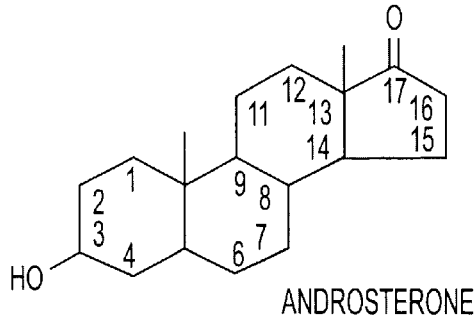

In connection with the selection of steroids for inclusion in the amphiphiles of the invention, it is preferred that the molecules have structures which can be metabolized by the body and are nontoxic at the doses thereof that are used. Preferred are steroids such as cholesterol and ergosterol that are substantially non toxic and which possess biologically normal stereospecificity in order to facilitate their safe metabolism in patients. Additional steroids useful in the practice of the invention include, for example, ergosterol B1, ergosterol B2, ergosterol B3, androsterone, cholic acid, desoxycholic acid, chenodesoxycholic acid, lithocholic acid and, for example, various derivatives thereof as are shown in the panels of FIGS. 2 and 3.

With respect to the orientation of the steroid lipophilic group, that is, how the group is attached (with or without a linker) to the cationic (alkyl) amine groups of an amphiphile, the following further information is of note. Any ring position or substituent on the steroid can in general be used as point of attachment. It is preferred, however, to use a point of attachment that (1) minimizes the complexity of chemical syntheses, and (2) is positioned near either "end" of the steroid molecule, for example, a position near ring position 3, or near ring position 17 (or the arm that typically extends therefrom). Such positions provide an orientation of the steroid with respect to the rest of the amphiphile structure that facilitates bilayer formation, and/or micelle formation, and/or stabilizes interaction with the biologically active molecules to be carried into the target cells. Representative structures showing attachment of the cationic (alkyl) amine groups to the steroid lipophilic group through the arm extending from ring position 17 therof are shown in FIG. 3 (panels A, B). With respect to this type of structure, it is further preferred that any polar groups on the steroid, such as may be attached to ring position 3, be either removed or capped (for example, hydroxy as methoxy) to avoid potentially destabilizing bilayer or micelle structures.

Figure 3A:
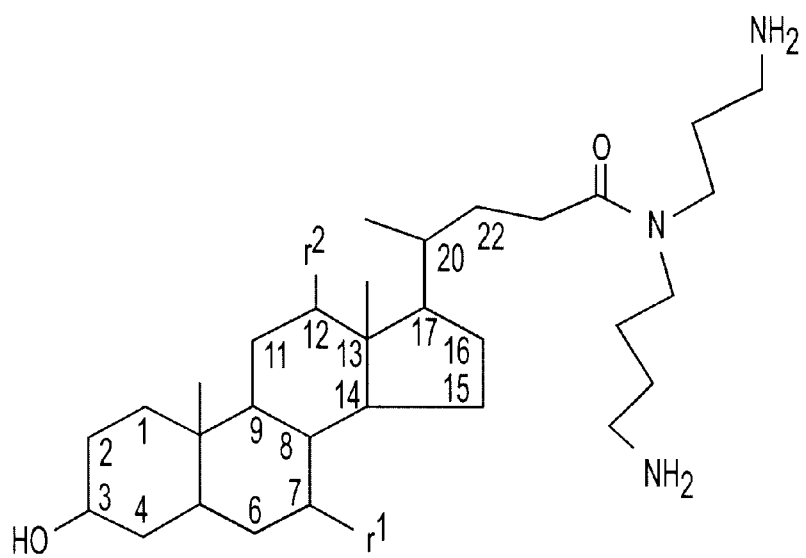
FIG. 3 depicts representative steroid lipophilic groups.
Figure 3B:
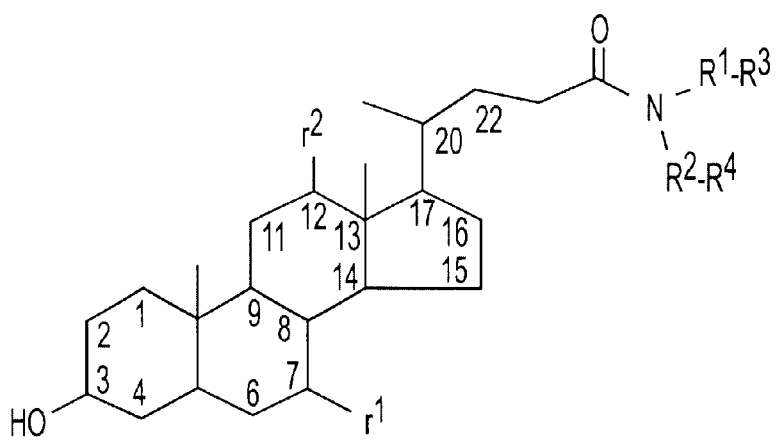
Figure 4:
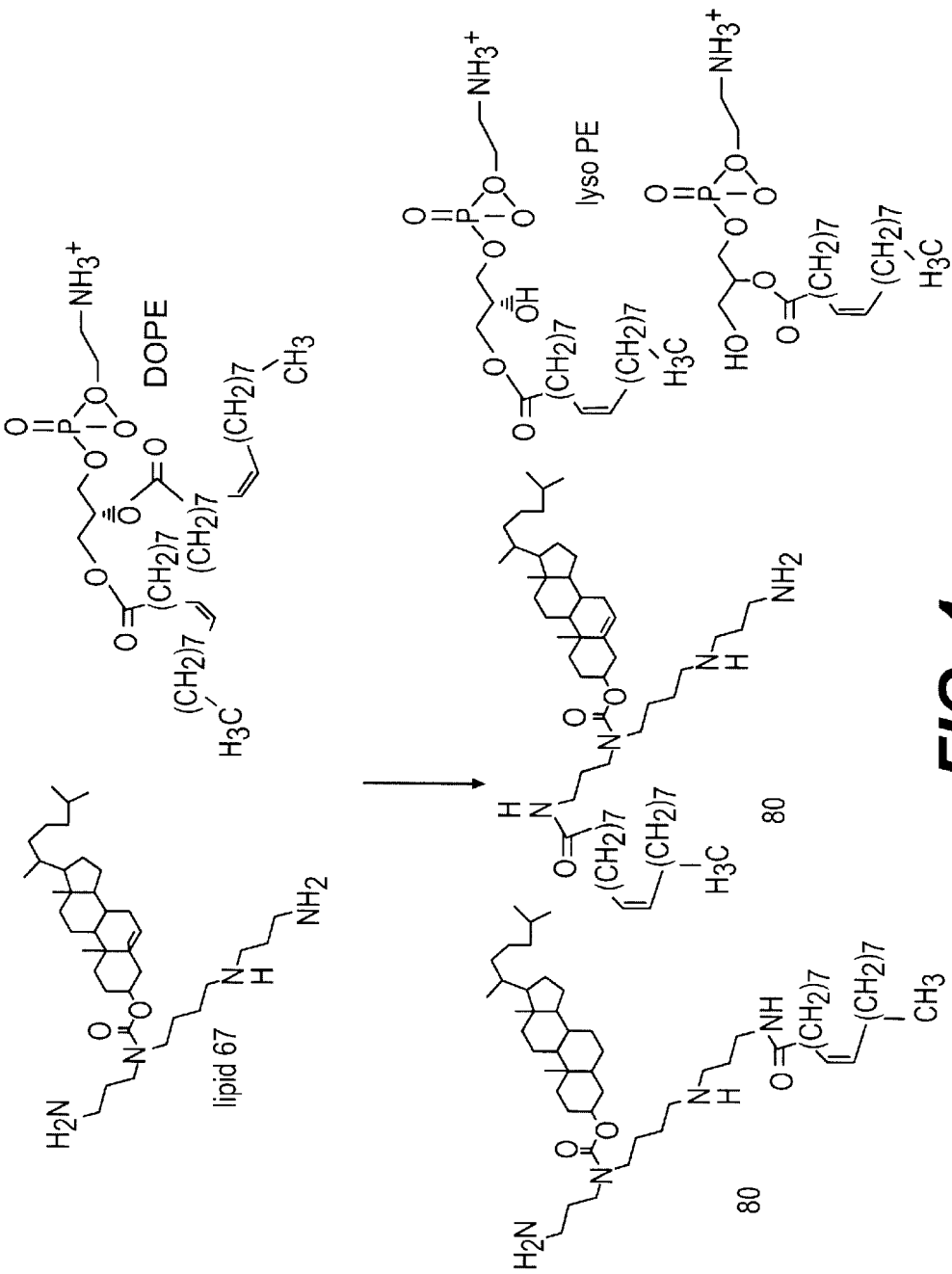
FIG. 4 depicts a transacylation reaction.

The representation in FIG. 3 of cationic amphiphiles in which the steroid lipophilic group thereof is linked to the cationic alkylamine groups through steroid ring position 17 is but an example of the invention. Similarly, the representation in FIGS. 1 to 4 of cationic amphiphiles in which the steroid lipophilic group thereof is linked to the cationic alkylamine groups through steroid ring position 3 is an example of the invention. As aforementioned, use of any steroid ring position (or moiety or branch extending therefrom) as point of attachment is within the practice of the invention.

Preferred steroids for use as group "Z" according to the practice of the invention include:

3-sterols (derived from cholesterol)

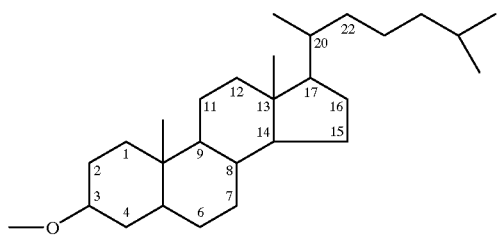

3-N steryl groups (patterned on cholesterol)

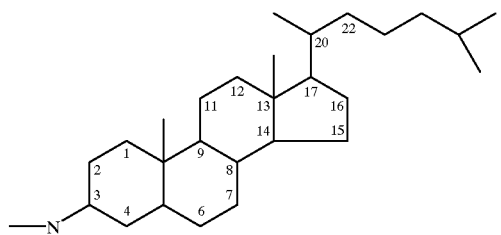

ergosterol and derivatives

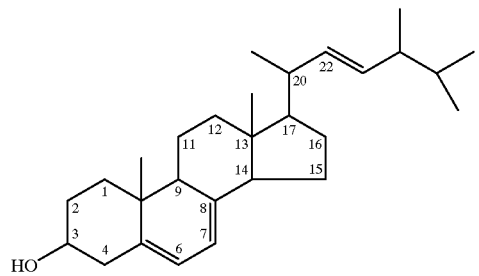

Representative species of steroid that are patterned on ergosterol and that may be used to define the structure of cationic amphiphiles of the invention include: ergosterol (double bonds as shown); ergosterol B1 (Δ8, 9; Δ14, 15; Δ22, 23); ergosterol B1 (Δ6, 7; Δ8, 14; Δ22, 23); ergosterol B1 (Δ7, 8; Δ14, 15; Δ22, 23); and lumisterol (the 9b-H isomer of ergosterol).

cholic acid and derivatives

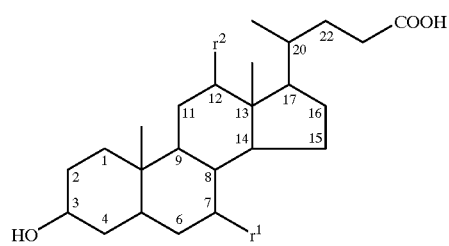

Representative species of steroid that are patterned on cholic acid and that may be used to define the structure of cationic amphiphiles of the invention include: cholic acid wherein $r^1$ and $r^2$=OH; desoxycholic acid wherein $r^1$=H and $r^2$=OH, chenodesoxycholic acid wherein $r^1$=OH and $r^2$=H; and lithocholic acid wherein $r^1$ and $r^2$=H.

androsterone and derivatives thereof

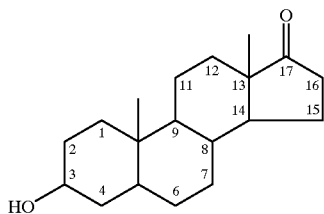

Selection of Groups $R^1$, $R^2$, $R^3$, and $R^4$

For $R^3$ and $R^4$:

According to the practice of the invention $R^3$ and $R^4$ are, independently, H, or saturated or unsaturated aliphatic groups. The aliphatic groups can be branched or unbranched. Representative groups include alkyl, alkenyl, and cycloalkyl.

For $R^1$ and $R^2$:

$R^1$ and $R^2$ represent structures recognized in the art as being amine; alkylamines (including primary, secondary, and tertiary amines), or extended versions thereof—herein termed "polyalkylaminres". It is understood that both alkylamine and polyalkylamine groups as defined herein may include one or more carbon-carbon double bonds and the use of such alkenylamines is therefore within the practice of the invention.

Representative alkylamines include: (a) —NH—$(CH_2)_z$— where z is other than 0; (b) —$[[CH_3(CH_2)_y]N]$—$(CH_2)_z$— where z is other than 0; and (c) —$[[CH_3(CH_2)_x][CH_3(CH_2)_y]]N$—$(CH_2)_z$— where z is other than 0.

With respect to the circumstance where one or both of $R^1$ and $R^2$ are tertiary amines, such as is represented in Structure (c) above, it is understood that a hydrogen atom corresponding to either $R^3$ or $R^4$, as appropriate, may or may not be present since such hydrogen atoms correspond to the N:H(+) structure whose level of protonation will vary according to pH.

The term "polyalkylamine" as referred to herein defines a polymeric structure in which at least two alkylamines are joined. The alkylamine units that are so joined may be primary or secondary, and the polyalkylamines that result may contain primary, secondary, or tertiary N-atoms. The alkylamines (sub)units may be saturated or unsaturated, and therefore the term "alkylamine" encompasses alkenylamines in the description of the invention.

Representative resultant polyallylarunes include: (d) —$[NH—(CH_2)_{(z)}]_q$—, where z is other than 0, and q is 2 or higher; (e) —$[NH—(CH_2)_{(y)}]_p$—$[NH—(CH_2)_{(z)}]_q$—, where y and z are each other than 0, and p and q are each other than 0; (f) —$[NH—(CH_2)_{(x)}]_n$—$[NH—(CH_2)_{(y)}]_p$—$[NH—(CH_2)_{(z)}]_q$—, where x, y, and z are each other than 0, and n, p and q are each other than 0; (g) —$[NH—(CH_2)_{(w)}]_m$—$[NH—(CH_2)_{(x)}]_n$—$[NH—(CH_2)_{(y)}]_p$—$[NH—(CH_2)_{(z)}]_q$—, where w, x, y, and z are each other than 0, and m, n, p, and q are each other than 0; (h) —$[NH—(CH_2)_{(w)}]_m$—$[NH—(CH_2)_{(x)}]_n$—$[[CH_3(CH_2)_y]N]$—$(CH_2)_z$—, where x, n and z are each other than 0; (i) —$[NH—(CH_2)_{(w)}]_p$—$[[CH_3(CH_2)_x]N]$—$(CH_2)_y$—$[NH—(CH_2)_{(z)}]_q$—, where w, p, y, z, and p are each other than 0; and (j) —$[NH—(CH_2)_{(v)}]l$—$[NH—(CH_2)_{(w)}]_m$—$[NH—(CH_2)_{(x)}]_n$—$[NH—(CH_2)_{(y)}]_p$—$[NH—(CH_2)_{(z)}]_q$—, where v, w, x, y, and z are each other than 0, and l, m, n, p, and q are each other than 0.

As mentioned above $R^1$ and $R^2$, independently, can be —NH—, an alkylamine, or a polyalkylamine, and can be the same or different from each other, except that both $R^1$ and $R^2$ cannot be —NH— in order to (1) preserve the "T-shape" of the resultant compound, and (2) to provide for the stability thereof. It is preferred that—in combination—the combined backbone length of $R^3R^1$ (or of $R^4R^2$) be less than about 40 atoms of nitrogen and carbon, more preferably less than about 30 atoms of nitrogen and carbon.

In the case where the $R^1$ group adjacent to $R^3$ (or $R^2$ adjacent to $R^4$) includes a terminal nitrogen atom that defines a tertiary center, then a quaternary amine is formed (at that nitrogen atom of $R^1$) if $R^3$ is an aliphatic group, and a tertiary amine remains (at that nitrogen atom of $R^1$) if $R^3$ is H. Accordingly, with respect to such resultant $R^3R^1$ or $R^4R^2$ structures, representative respective formulas are:

(k) H—$(CH_2)_{(w)}$—$[[CH_3(CH_2)_x][CH_3(CH_2)_y]N]$—$(CH_2)_z$—, where w and z are each other than zero; and (1) H—$[[CH_3(CH_2)_x][CH_3(CH_2)_y]N]$—$(CH_2)_z$—, where z is other than zero.

In connection with interpreting the structural diagrams described herein, it is intended that the attachment of $R^3R^1$— (or $R^4R^2$—) structures to atom "X" is through the right hand side (as depicted) of the $R^3R^1$—, that is, through a $CH_2$— moiety. The coefficents (i.e. v, w, x, y, and z and l, m, n, p, and q) as depicted herein represent whole numbers. For the purposes of the invention, "whole number" means 0 and the natural numbers 1,2,3,4,5,6 . . . and up, unless specifically restricted.

With respect to the amphiphiles of the invention including those represented by formulas (a) to (l), it is noted that there are certain preferences concerning the design of such groups depending on whether atom "X" as it is shown according to structure (I) above, is a nitrogen atom or a carbon atom. If "X" is nitrogen, then amphiphiles containing $R^3$–$R^1$ (or $R^4$–$R^2$) groups that end in an N atom [i.e formula (e) where z equals 0 and q=1; formula (h) where z equals 0] are not preferred, since the resultant N—N lineage involving position X results in an amphiphile that may be unstable and/or difficult to prepare. An additional group of structures that are difficult to prepare and/or are unstable is represented, for example, by the R sequence (whether in $R^1$, or bridging $R^1$ and $R^3$)—NH—$CH_2$—NH—$CH_2$—. Accordingly, use of such structures [i.e. formula (a) where Z equals 1, formula (e) where one or both of y and z equals 1] in the practice of the invention is not preferred.

With respect to the design of structures (such as those depicted above) for inclusion in cationic amphiphiles, the following further considerations are of note. Any combination of alternating amine and alkyl moieties creates an R structure within the scope of the invention. A polyalkylamine may be represented, for example, by the formulas above, although many more structures (such structures being within the scope of the invention) can be depicted by extending the number of, or types or combinations of, alkylamine subunits within the amphiphile structure. That further such variations can be made is apparent to those skilled in the art.

It is noted that a polyalkylamine group (or resultant $R^3R^1$ group) that is very long may interfere, for example, with the solubility of the resultant amphiphile, or interfere with its ability to stably interact with the biologically active molecule selected for intracellular delivery. In this regard, polyalkylamines (or resultant $R^3R^1$ groups) having a backbone length of about 40 nitrogen and carbon atoms, or more, may not be suitable for inclusion in amphiphiles. However, for each such proposed structure, its properties may be determined by experimentation, and its use is nonetheless within the practice of the invention.

Accordingly, specific alkylamine and polyalkylamine structures result as follows:

Table 1

For $R^1$ and/or $R^2$
(1) —NH—
(2) —NH—$(CH_2)_{(2)}$—
(3) —NH—$(CH_2)_{(3)}$—
(4) —NH—$(CH_2)_{(4)}$—
(5) —NH—$(CH_2)_{(6)}$—
(6) —NH—$(CH_2)_{(3)}$—NH—$(CH_2)_{(4)}$—
(7) —NH—$(CH_2)_{(2)}$—NH—$(CH_2)_{(2)}$—
(8) —NH—$(CH_2)_{(4)}$—NH—$(CH_2)_{(3)}$—
(9) —NH—$(CH_2)_{(y)}$—NH—$(CH_2)_{(z)}$—
(10) —NH—$(CH_2)_{(x)}$—NH—$(CH_2)_{(y)}$—NH—$(CH_2)_{(z)}$—
(11) —NH—$(CH_2)_{(w)}$—NH—$(CH_2)_{(x)}$—NH—$(CH_2)_{(y)}$—NH—$(CH_2)_{(z)}$—
(12) —NH—$(CH_2)_{(v)}$—NH—$(CH_2)_{(w)}$—NH—$(CH_2)_{(x)}$—NH—$(CH_2)_{(y)}$—NH—$(CH_2)_{(z)}$—
(13) —$[NH—(CH_2)_{(w)}]_m$—$[NH—(CH_2)_{(x)}]_n$—$[[CH_3(CH_2)_y]N]$—$(CH_2)_z$—
(14) —$[NH—(CH_2)_{(x)}]_n$—$[[CH_3(CH_2)_y]N]$—$(CH_2)_z$—
(15) —$[NH—(CH_2)_{(w)}]_m$—$[NH—(CH_2)_{(x)}]_n$—$[[CH_3(CH_2)_y]N]$—$(CH_2)_z$—
(16) —$[[CH_3(CH_2)_x][CH_3(CH_2)_y]N]$—$(CH_2)_z$—
(17) —NH—$(CH_2)_{(z)}$—NH—
(18) —NH—$(CH_2)_{(y)}$—NH—$(CH_2)_{(z)}$—NH—
(19) —NH—$(CH_2)_{(y)}$—CH=CH—$(CH_2)_z$—
(20) —$[NH—(CH_2)_{(w)}]_p$—$[[CH_3(CH_2)_x]N]$—$(CH_2)_y$—$[NH—(CH_2)_{(z)}]_q$—

For $R^3$ and/or $R^4$
(1) H—
(2) $CH_3$—
(3) $CH_3$—$(CH_2)_2$—
(4) $CH_3$—$(CH_2)_4$—
(5) $CH_3$—$(CH_2)_z$—
(6) $CH_3$—$[CH_3$—$(CH_2)_z]CH$—
(7) $CH_3$—$[CH_3$—$(CH_2)_2]CH$—
(8) $CH_3$—$[[CH_3$—$(CH_2)_y][CH_3$—$(CH_2)_z]]C$—
(9) $CH_3$—$(CH_2)_z$—CH=CH—$CH_2$—
(10) $CH_3$—$[CH_3$—$(CH_2)_y$—CH=CH—$(CH_2)_z]CH$—
(11) $CH_3$—$[[CH_3$—$(CH_2)_w$—CH=CH—$(CH_2)_x][CH_3$—$(CH_2)_y$—CH=CH—$(CH_2)_z]]CH$—
(12) $CH_3$—$[CH_3$—$(CH_2)_y]CH$—$(CH_2)_z$—

Group II Amphiphiles

Additionally there are provided cationic amphiphiles of Group II (see FIG. 5) capable of facilitating transport of biologically active molecules into cells said amphiphiles having the structure (II),

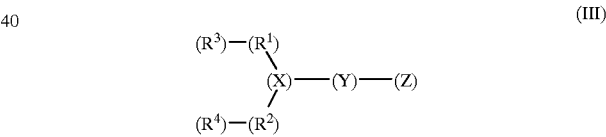
(II)

wherein:
Z is a steroid;
X is a carbon atom or a nitrogen atom;
Y is a linking group or Y is absent;
$R^3$ is an amino acid, a derivatized amino acid, H or alkyl;
$R^1$ is —NH—, an alkylamine, or a polyalkylamine;
$R^4$ is an amino acid, a derivatized amino acid, H or alkyl;
$R^2$ is —NH—, an alkylamine, or a polyalkylamine;
and wherein $R^1$ is the same or is different from $R^2$, except that both $R^1$ and $R^2$ cannot be —NH—.

Representative amphiphiles provided according to Group II include amphiphiles 87, 91, 93, 95, 97, 99, 100, and 103. With respect to the structural features of these amphiphiles, and the other amphiphiles of Group II, the following should be considered.

The steroid group may be selected according to the criteria defined above for the Group I amphiphiles. Accordingly, preferred amphiphiles include those selected from 3-sterols, wherein the sterol molecule is linked by the 3-O-group thereof; or by N in replacement thereof, to "Y".

The linking group Y of the Group II amphiphiles consists of an N-acylamino acid (or a derivative thereof), or consists of a group (such as >C=O or >C=S) wherein no more than one atom of said group forms a bond with both "X" and "Z". Optionally, group Y may be absent. Representative N-acylamino groups include an N-Acyl serine (No. 87), an N-Acyl glycine (No. 91), and an N-Acyl aspartic acid (No. 103). With respect to the use of N-Acyl aspartic acid in amphiphile No. 103, it is noted that, as provided, the gamma carboxyl thereof is further derivatized to an additional alkylamine moiety.

The criteria for selection of $R^1$ and $R^2$ are as set forth for the Group I amphiphiles. $R^3$ and $R^4$ represent H or alkyl, or may be natural or artificial amino acids including derivatives of either. Representative examples of $R^3$ or $R^4$ amino acid groups include those derived from tryptophan (No. 97) and from arginine (No. 95).

Group III Amphiphiles

Figure 6:
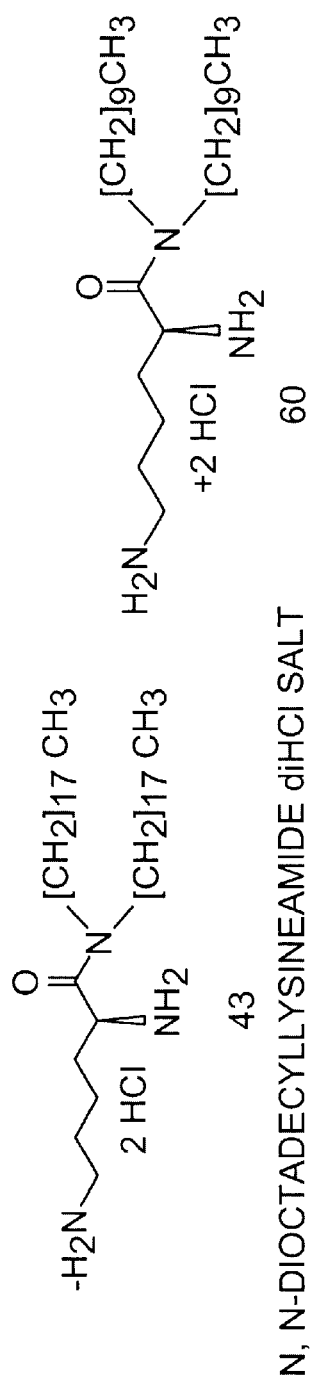
FIG. 6 depicts represenative Group III cationic amphiphiles.
Figure 6:
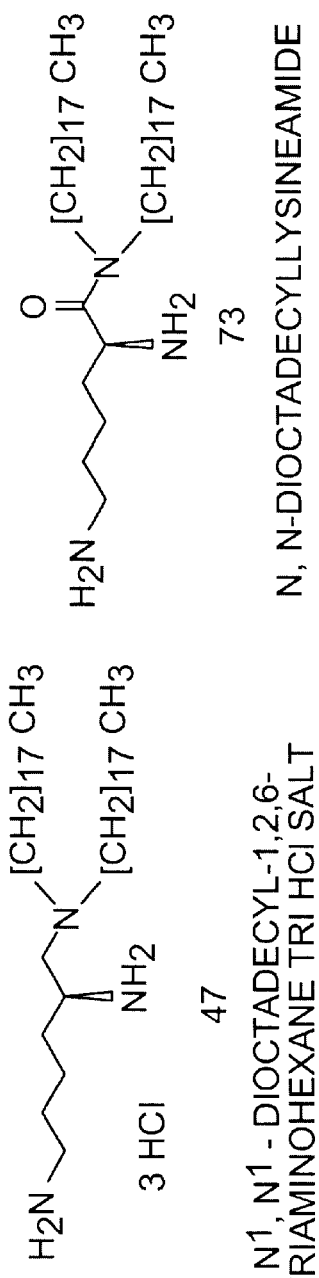
Figure 6:
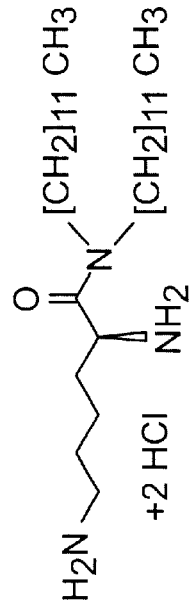

Additionally there are provided cationic amphiphiles of Group III (see FIG. 6) capable of facilitating transport of biologically active molecules into cells said amphiphiles having the structure (III),

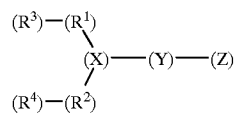
(III)

wherein:
Z is an alkylamine or a dialkylamine, linked by the N-atom thereof, to Y, or directly to X if Y is absent, wherein if Z is a dialkylamine, the alkyl groups thereof can be the same or different;
X is a carbon atom or a nitrogen atom;
Y is a short linking group, or Y is absent;
$R^3$ is H, or a saturated or unsaturated aliphatic group;
$R^1$ is —NH—, an alkylamine, or a polyalkylamine;
$R^4$ is H, or a saturated or unsaturated aliphatic group;
$R^2$ is —NH—, an alkylamine, or a polyalkylamine;
and wherein $R^1$ is the same or is different from $R^2$, except that both $R^1$ and $R^2$ cannot be —NH—.

Representative cationic amphiphiles according to the practice of the invention that contain an alkyl amine or dialkylamine as lipophilic group include, for example, N,N-dioctadecyllysineamide; $N^1,N^1$-dioctadecyl-1,2,6-triaminohexane; N,N-didodecyllysineamide; N,N-didecyllysineamide; spermidine-N,N-dioctadecyl urea; N-myristyllysineamide; and N-(dioctyldecylaminoethyl)- lysineamide. Representative amphiphiles are depicted (FIG. 6) as amphiphiles 43, 47, 56, 60, and 73. With respect to the structural features of these amphiphiles, and the other amphiphiles of Group III, the following should be considered.

With respect to the selection of the lipophilic alkylamine or dialkylamine group "Z", Table 2 below provides representative structures.

Table 2

For "Z"
(1) $CH_3-(CH_2)_{13}-NH-$
(2) $CH_3-(CH_2)_z-NH-$
(3) $[[CH_3(CH_2)_{17}][CH_3(CH_2)_{17}]]N-$
(4) $[[CH_3(CH_2)_{11}][CH_3(CH_2)_{11}]]N-$
(5) $[[CH_3(CH_2)_9][CH_3(CH_2)_9]]N-$
(6) $[[CH_3(CH_2)_x][CH_3(CH_2)_y]]N-$
(7) $[[CH_3(CH_2)_x][CH_3(CH_2)_yCH=CH(CH_2)_z]]N-$
(8) $[[CH_3(CH_2)_w][CH_3(CH_2)_xCH=CH(CH_2)_yCH=CH(CH_2)_z]]N-$

In connection with the selection of suitable alkylamine or dialkylamine groups for inclusion at position Z in the amphiphiles of the invention, an alkyl chain(s) of the group should not be so large in molecular weight that it interferes with the solubility of the amphiphile, or interferes with its ability to interact with plasmid DNA. Additionally, an alkyl chain of an alkylamine or dialkylamine may include one or more points of unsaturation.

The selection of R groups $R^1$, $R^2$, $R^3$, and $R^4$ follows that disclosed for the Group I amphiphiles, and these R groups may be selected, for example, from Table I. Linking group Y may be selected as for the Group I amphiphiles, and preferred examples thereof include $-CH_2-$, and $>C=O$.

Group IV Amphiphiles

Additionally there are provided cationic amphiphiles of Group IV (see FIG. 7) capable of facilitating transport of biologically active molecules into cells said amphiphiles having the structure (IV),

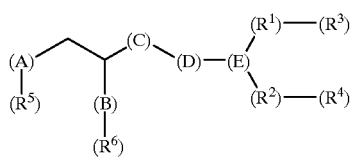

(IV)

wherein:
A and B are independently O, N or S;
$R^5$ and $R^6$ are independently alkyl or acyl groups and may be saturated or contain sites of unsaturation;
C is selected from the group consisting of $-CH_2-$, $>C=O$, and $>C=S$;
E (analogous to "X" in structures I, II, III) is a carbon atom or a nitrogen atom;
D is a linking group such as $-NH(C=O)-$ or $-O(C=O)-$, or D is absent;
$R^3$ is H, or a saturated or unsaturated aliphatic group;
$R^1$ is $-NH-$, an alkylamine, or a polyalkylamine;
$R^4$ is H, or a saturated or unsaturated aliphatic group;
$R^2$ is $-NH-$, an alkylamine, or a polyalkylamine;
and wherein $R^1$ is the same or is different from $R^2$, except that both $R^1$ and $R^2$ cannot be $-NH-$.

Representative amphiphiles of Group IV include Nos. 64, 76, 85, 89, 94, 98, 102, 105, 110, and 111. With respect to the structural features of these amphiphiles, and the other amphiphiles of Group IV, the following should be considered.

With respect to the selection of $R^1$, $R^2$, $R^3$, and $R^4$, the teachings provided for Group I, II, and III amphiphiles are applicable. As aforementioned, group "E" represents a carbon atom or a nitrogen atom.

$R^5$ and $R^6$ are independently alkyl or acyl groups, preferably containing about 8 to about 30 carbon atoms, and such groups may contain one or more points of unsaturation.

With respect to the selection of Group D, linkers such as $-NH(C=O)-$ or $-O(C=O)-$ are preferred, and are depicted such that the left side thereof in intended to bond to "C" and the right side thereof is intended to bond to "E". Optionally, group D may be absent (amphiphile No.94). Additional linkers may be selected based on the teachings provided with respect to Groups I, II, and III above, and based upon the in vivo test date derived (FIG. 15), it is preferred that the linker D be short or absent.

Co-lipids

Representative co-lipids that are useful according to the practice of the invention for mixing with one or more cationic amphiphiles include dioleoylphosphatidylethanolamine ("DOPE"), diphytanoylphosphatidylethanolamine, lyso-phosphatidylethanolamines other phosphatidylethanolamines, phosphatidylcholines, lysophosphatidylcholines and cholesterol. Typically, a preferred molar ratio of cationic amphiphile to co-lipid is about 1:1. However, it is within the practice of the invention to vary this ratio (see Example 3 below), including also over a considerable range.

It is generally believed in the art that preparing cationic amphiphiles as complexes with co-lipids (particularly neutral co-lipids) enhances the capability of the amphiphile to facilitate transfections. Although co-lipid-enhanced performance has been observed for numerous of the amphiphiles of the invention, the amphiphiles of the invention are active as transfectants without co-lipid. Accordingly, the practice of the present invention is neither to be considered limited by theories as to co-lipid participation in intracellular delivery mechanisms, nor to require the involvement of co-lipids.

Transacylation Reactions

Although heretofore unrecognized in the art, it has been determined also that certain co-lipids may react chemically with certain types of cationic amphiphiles under conditions of co-storage, there resulting new molecular species. Generation of such new species is believed to occur via mechanisms such as transacylation. In this regard, see FIG. 4 which depicts a transacylation reaction involving spermine cholesterol carbamate (No.67) and DOPE, there resulting lyso PE species and multiple forms of particular acyl-cationic amphiphile (designated No. 80).

With respect to such reactions, the following remarks are of interest With respect to use of amphiphile No.67, it has been observed that a mixture of amphiphile and DOPE, in chloroform solvent, does not appear to participate in such reactions. However, preparing the amphiphile and co-lipid in an aqueous solution where bilayer-containing structures such as liposomes can form will permit transacylation. Additionally, if amphiphile and co-lipid are dried down to a thin film, such as from chloroform (thereby placing the 2 species in intimate contact), then transacylation also occurs, possibly as a result of entropic effects. It is expected that these phenomena would also apply to lyophilized amphiphile/DOPE preparations.

Accordingly, it is highly preferred to maintain such amphiphile/DOPE preparations at very cold temperatures, such as −70 degrees C. Preparation of amphiphile No. 67 as a mono, di, or tri acetate salt has also been determined to slow transacylations.

It is to be understood that therapeutically-effective pharmaceutical compositions of the present invention may or may not contain such transacylation byproducts, or other byproducts, and that the presence of such byproducts does not prevent the therapeutic use of the compositions containing them. Rather use of such compositions is within the practice of the invention, and such compositions and the novel molecular species thereof are therefore specifically claimed.

Preparation of Pharmaceutical Compositions and Administration Thereof

The present invention provides for pharmaceutical compositions that facilitate intracellular delivery of therapeutically effective amounts of biologically active molecules. Pharmaceutical compositions of the invention facilitate entry of biologically active molecules into tissues and organs such as the gastric mucosa, heart, lung, and solid tumors. Additionally, compositions of the invention facilitate entry of biologically active molecules into cells that are maintained in vitro, such as in tissue culture. The amphiphilic nature of the compounds of the invention enables them to associate with the lipids of cell membranes, other cell surface molecules, and tissue surfaces, and to fuse or to attach thereto. One type of structure that can be formed by amphiphiles is the liposome, a vesicle formed into a more or less spherical bilayer, that is stable in biological fluids and can entrap biological molecules targeted for intracellular delivery. By fusing with cell membranes, such liposomal compositions permit biologically active molecules carried therewith to gain access to the interior of a cell through one or more cell processes including endocytosis and pinocytosis. However, unlike the case for many classes of amphiphiles or other lipid-like molecules that have been proposed for use in therapeutic compositions, the cationic amphiphiles of the invention need not form highly organized vesicles in order to be effective, and in fact can assume (with the biologically active molecules to which they bind) a wide variety of loosely organized structures. Any of such structures can be present in pharmaceutical preparations of the invention and can contribute to the effectivenesss thereof.

Biologically active molecules that can be provided intracellularly in therapeutic amounts using the amphiphiles of the invention include:
(a) polynucleotides such as genomic DNA, cDNA, and mRNA that encode for therapeutically useful proteins as are known in the art,
(b) ribosomal RNA;
(c) antisense polynucleotides, whether RNA or DNA, that are useful to inactivate transcription products of genes and which are useful, for example, as therapies to regulate the growth of malignant cells; and
(d) ribozymes.

In general, and owing to the potential for leakage of contents therefrom, vesicles or other structures formed from numerous of the cationic amphiphiles are not preferred by those skilled in the art in order to deliver low molecular weight biologically active molecules. Although not a preferred embodiment of the present invention, it is nonetheless within the practice of the invention to deliver such low molecular weight molecules intracellularly. Representative of the types of low molecular weight biologically active molecules that can be delivered include hormones and antibiotics.

Cationic amphiphile species of the invention may be blended so that two or more species thereof are used, in combination, to facilitate entry of biologically active molecules into target cells and/or into subcellular compartments thereof. Cationic amphiphiles of the invention can also be blended for such use with amphiphiles that are known in the art.

Dosages of the pharmaceutical compositions of the invention will vary, depending on factors such as half-life of the biologically-active molecule, potency of the biologically-active molecule, half-life of the amphiphile(s), any potential adverse effects of the amphiphile(s) or of degradation products thereof, the route of administration, the condition of the patient, and the like. Such factors are capable of determination by those skilled in the art.

A variety of methods of administration may be used to provide highly accurate dosages of the pharmaceutical compositions of the invention. Such preparations can be administered orally, parenterally, topically, transmucosally, or by injection of a preparation into a body cavity of the patient, or by using a sustained-release formulation containing a biodegradable material, or by onsite delivery using additional micelles, gels and liposomes. Nebulizing devices, powder inhalers, and aerosolized solutions are representative of methods that may be used to administer such preparations to the respiratory tract.

Additionally, the therapeutic compositions of the invention can in general be formulated with excipients (such as the carbohydrates lactose, trehalose, sucrose, mannitol, maltose or galactose) and may also be lyophilized (and then rehydrated) in the presence of such excipients prior to use. Conditions of optimized formulation for each amphiphile of the invention are capable of determination by those skilled in the pharmaceutical art. By way of example, for spermidine cholesterol carbamate (amphiphile No. 53), it has been determined that use of sucrose is preferred over mannitol in order to prevent formation of amphiphile/DNA aggregates, particularly as the concentration of DNA is increased therein. Addition of such excipients maintains the consistency of lyophilized pharmaceutical compositions during storage, and prevent difficulties such as aggregation, or insolubity, that may likely occur upon rehydration from the lyophilized state.

Accordingly, a principal aspect of the invention involves providing a composition that comprises a biologically active molecule (for example, a polynucleotide) and one or more cationic amphiphiles (including optionally one or more co-lipids), and then maintaining said composition in the presence of one or more excipients as aforementioned, said resultant composition being in liquid or solid (preferably lyophilized) form, so that (1) the therapeutic activity of the biologically active molecules is substantially preserved; (2) the transfection enhancing nature of the amphiphile(or of amphiphile/DNA complex) is maintained. Without being limited as to theory, it is believed that the excipients stabilize the interaction (complexes) of the amphiphile and biologically active molecule through one or more effects including:
(1) minimizing interactions with container surfaces,
(2) preventing irreversible aggregation of the complexes, and
(3) maintaining amphiphile/DNA complexes in a chemically-stable state, i.e., preventing oxidation and/or hydrolysis.

Although the presence of excipients in the pharmaceutical compositions of the invention stabilizes the compositions and facilitates storage and manipulation thereof, it has also been determined that moderate concentrations of numerous excipients may interfere with the transfection-enhancing capability of pharmaceutical formulations containing them. In this regard, an additional and valuable characteristic of the amphiphiles of the invention is that any such potentially adverse effect can be minimized owing to the greatly enhanced in vivo activity of the amphiphiles of the invention in comparison with amphiphilic compounds known in the art. Without being limited as to theory, it is believed that osmotic stress (at low total solute concentration) may contribute positively to the successful transfection of polynucleotides into cells in vivo. Such a stress may occur when the pharmaceutical composition, provided in unbuffered water, contacts the target cells. Use of such otherwise preferred compositions may therefore be incompatible with treating target tissues that already are stressed, such as has damaged lung tissue of a cystic fibrosis patient. Accordingly, and using sucrose as an example, selection of concentrations of this excipient that range from about 15 mM to about 200 mM provide a compromise betweeen the goals of (1) stabilizing the pharmaceutical composition to storage and (2) mimizing any effects that high concentrations of solutes in the composition may have on transfection performance.

Selection of optimum concentrations of particular excipients for particular formulations is subject to experimentation, but can be determined by those skilled in the art for each such formulation.

An additional aspect of the invention concerns the protonation state of the cationic amphiphiles of the invention prior to their contacting plasmid DNA in order to form a therapeutic composition. It is within the practice of the invention to utilize fully protonated, partially protonated, or free base forms of the amphiphiles in order to form such therapeutic compositions. With respect to amphiphile No. 67 (spermine cholesterol carbamate), it has been observed that when providing this amphiphile for a transfecting composition with DOPE (itself provided as a zwitterion), transgene expression was best for the free base, but decreased if the amphiphile was prepared as an acetate salt. Activity decreased step-wise through the mono and di acetate salts and was minimal for the tri-acetate salt. Under the circumstances described, the plasmid DNA provided for contacting with the amphiphile was prepared (without buffer) as a sodium salt in water.

Methods of Syntheses

The following methods illustrate production of certain of the cationic amphiphiles of the invention. Those skilled in the art will recognize other methods to produce these compounds, and to produce also the other compounds of the invention.

Group I amphiphiles (A) $N^4$-Spermidine cholesteryl carbamate

Figure 8:
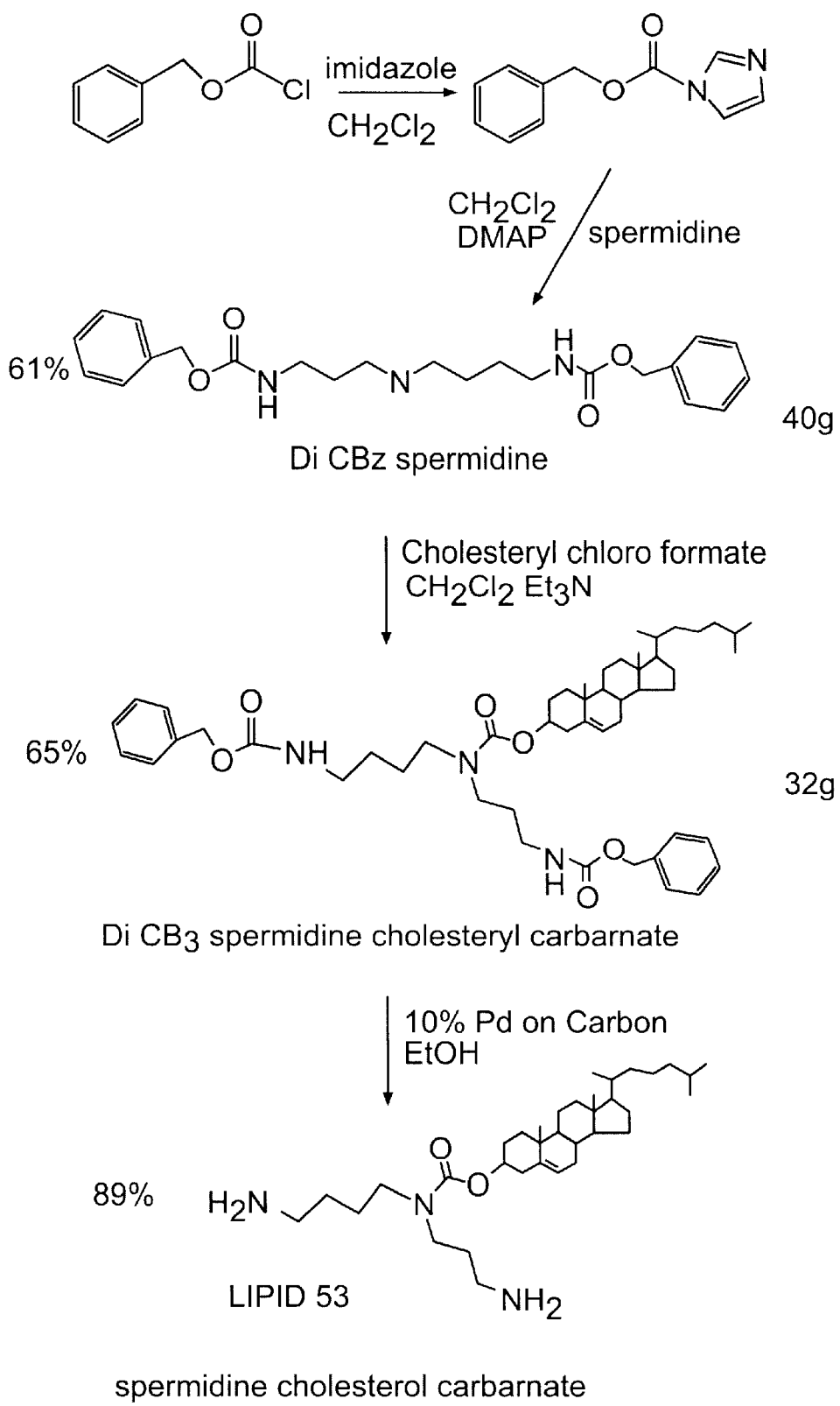
FIG. 8 provides a route of synthesis for spermidine cholesterol carbamate.

Spermidine cholesterol caxbamate (FIG. 1, No. 53) was synthesized according to the following procedure which is outlined in FIG. 8.

Synthesis of $N^1,N^8$-DiCBZ—$N^4$-Spermidine Cholesterol Carbamate $N^1,N^8$-dicarbobenzoxyspermidine (61% yield, m.p. 104–105° C.) was prepared according to the procedure of S. K Sharma, M. J. Miller, and S. M. Payne, J. Med. Chem., 1989, 32, 357–367. The $N^1,N^8$-dicarbobenzoxyspermidine (25 g, 60.5 mmol) and triethylamine (25 ml, 178 mmol) were dissolved in 625 ml of anhydrous methylene chloride, cooled to 0–4° C. and stirred under $N_2$. Cholesteryl chloroformate (27.2 g 60.6 mmol) was dissolved in 250 ml of methylene chloride and added to the reaction over a 20 minute period. A white precipitate formed upon addition. After the addition was complete, the reaction was stirred at 0–4° C. for 10 minutes and then at room temperature for 1.5 hr. At this point, the white precipitate completely dissolved. The reaction was followed by TLC with hexane/ethyl acetate 6/4 as eluent (product Rf=0.25). To this reaction mixture was added 625 ml of methylene chloride and 625 ml of water. The layers were then allowed to separate. The organic layer was dried over $MgSO_4$ and filtered. The filtrate was concentrated in vacuo to give an oil. Vacuum drying was then carried out overnight. This crude product had a glue-like consistency. The crude product was purified by column chromatography (2 kg silica gel, eluent-hexane/ethyl acetate 6/4) to give 46.8 g of the 3-β-[$N^4$-($N^1,N^8$-dicarbobenzoxyspermidine)carbamoyl] cholesterol (also described herein as $N^1$, $N^8$-diCBZ-$N^4$-spermidine cholesterol carbamate) in 93% yield.

Final Sythesis of Spermidine Cholesterol carbamate

To 6.0 grams of 10% palladium on activated carbon under $N_2$ was added a solution of 30 grams of 3-β-[$N^4$-($N^1,N^8$-dicarbenzoxyspermidine)carbamoyl] cholesterol in 1 liter of ethanol, see FIG. 13. The reaction mixture was purged with $N_2$ and stirred under $H_2$ (atmospheric pressure) for 18 hr. The mixture was again purged with $N_2$ and filtered through a 10 g bed of celite. The filter cake was washed with 2 liters of 10% triethylamine in ethanol and the combined filtrates were concentrated in vacuo to a gel. The product was then dried under vacuum overnight to a sticky solid. This crude product was purified by column chromatography (2 kg of silica gel, eluent-4 L of chloroform/methanol 95/5 followed by 30 L of chloroform/methanol/isopropylamine 95/5/5, Rf=0.24) to obtain 13.1 g of the desired spermidine cholesterol carbamate in 64% yield. HPLC (C-18 reversed phase column, linear gradient elution profile—methanol/isopropanol/water/trifluoroacetic acid 60/20/20/0.1 to methanol/isopropanol/trifluoroacetic acid 70/30/0.1 to methanol/iso-propanol/chloroform/trifluoroacetic acid 60/20 20/0.1) analysis of this material showed it to be 99.2% pure with the 7-dehydrocholesterol analog present at a level of 0.8%.

In connection with this example and those that follow, it is noted that all TLC plates were visualized with phosphomolybdic acid.

(B) $N^4$-Spermine cholesteryl carbamate

Figure 9:
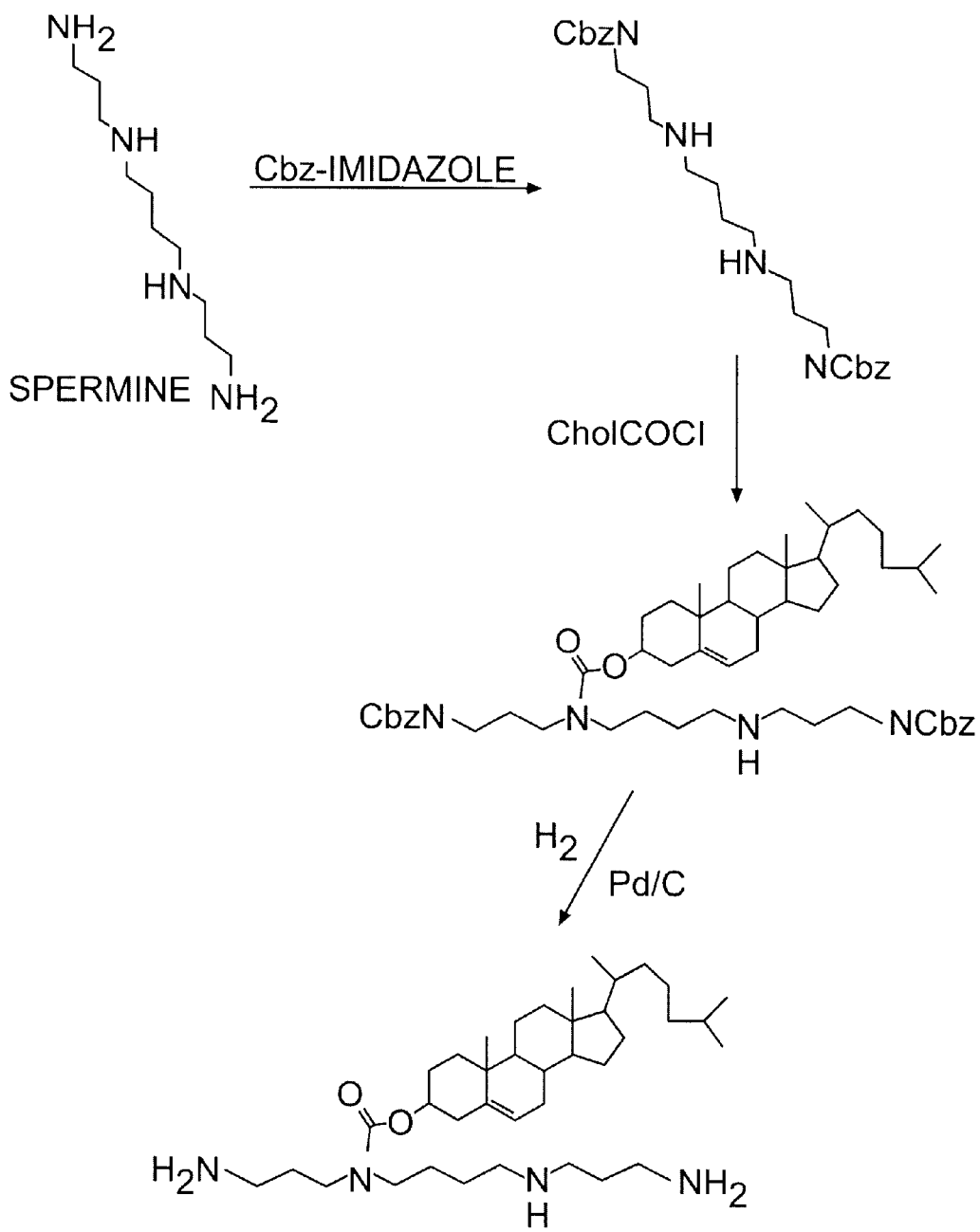
FIG. 9 provides a route of synthesis for spermine cholesterol carbamate

Spermine cholesterol carbamate (FIG. 1, No. 67) was prepared according to the following procedure which is outlined in FIG. 9.

$N^1,N^{12}$-diCBZ-spermine

Benzylchloroformate (1.76 g, 1.5 ml, 10.36 mmol) was dissolved in methylene chloride (5 ml) and placed in a Free neck flask under a nitrogen atmosphere. Imidazole (1.4 g, 20.6 mmol) was dissolved in methylene chloride (20 ml) and placed in an addition funnel. The three neck flask was cooled to 0° C. and the imidazole solution was added gradually over 20 min. The mixture was stirred at room temperature for 1 hour and then methylene chloride (25 mL) and citric acid (10%, 25 ml) were added. The layers were separated and the organic fraction was washed with citric acid (10%, 25 ml). The orgasic component was dried over magnesium sulfate and concentrated in vacuo. The residue was dried under high vacuum for 1 hour at ambient temperature.

To the residue was added dimethylaminopyridine (35 mg), methylene chloride (25 ml) and the mixture was cooled to 0° C., under a nitrogen atmosphere. To an addition fun was added a solution of spermine (1 g, 4.94 mmol) in methylene chloride (25 ml). The spermine solution was added gradually over 15 min. The reaction mixture was stirred overnight at ambient temperature and then concentrated in vacuo. The residue was dissolved in ethyl acetate (80 ml) and washed three times with water (15 ml). The organics were dried over magnesium sulfate, filtered and concentrated in vacuo to give a crude white solid. The material was purified by flash chromatography (65 g silica gel, 100:100:10 $CHCl_3$: MeOH: $NH_4OH$, product Rf.=0.33), to give after drying under high vacuum 1.01 g (2.146 mmol, 43% yield) of product.

$N^1,N^{12}$-diCBZ-$N^4$-spermine cholesteryl carbamate

Cholesteryl chloroformate (964 mg, 2.15 mmol) was dissolved in chloroform (10 ml) and added dropwise to a cooled (0° C.) solution of $N^1,N^{12}$-diCBZ spermine (1.01 g, 2.15 mmol), triethylamine (1 ml) in chloroform (10 ml). The reaction was allowed to warm to room temperature and stirred for 2 hours. To the reaction solution was added water (25 ml) and chloroform (25 ml). The layers were separated and the organic fraction dried over magnesium sulfate. The solution was concentrated in vacuo to give a crude material that was purified by flash chromatography (68 g silica gel, $MeOH/CHCl_3$ 1/4, product Rf.=0.36) to give 1.23 g (1.39 mmol, 65% yield) of product.

Final Synthesis of $N^4$-Spermine Cholesteryl Carbamate $N^1,N^{12}$-diCBZ-$N^4$-spermine cholesteryl carbamate (262 mg, 0.300 mmol) was dissolved in 5 ml of acetic acid and 45 mg of 10% Pd on C was added. The solution was purged with nitrogen and stirred under hydrogen at atmospheric pressure. The hydrogenolysis was allowed to proceed for 7 hours. The reaction mixture was filtered and the catalyst was washed with 40 ml of ethyl acetate/acetic acid 9/1 and the filtrate will be concentrated in vacuo to give a residue. The crude product was dissolved in 35 mL of 1N NaOH and extracted three times with 40 ml of chloroform/methanol 9/1. The combined organic fractions were washed with 20 mL of water and dried over $Na_2SO_4$. The solution was filtered, concentrated in vacuo and dried under vacuum to give 125 mg of the desired product in 67% yield.

In connection with the above procedure, it is noted that the hydrogenolysis should be carried out under acidic conditions, in order to minimize the poisoning of the catalyst.

Urea analogs—such as spermine or spermidine cholestamine urea—can be prepared by a sequence of reactions well known to those versed in the art of organic synthesis. For example an amine can be treated with an equal molar amount of carbonyldiimidazole followed by the addition of a second amine to give the desired urea.

(C) N,N Bis (3-aminopropryl)-O-cholestryl-3-carbamate

N,N Bis (3-aminopropyl)-O-cholesteryl-3-carbamate (FIG. 1, No. 69) was prepared according to the following procedure. Bis (3-CBZ aminopropyl) amine was prepared using the method described above for $N^1,N^{12}$-diCBZ-spermine, except that N-(3-aminopropyl)1,3-propanediamine was substituted for spermine as reactant. The pure product was isolated in 34% yield by silica gel flash chromatography using as solvent $CHCl_3$/MeOH/$NH_4OH$ 80/20/0.5.

The Bis (3-CBZ aminopropyl) amine so prepared was then reacted with cholesteryl chloroformate according to the method described above for the synthesis of $N^1,N^8$-DiCBZ-$N^4$-spermidine cholesteryl carbamate. The pure product (N,N Bis (3-CBZ aminopropyl)-O-cholesteryl-3-carbamate) was obtained in 73% yield.

Synthesis of N,N Bis(3-aminoropyl)-O-cholesteryl-3-carmate was completed by hydrogenolysis of the CBZ groups from N,N Bis(3-CBZ aminopropyl)-O-cholesteryl-3-carbamate following the procedure described above in relation to the synthesis of $N^4$-spermidine cholesteryl carbamate. The product was obtained in 23% yield without silica gel chromatography purification.

(D) N,N Bis (6-aminohexyl)-O-cholesteryl-3-carmate.

N,N Bis (6-aminohexyl)-O-cholesteryl-3-carbamate (FIG. 1, No. 70) was prepared according to the following procedure.

First, Bis (6-CBZ aminohexyl) amine was prepared using the method described above for $N^1,N^{12}$-diCBZ-spermine, except that Bis(hexamethylene)triamine was substituted for spermine as reactant. Pure product was isolated in 24% yield by recrystallition from toluene.

Bis (6-CBZ aminohexyl) amine was then reacted with cholesteryl chloroformate according to the method described above for the synthesis of $N^1,N^8$-DiCBZ-$N^4$-spermidine cholesteryl carbamate. Product N,N Bis(6-CBZ aminohexyl)-O-cholesteryl-3-carbamate was isolated in 40% yield by silica gel flash chromatography using hexanes/ethyl acetate 7/3.

(E) Lysine 3-N-dihyrocholesteryl carbamate

Lysine 3-N-dihydrocholesteryl carbamate (FIG. 1, panel C) was prepared according to the following procedure.

To a solution of dihydrocholesterol (5.0 g, 12.9 mmol, Aldrich), phthalimide (2.0 g, 13.6 mmol, Aldrich), and triphenylphosphine (3.8 g, 13.6 mmol, Aldrich) in THF (20 ml, Aldrich) stirred at 0° C. under a nitrogen atmosphere was added dropwise diethylazodicarboxylate (2.3 ml, 145 mmol, Aldrich). Upon the completion of addition the reaction mixture was allowed to warm to ambient temperature and stirred overnight. The reaction mixture was concentrated in vacuo to a residue. This residue was dissolved in 50 ml hexane/ethyl acetate 95/5 and a precipitate formed. The mixture was filtered. The filtrate was concentrated to dryness in vacuo, dissolved in 25 ml of hexane/ethyl acetate 95/5 and chromatographed on 200 g silica gel eluent 2 L hexane/ethyl acetate 95/5 then 1 L hexane/ethyl acetate 90/10). A 76% yield of the desired 3-phthalimidocholestane (5.43 g) was obtained.

The 3-phthalimidocholestane (5.40 g, 9.75 mmol) was dissolved in 60 mL of methanol and anhydrous hydrazine (3.1 ml, 99 mmol) was added. The reaction mixture was stirred and heated at reflux under a nitrogen atmosphere for 4 hr. This mixture was then cooled to room temperature, 3.1 mL of concentrated HCl was added and the resulting mixture was heated at reflux overnight. Upon cooling to ambient temperature, 100 ml of diethyl ether and 50 ml of 1 N NaOH were added (final pH of 10.1) and the layers were separated. The aqueous layer was extracted with 50 ml of diethyl ether and the combined organic fractions were filtered. The filtrate was concentrated in vacuo and the residue was purified by silica gel chromatography (chloroform/methanol 90/10) to give 2.24 g of 3-aminocholestane in 59% yield.

L-Nα,Nε-diBOClysine N-hydroxysuccinimide ester (286 mg, 0.644 mmol, Sigma) and 3-aminocholestane (250 mg, 0.644 mmol) were dissolved in 5 mL of methylene chloride, 0.1 mL of triethylamine was added and the resulting solution was stirred under a nitrogen atmosphere at ambient temperature overnight. To the reaction mixture was added 10 mL of water and 25 mL of methylene chloride and the layers were separated The aqueous layer was extracted with 25 mL of methylene chloride and the combined organic fractions were dried over $MgSO_4$ and filtered. The filtrate was concentrated in vacuo and the residue was purified by chromatography on 25 g of silica gel (eluent-hexane/ethyl acetate 6/4, sample applied in hexane/ethyl acetate 9/1). The purified material was dissolved in 25 mL of chloroform and HCl gas was bubbled through the solution for 2 hr. followed by nitrogen for 10 min. The solution was concentrated in vacuo to give 299 mg of the desired product in 79% yield as the dihydrochloride salt.

(F) $N^1,N^8$-Bis(3-aminopropyl)-$N^4$-spermidinene cholesteryl carbamate $N^1,N^8$-Bis(3-aminopropyl)-$N^4$-spermidine cholesteryl carbamate (FIG. 1, No. 75) was prepared according to the following procedure.

$N^4$-Spermidine cholesteryl carbamate (1.14 g, 2.04 mmol) was dissolved in MeOH (5 mL). Freshly distilled acrylonitrile (0.28 mL, 4.29 mmol) was added and the solution was stirred at room temperature for 18 h. The solvent was concentrated in vacuo to give an oil. Vacuum drying was then carried out overnight. The crude product was purified by column chromatography (125 g silica gel, eluent-$CHCl_3$ MeOH 1/9) to give 1.15 g (85%) of the $N^1,N^8$-Bis (cyanoethyl) $N^4$-Spermidine cholesteryl carbamate.

Raney Nickel 50% slurry (12 g, Aldrich) was placed in a Parr Bomb with 1M NaOH in 95% EtOH (50 mL). The $N^1,N^8$-Bis (cyanoethyl) $N^4$-Spermidine cholesteryl carbamate. was dissolved in EtOH (35 mL) and added to the bomb. The vesicle was evacuated and placed under Argon pressure (80–100 psi), three times and then evacuated and placed under Hydrogen pressure (100 psi), three times. The reaction was stirred under hydrogen pressure (100 psi) at room temperature for 72 h. The vesicle was evacuated and placed under argon pressure. The catalyst was removed by filtration The filtrate was concentrated in vacuo. The resulting oil was dissolved in 2:1 $CH_2Cl_2$: MeOH (100 mL) and washed with $H_2O$ (35 and 25 mL). The organic layer was dried over $Na_2SO_4$ and filtered. The filtrate was concentrated in vacuo and the residue was purified by chromatography on 100 g of silica gel (eluent-$CHCl_3$/MeOH/conc. $NH_4OH$ 40/25/10, sample applied in $CHCl_3$/MeOH 40/25). The purified material was concentrated in vacuo with iPrOH (3×50 mL) and $CH_2Cl_2$(3×50 mL) and then vacuum dried to give 986 mg (85%) of $N^1,N^8$-Bis(3-aminopropyl)-$N^4$-spermidine cholesteryl carbamate.

(G) N($N^4$-3-aminopropyl-spermidine) cholesteryl carbamate

N($N^4$-3-aminopropyl-spermidine) cholesteryl carbamate (FIG. 1, No. 78) was prepared as follows:

$N^1,N^8$-dicarbobenzoxyspermidine (1.0 g, 2.4 mmol) was dissolved in MeOH (10 mL). Freshly distilled acrylonitrile (0.3 mL, 4.5 mmol) was added and the reaction was stirred at room temperature for 18 h. The solvent was concentrated in vacuo to give an oil. The crude product was purified by column chromatography (100 g silica gel, eluent-$CHCl_3$/MeOH 1/19) to give 1.10 g (97%) of $N^4$-2-Cyanoethyl-$N^1$, $N^8$-dicarbobenzoxyspermidine.

The $N^4$-2-Cyanoethyl-$N^1,N^8$-dicarbobenzoxyspermidine (05 g, 1.07 mmol) was dissolved in MeOH (5 mL) and $CoCl_2$ (280 mg, 2.15 mmol, Aldrich) was added. The blue solution was cooled in an ice bath and $NaBH_4$ (405 mg, 10.7 mmol, Aldrich) was added in portions over 15 min. The resulting black solution was stirred at room temperature for 1 h. The black solution turned blue over this period. To the reaction was added $CH_2Cl_2$/MeOH 2/1 (30 mL). A black ppt formed. To this was added $H_2O$ (20 mL) and the mixture was filtered. The resulting layers were separated and the organic layer dried with $MgSO_4$. The drying agent was filtered and the filtrate concentrated in vacuo to give an oil. The crude product was purified by column chromatography (50 g silica gel, eluent-$CHCl_3$/MeOH/conc $NH_4OH$ 100/100/5) to give 309 mg (62%) of the $N^4$-3-aminopropyl-$N^1,N^8$- dicarbobenzoxyspermidine.

To the $N^4$-3-aminopropyl-$N^1,N^8$-dicarbobenzoxyspermidine (300 mg, 0.66 mmol) dissolved in $CH_2Cl_2$ was added $Et_3N$ under $N_2$. Cholesteryl chloro formate (326 mg, 0.726 mmol, Aldrich) was dissolved in $CH_2Cl_2$ and added to the reaction dropwise. The mixture was stirred for 2 h at room temperature. After adding $CH_2Cl_2$ (25 mL) and $H_2O$ (10 mL), the layers were separated. The organic layer was dried with $MgSO_4$ and filtered. The filtrate was concentrated in vacuo to give 640 mg of crude product. The residue was purified by chromatography on 80 g of silica gel (eluent-$CHCl_3$/MeOH 90/10, sample applied in $CHCl_3$/MeOH 90/10). The purified material was concentrated in vacuo and then vacuum dried to give 329 mg (57%) of N-($N^4$-3-aminopropyl-$N^1,N^8$-dicarbobenzoxyspermidine) cholesteryl carbamate.

To 10% Pd on carbon (65 mg, Aldrich) was added a solution of N-($N^4$-3-aminopropyl-$N^1,N^8$-dicarbobenzoxyspermidine) cholesteryl carbamate (300 mg) in acetic acid (25 mL). The reaction was placed under $H_2$ and stirred at room temperature overnight. After being placed under $N_2$, the reaction was filtered. The catalyst was washed with 10% acetic acid in EtOAc (50 mL). The filtrate was concentrated in vacuo to give an oil. The oil was dissolved in 2/1 $CH_2Cl_2$/MeOH (35 mL) and washed with 1 M NaOH (15 mL). The organic layer was dried with $MgSO_4$ and filtered. The filtrate was concentrated in vacuo and vacuum dried to give 196 mg (93%) of N-($N^4$-3-aminopropylspermidine) cholesteryl carbamate.

(H) N-[$N^1,N^4,N^8$-Tris (3-aminopropyl) spermidine] cholesteryl carbamate

N-[$N^1,N^4,N^8$-Tris (3-aminopropyl) spermidine] cholesteryl carbamate (FIG. 1, No. 96) was prepared by reacting N-($N^4$-3-aminopropylspermidine) cholesteryl carbamate with acrylonitrile (90% yield) and subsequent reduction of the di adduct with Raney nickel (75% yield) as described for the preparation of $N^1,N^8$Bis(3-aminopropyl)-$N^4$-spermidine cholesteryl carbamate.

(I) N,N-Bis(4-aminobutyl) cholesteryl carbamate

N,N-Bis(4-aminobutyl) cholesteryl carbamate (FIG. 1, No. 82) was prepared as follows.

To a mixture of Benzylamine (2.0 g, 18.6 mmol, Aldrich), $Na_2CO_3$ (4.4 g, 42 mmol) and KI (1.4 g, 9.5 mmol) in n-butanol (50 mL) was added 4-Chlorobutyronitrile (4.0 mL, 95 mmol) under nitrogen. The reaction was stirred at reflux of 48 h under nitrogen. After cooling to room temperature, diethyl ether (50 mL) was added and the precipitate filtered off. The filtrate was concentrated in vacuo to an oil. Toluene (100 mL) was added and the solution was concentrated in vacuo. Chloroform (100 mL) was added and again the solution was concentrated in vacuo and then vacuum dried for 18 h. The resulting oil was dissolved in Chloroform (100 ml) filtered and concentrated in vacuo. The crude product was purified by column chromatography (250 g silica gel, eluent-hexanes/EtOAc 60/40) to give 3.75 g (97%) of N,N-Bis (3-cyanopropyl) benzylamine.

The N,N-Bis (3-cyanopropyl) benzylamine (3.7 g, 17.8 mmol) was dissolved in EtOH (150 mL) and Acetic acid (4 mL) was added. This solution was added to 10% Pd on carbon (400 mg) under $N_2$. The mixture was placed under $H_2$ and the reaction stirred for 18 h at room temperature. The reaction was placed under $N_2$. The catalyst was filtered off and washed with EtOH (150 mL). The filtrate was concentrated in vacuo, chloroform (50 mL) was added and again concentrated in vacuo. The resulting oil was vacuum dried for 0.5 h and used directly in the next reaction. To this oil dissolved in $CH_2Cl_2$ (100 mL) was added $Et_3N$ (5 mL, 35 mmol) under $N_2$ and the solution cooled in an ice bath. Cholesteryl chloro formate (6.2 g, 13.87 mmol) was dissolved in $CH_2Cl_2$ (100 mL) and this solution was added to the reaction dropwise over 10 min. The cooling bath was removed and the reaction stirred at room temperature for 18 h under $N_2$.$CH_2Cl_2$ (100 mL) and $H_2O$ (100 mL) was added and the resulting layers were separated. The organic layer was dried with $MgSO_4$ and filtered. The filtrate was concentrated in vacuo and vacuum dried for 1 h. The crude product was purified by column chromatography (600 g silica gel, eluent-hexanes/EtOAc 60/40) to give 1.05 g (10%) of N,N-Bis (3-cyanopropyl) cholesteryl carbamate.

Raney Nickel 50% slurry (1.2 g) was placed in a Parr Bomb with 1M NaOH in 95% EtOH (50 mL). The N,N-Bis (3-cyanopropyl) cholesteryl carbamate (1.0 g, 1.77 mmol was dissolved in EtOH (100 mL) and added to the bomb. The vesicle was evacuated and placed under Argon pressure (80–100 psi), three times and then evacuated and placed under. Hydrogen pressure (100 psi), three times. The reaction was stirred under hydrogen pressure (100 psi) at room temperature for four days. The vesicle was evacuated and placed under argon pressure. The catalyst was removed by filtration. The filtrate was concentrated in vacuo. The resulting oil was dissolved in 2:1 $CH_2Cl_2$ MeOH (250 mL) and washed twice with $H_2O$ (75 and 50 mL). The organic layer was dried over $Na_2SO_4$ and filtered. The filtrate was concentrated in vacuo and the residue was purified by chromatography on 110 g of silica gel (eluent-$CHCl_3$/MeOH/ iPrNH$_2$ 95/5/5, sample applied in $CHCl_3$/MeOH 95/5). The purified material was concentrated in vacuo and then vacuum dried to give 900 mg (85%) of N,N¯Bis(4-aminobutyl) cholesteryl carbamate.

(I) N,N-Bis(N'-3-aminopropyl-4-aminobutyl) cholesterol carbamate

N,N-Bis(N'-3-aminopropyl-4-aminobutyl) cholesteryl carbamate (FIG. 1, No. 83) was prepared by reacting N,N¯ Bis(4-aminobutyl) cholesteryl carbamate with acrylonitrile (82% yield) and subsequent reduction of the di acrylonitrile adduct with Raney nickel (81% yield) as described for the preparation of $N^1,N^8$-Bis(3-aminopropyl)-$N^4$-spermidine cholesteryl carbamate.

(K) $N^4$ Spermidine cholesteryl carboxamide $N^4$ Spermidine cholesteryl carboxamide (FIG. 1, No. 90) was prepared as follows.

A solution of cholesteryl chloride (5.0 g, 12.3 mmol) in THF (50 mL) was added dropwise over 0.5 h under reflux to Magnesium turnings (390 mg) in (25 mL). Initially a pinch of Iodine and three drops of Iodomethane were added to initiate the reaction. After refluxing for 3 h. the reaction was cooled to room temperature. This mixture was poured onto Dry ice (10 g) and then stirred for 1 h. This solution was cooled in an ice bath and added to ice cold 1 M $H_2SO_4$ (100 mL). After stirring for 5 min., sodium chloride (1 g) and diethyl ether (100 mL) was added. The layers were separated and the aqueous layer was extracted with diethyl ether (100 mL). The combined organic layers were washed with a solution of Sodium thiosulfate pentahydrate (120 mg) in $H_2O$ (30 mL). The organic layer was concentrated in vacuo and vacuum dried for 18 h. The crude solid was titrated with hexanes (25 mL). After filtration the solid was washed with ice cold hexanes (10 mL). The solid was vacuum dried for 1h. The cholesteryl carboxylic acid obtained (3.0 g, 59%) was ca. 90% pure and used without further purification.

Cholesteryl carboxylic acid (500 mg, 1.2 mmol) and N-hydroxysuccinimide (140 mg, 1.2 mmol) was dissolved in $CH_2Cl_2$. To this solution was added Dicyclohexylcarbodiimide (275 mg, 1.32 mmol) was added and the reaction was stirred under $N_2$ for 2h. $N^1,N^8$-dicarbobenzoxyspermidine (474 mg, 1.2 mmol) and $Et_3N$ (1.0 mL, 7.1 mmol) was added and the reaction was stirred under $N_2$ for 72 h. The reaction was filtered and the precipitate was washed with $CH_2Cl_2$ (50 mL). The filtrate was washed with $H_2O$ (25mL). The separated organic layer was dried over $MgSO_4$ and filtered. The filtrate was concentrated in vacuo and the residue was purified by chromatography on 150 g of silica gel (eluent-hexanes/EtOAc 1/1). The purified material was concentrated in vacuo and then vacuum dried to give 680 mg (70%) of $N^1,N^8$-dicarbobenzoxy-$N^4$-spermidine cholesteryl carboxamide.

The carbobenzoxy group were removed from $N^1,N^8$-dicarbobenzoxy-$N^4$-spermidine cholesteryl carboxamide as described in the preparation of $N^4$-spermidine cholesteryl carbamate. The purified product, $N^4$ Spermidine cholesteryl carboxamide, was obtained in 53% yield.

Group II Amphiphiles (A) $N^1,N^8$-Bis(Arginine carboxamide)-$N^4$-spermidine cholesteryl carbamate $N^1,N^8$-Bis(Arginine carboxamide)-$N^4$-spermidine cholesteryl carbamate (FIG. 5, No. 95) was prepared as follows.

To $N^{(a)},N^{(e)},N^{(e)}$ (alpha, epsilon, epsilon)-tricarbobenzoxy Arginine in $CH_2Cl_2$ (25 mL) was added N-hydroxysuccinimide (100 mg, 0.89 mmol) and dicyclohexylcarbodiimide (240 mg, 0.89 mmol). The mixture was stirred under $N_2$ at room temperature for 25 hours. $N^4$-Spermidine Cholesteryl Carbamate (250 mg, 0.448 mmol) and $Et_3N$ (0.25 mL, 1.8 mmol) was added and the reaction stirred at room temperature under $N_2$ for 72 h. The reaction was filtered and the precipitate was washed with $CH_2Cl_2$ (20 mL). The filtrate was washed with $H_2O$ (20 mL). The separated organic layer was dried over $MgSO_4$ and filtered. The filtrate was concentrated in vacuo and the residue was purified by chromatography on 70 g of silica gel (eluent-$CHCl_3$/MeOH 95/5). The purified material was concentrated in vacuo and then vacuum dried to give 533 mg (71%) of $N^1,N^8$-Bis ($N^{(a)}$, $N^{(e)}$, $N^{(e)}$-tricarbobenzoxy Arginine carboxamide)-$N^4$-spermidine cholesteryl carbamate. The carbobenzoxy group were removed from $N^1,N^8$-Bis ($N^{(a)},N^{(e)},N^{(e)}$-tricarbobenzoxy Arginine carboxamide)-N-spermidine cholesteryl carbamate as described in the preparation of N-($N^4$-3-aminpropylspermidine) cholesteryl carbamate. The product, $N^1,N^8$-Bis(Arginme carboxamide)-$N^4$-spermidine cholesteryl carbamate was obtained in 27% yield.

Group III Amphiphiles (A) N,N-Dioctadecyllysineamide

N,N-dioctadecyllysineamide (FIG. 6, No.73) was prepared according to the following procedure. N,N-dioctadecylamine (1.35 g, 2.58 mmol, Fluka) and L-Nα,Nε-diBOClysine N-hydroxysuccinimide ester (1.00 g, 2.58 mmol, Sigma) were combined in 15 ml of methylene chloride and 2 ml triethylamine was added. The reaction mixture was heated briefly to effect complete dissolution and then stirred at ambient temperature overnight. Water (20 ml) and methylene chloride (50 ml) were added to the reaction mixture and the layers were separated. The aqueous fraction was extracted a second time with 50 ml methylene chloride. The combined organic fractions were dried over $MgSO_4$, filtered and concentrated in vacuo. The residue was purified by column chromatography (150 g silica gel, eluent-hexane/ethyl acetate 8/2). The purified material, N,N-dioctadecyl-Nα,Nε-diBOC lysineamide (1.59 g) was dissolved in 25 ml of chloroform and stirred for 2 hr. while HCl gas was bubbled through the solution. This solution was purged with $N_2$ gas and concentrated in vacuo. N,N-dioctadecyllysineamide (1.34 g) was obtained in 68% yield as the di HCl salt.

(B) $N^1,N^1$-Dioctadecyl-1,2,6-triaminohexane $N^1,N^1$-Dioctadecyl-1,2,6-triaminohexane (FIG. 6, No. 47) was prepared as follows. To N,N-Dioctadecyl-Nα,Nε-diBOClysineamide (760 mg, 0.823 mmol) in 30 ml anhydrous stirred at ambient temperature was added $LiAlH_4$ (185 mg, 4.87 mmol) in portions. The reaction mixture was stirred at ambient temperature overnight under a nitroge atmosphere. The reaction was quenched by the dropwise addition of 2 ml water and the resulting solution was concentrated in vacuo. To this residue was added in order 10 mL of 1 M HCl, 50 ml of methylene chloride, and 10 ml of 1M NaOH (final pH 10). The layers were separated and the aqueous fraction was extracted a second time with 50 ml of methylene chloride. The combined organic layers were dried over $MgSO_4$ and filtered. The filter cake was washed with 50 ml of methylene chloride. The combined filtrates were concentrated in vacuo to give 700 mg of crude product. The crude product was purified by column chromatography (80 g silica gel, eluent-hexane/ethyl acetate 7/3). The fractions containing the purified product were combined and concentrated in vacuo to obtain 490 mg of the product protected as the diBOC derivative. To 200 mg of this diBOC derivative was added 4 ml of chloroform and 1 ml of TFA. The resulting reaction mixture was stirred at ambient temperature for 2 hr and concentrated in vacuo. The residue was dissolved in 25 ml of water and 25 mL of methylene chloride and adjusted to pH 10 with approximately 2 ml of concentrated ammonium hydroxide. The layers were separated and the aqueous layer was extracted a second time with 25 ml of methylene chloride. The organic fractions were combined, dried over $Na_2SO_4$ and concentrated in vacuo. The resulting residue was dissolved in 10 ml of diethyl ether, HCl gas was bubbled through the solution for 2 minutes and the solution was cooled at 4° C. overnight. The precipitated product was collected by filtration, washed with cold (4° C.) diethyl ether, and dried under vacuum to obtain 160 mg of the desired product in 67% yield.

Group IV Amphiphiles (A) 1-($N^4$-spermine)-2,3-dilaurylglycerol carbamate 1-($N^4$-spermine)-2,3-dilaurylglycerol carbamate (FIG. 7, No. 89) was prepared as follows. A solution of 3-benzyloxy-1,2-propanediol (1.00 g, 5.49 mmol) in THF (20 mL) was added to a suspension of sodium hydride (60% w/w in oil, 550 mg, 13.725 mmol) in THF (30 mL) and allowed to reflux overnight under dry nitrogen. A solution of dodecyl methane sulfonate (3.39 g, 12.078 mmol) in THF (20 mL) was added and the reaction was refluxed for another two days. After cooling to room temperature the reaction was filtered through a bed of Celite, rinsing with THF. The filtrate was reduced in vacuo to a yellow oil which was redissolved in diethyl ether (100 mL). The ether solution was washed with 0.1 N NaOH (30 mL) and dH2O (2×30 mL). The organic layer was dried over magnesium sulfate, filtered and reduced in vacuo to a red-brown oil. The crude material was purified by flash column chromatography (300 g silica gel) eluting with 3% ethyl acetate/hexanes. The desired product was isolated as a pale yellow oil and characterized by $^1$H NMR as 3-OBn-1,2-dilaurylglycerol (1.70 g, 60%). 3-OBn-1,2-dilaurylglycerol (1.70 g, 3.28 mmol) in ethanol (100 mL) was stirred with 10% Pd/C (250 mg, 15 wt %) under a hydrogen atmosphere for 24 hours. The reaction was flushed with nitrogen and filtered through Celite, rinsing with ethanol, to remove the catalyst. The filtrate was reduced in vacuo to a solid. The crude material was purified by flash column chromatography (140 g silica gel) eluting with 10% ethyl acetate/hexanes. The desired product was isolated as a white solid and characterized by $^1$H NMR as 1,2-dilaurylglycerol (1.23 g, 88%).

A 1.93 M solution of phosgene in toluene (0.77 mL, 1.49 mmol) was added to a solution of 1,2-dilaurylglycerol (580 mg, 135 mmol) and N,N-diisopropylethylamine (0.26 mL, 1.49 mmol) in methylene chloride (10 mL) and stirred overnight. A solution of $N^1,N^{12}$-di-CBz-spermine•2HCl (734 mg, 1.35 mmol) in 60:25:4 chloroform/methanol/water (80 mL) was added. After 3 hours another equivalent of N,N-diisopropylethylamine (0.26 mL, 1.49 mmol) was added. An additional 0.5 equivalents of N,N-diisopropylethylamine (0.13 mL, 0.75 mmol) was added three hours later and the reaction was allowed to stir overnight under nitrogen at ambient temperature. The reaction was washed with 1M NaOH (20 mL) and dH2O (15 mL). The organic layer was separated, dried over magnesium sulfate, filtered and reduced in vacuo to a white solid. The crude material was purified by flash column chromatography (125 g silica gel) eluting with 90:10:0.5 chloroform/methanol ammonium hydroxide. The desired product was isolated as an oil and characterized by $^1$H NMR as 1-($N^4$-($N^1,N^{12}$-di-CBz-spermine))-2,3-dilaurylglycerol carbamate (188 mg, 15%).

The 1-($N^4$-($N^1,N^{12}$-di-CBz-spermine)-2,3-dilaurylglycerol carbamate (188 mg, 0.203 mmol) was dissolved in glacial acetic acid (10 mL) and stirred with 10% Pd/C (45 mg, 24 wt %) under a hydrogen atmosphere for 5 hours. The catalyst was removed by vacuum filtration rinsing with 10% acetic acid/ethyl acetate (10 mL). The filtrate was reduced to an oil by rotary evaporation. The resulting oil was dissolved in 10% methanol/chloroform (85 mL) and was washed with 1M NaOH (15 mL) and dH2O (10 mL). The organic layer was separated, dried over magnesium sulfate, filtered and reduced in vacuo to an oil. The product was characterized by $^1$H NMR as 1-($N^4$-spermine)-2,3-dilaurylglycerol carbamate (125 mg, 94%).

Other amphiphiles of the invention may be prepared according to procedures that are within the knowledge of those skilled in art.

EXAMPLES

The following Examples are representative of the practice of the invention.

Example 1

Cell Transfection Assay

Separate 3.35 μmole samples of spermidine cholesterol carbamate (amphiphile No. 53) and the neutral lipid dioleoylphosphatidylethanolamine ("DOPE") were each dissolved in chloroform as stock preparations. Following combination of the solutions, a thin film was produced by removing chloroform from the mixture by evaporation under reduced pressure (20 mm Hg). The film was further dried under vacuum (1 mm Hg) for 24 hours. As aforementioned, some of the amphiphiles of the invention participate in transacylation reactions with co-lipids such as DOPE, or are subject to other reactions which may cause decomposition thereof. Accordingly, it is preferred that amphiphile/co-lipid compositions be stored at low temperature, such as −70 degrees C., until use.

To produce a dispersed suspension, the lipid film was then hydrated with sterile deionized water (1 ml) for 10 minutes, and then vortexed for 1 minute (sonication for 10 to 20 seconds in a bath sonicator may also be used, and sonication has proved useful for other amphiphiles such as DC-chol). The resulting suspension was then diluted with 4 ml of water to yield a solution that is 670 $\mu$M in cationic amphiphile and 670 $\mu$M in neutral colipid.

Experiments were also performed using spermine cholesterol carbamate (amphiphile No. 67) and other amphiphiles of the invention. With respect to spermine cholesterol carbamate, the optimum molar ratio of amphiphile to DOPE under the conditions tested was determined to be 1:2, not 1:1. Optimized ratios for many of the amphiphiles of the invention are reported in FIGS. 13, 14 and 15, and are readily determined by those skilled in the art.

For preparation of the transfecting solution, DNA encoding for $\beta$-galactosidase (pCMV$\beta$, ClonTech., Palo Alto, Calif.) was dissolved in OptiMEM culture medium (Gibco/BRL No. 31885-013). The resulting solution had a DNA concentration of 960 $\mu$M (assuming an average molecular weight of 330 daltons for nucleotides in the encoding DNA).

The following procedure was used to test a 1:1 molar mixture of the cationic amphiphile spermidine cholesterol carbamate in combination with DOPE. A 165 $\mu$l aliquot of spermidine cholesterol carbamate (670 $\mu$M) containing also the co-lipid (at 670 $\mu$M ) was pipetted into 8 separate wells in a 96-well plate containing OptiMEM (165 $\mu$l) in each well. The resulting 335 $\mu$M solutions were then serially diluted 7 times to generate 8 separate amphiphile-containing solutions having concentrations ranging from 335 $\mu$M to 2.63 $\mu$M, with each resultant solution having a volume of 165 $\mu$l. Thus, 64 solutions were prepared in all, there being 8 wells each of 8 different concentrations of amphiphile/DOPE.

Independently, DNA solutions (165$\mu$l, 960 $\mu$M) were pipetted into 8 wells containing OptiMEM (165 $\mu$l), and the resulting 480 $\mu$M solutions were then serially diluted 7 times to generate 8 separate 165 $\mu$l solutions from each well, with the concentrations of DNA in the wells ranging from 480 $\mu$M to 3.75 $\mu$M.

The 64 test solutions (cationic amphiphile: neutral lipid) were then combined with the 64 DNA solutions to give separate mixtures in 64 wells, each having a volume of 330 $\mu$l, with DNA concentrations ranging from 240 $\mu$M to 1.875 $\mu$M along one axis, and lipid concentrations ranging from 167 $\mu$M to 1.32 $\mu$M along the other axs. Thus 64 solutions were prepared in all, each having a different amphiphile: DNA ratio and/or concentration. The solutions of DNA and amphiphile were allowed to stand for 15 to 30 minutes in order to allow complex formation.

A CFT-1 cell line (human cystic fibrosis bronchial epithelial cells immortalized with papillomavirus) provided by Dr. James Yankaskas, University of North Carolina, Chapel Hill, was used for the in vitro assay. The cells are homozygous for a mutant allele (deletion of phenylalanine at position 508, hereinafter $\Delta$ F508 ) of the gene encoding for cystic fibrosis transmembrane conductance regulator ("CFTR") protein. CFTR is a cAMP-regulated chloride (Cl$^-$) channel protein. Mutation of the CFTR gene results typically in complete loss for at least substantial impairment) of Cl$^-$ channel activity across, for example, cell membranes of affected epithelial tissues.

The $\Delta$ F508 mutation is the most common mutation associated with cystic fibrosis disease. For a discussion of the properties of the $\Delta$ F508 mutation and the genetics of cystic fibrosis disease see, in particular, Cheng et al., *Cell*, 63, 827–834 (1990). See also Riordan et al., *Science*, 245, 1066–1073 (1989); published European Patent Application No. 91301819.8 of Gregory et al., bearing publication number 0 446 017 A1; and Gregory et al., *Nature*, 347, 382–385 (1990).

The cells were cultured in Hams F12 nutrient media (Gibco/BRL No. 31765-027) supplemented with 2% fetal bovine serum ("FBS", Irvine Scientific, No. 3000) and 7 additional supplements. Cells were then plated into 96-well tissue culture plates at a density of approximately 7,500 cells/well. Before being used in the assay, cells were allowed to grow for periods of 5–7 days until a confluent pattern had been achieved.

Following the allotted time period, three 96-well plates with CFT-1 cells were aspirated in order to remove the growth medium. The various concentrations of DNA-lipid complex (in 100 $\mu$l aliquots) were transferred to each of three 96-well plates bringing the DNA-lipid complexes in contact with the cells. DNA-only/cell and lipid-only/cell control wells were also prepared on one of the three plates.

The 100 $\mu$l solutions of DNA-lipid complex were maintained over the cells for 6 hours, after which 50 $\mu$l of 30% FBS (in OptiMEM) was added to each well. After a further 20-hour incubation period, an additional 100 $\mu$l of 10% FBS in OptiMEM was also added. Following a further 24-hour incubation period, cells were assayed for expression of protein and $\beta$-galactosidase.

For the assays, the resultant medium was removed from the plates and the cells washed with phosphate buffered saline. Lysis buffer (50 $\mu$l, 250 mM Tris-HCl, pH 8.0,0.15% Triton X-100) was then added, and the cells were lysed for 30 minutes. The 96-well plates were carefully vortexed for 10 seconds to dislodge the cells and cell debris, and 5 $\mu$l volumes of lysate from each well were transferred to a plate containing 100 $\mu$l volumes of Coomassie Plus® protein assay reagent (Pierce Company, No. 23236). The protein assay plates were read by a Bio-Rad Model 450 plate-reader containing a 595 nm filter, with a protein standard curve included in every assay.

The level of $\beta$-galactosidase activity in each well was measured by adding phosphate buffered saline (50 $\mu$l) to the remaining lysates, followed by addition of a buffered solution consisting of chlorophenol red galactopyranoside (100 $\mu$l, 1 mg per ml, Calbiochem No. 220588), 60 mM disodium hydrogen phosphate pH 8.0, 1 mM magnesium sulfate, 10 mM potassium chloride, and 50 mM 2-mercaptoethanol. The chlorophenol red galactopyranoside, following enzymatic ($\beta$-galactosidase) hydrolysis, gave a red color which was detected by a plate-reader containing a 570 nm filter. A$\beta$galactosidase (Sigma No. G6512) standard curve was included to calibrate every assay.

Following subtraction of background readings, optical data determined by the plate-reader allowed determination of $\beta$-galactosidase activity and protein content. In comparison to the amount of $\beta$-galactosidase expressed by known transfectants, for example, DME (1,2-dimyristyloxypropyl-3-diethyl-hydroxyethyl ammonium bromide), compounds of the invention are particularly effective transfecting airway epithelial cells and inducing therein $\beta$-galactosidase expression. Relative to DMRIE:DOPE (1:1), the spermidine cholesterol carbamate: DOPE mixture (also 1:1) demonstrated transfection efficiency improved by a factor of about 5 (see, for example, FIGS. 13, 14 and 15).

Example 2
Transfection of the Gene Encoding for Human Cystic Fibrosis Transmembrane Conductance Regulator Protein The ability of the cationic amphiphiles of the invention to transfect cells and to induce therein biochemical corrections was demonstrated with a separate in vitro assay. Immortalized human cystic fibrosis airway cells (CFT-1, as above) were used.

In preparation for the assay, the cells were grown on glass coverslips until approximately 60% confluent The cells were hen transfected with a complex of spermidine cholesterol carbamate:DOPE (1:1) and a plasmid(pCMV-CFTR) containing a cDNA that encodes wild type human CFTR pCMV-CFTR plasmid is a construct containing the encoding sequence for CFTR and the following regulatory elements, a CMV promoter and enhancer, and an SV40 polyadenylation signal. Additional constructs suitable for the practice of this example include pMT-CFTR, Cheng et al., *Cell*, 63,827–834 (1990). The complex used was 10.5 μmolar of spermidine cholesterol carbamate (also of DOPE) and 30 μmolar of pCMV-CFTR based on nucleotide.

48 hours after amphiphile-mediated transfection, cells were tested for cAMP-stimulated Cl⁻ channel activity using the 6-methoxy-N-(3-sulfopropyl)quinolinium ("SPQ") assay. See S. Cheng et al., *Cell*, 66,1027–1036 (1991) for further information concerning assay methodology. In the assay, cAMP-dependent Cl⁻ channel activity was assessed using "SPQ" (from Molecular Probes, Eugene, Oreg.), a halide-sensitive fluorophore. Increases in halide permeability results in a more rapid increase in SPQ fluorescence, and the rate of change (rather than the absolute change in fluorescence) is the important variable in assessing Cl⁻ permeability. See also Rich et al., *Nature*, 347, 358–363 (1990) for background information.

Fluorescence of the SPQ molecule in individual cells was measured using an inverted microscope, Nikon, a digital imaging system from Universal Imaging, and an ICCD camera, Hamamatsu, Inc. Cells were selected for analysis without prior knowledge of their expected rate-of-change-in-fluorescence characteristics.

In each experiment, up to five microscope fields of between 90 and 100 cells were examined on a given day, and studies under each condition were repeated on at least 3 different days. Since expression of CFTR is heterogenous (i.e. cells do not produce identical amounts of CFTR), the data presented were for the 20% of cells in each field exhibiting the greatest response.

As expected, cells that were mock transfected failed to exhibit any measurable increase in cAMP-stimulated halide fluorescence. In contrast, cells that had been transfected with the wild type CFTR cDNA displayed a rapid increase in SPQ fluorescence upon stimulation with cAMP agonist, indicating increased permeability to anions. Approximately 60% of the cells assayed exhibited measurable cAMP-stimulated Cl⁻ channel activity. Accordingly, spermidine cholesterol carbamate, and other cationic amphiphiles of the invention similarly tested, are effective in transferring CFTR-encoding plasmid into immortalized CF airway cells.

Example 3
CAT Assay
Part A

This assay was used to assess the ability of the cationic amphiphiles of the invention to transfect cells in vivo from live specimens. In the assay, the lungs of balb/c mice were instilled intra-nasally (the procedure can also be performed trans-tracheally) with 100 μl of cationic amphiphile:DNA complex, which was allowed to form during a 15-minute period prior to administration according to the following procedure. The amphiphile (premixed with co-lipid, see below) was hydrated in water for 10 minutes, a period sufficient to yield a suspension at twice the final concentration required. This was vortexed for two minutes and aliquoted to provide 55 microliter quantities for each mouse to be instilled. Similarly, DNA encoding the reporter (CAT) gene was diluted with water to a concentration twice the required final concentration, and then aliquoted at 55 microliters for each mouse to be instilled. The lipid was gently combined with the DNA (in a polystyrene tube), and the complex allowed to form for 15 minutes before the mice were instilled therewith.

The plasmid used (pCMVHI-CAT, see Example 4) provides an encoding DNA for chloramphenicol transferase enzyme. Specifics on the amphiphile:DNA complexes are provided below.

Two days following transfection, mice were sacrificed, and the lungs and trachea removed, weighed, and homogenized in a buffer solution (250 mM Tris, pH 7.8, 5 mM EDTA). The homogenate was darifed by centrifugation, and the deacetylases therein were inactivated by heat treatment at 70° C. for 10 minutes. Lysate was incubated overnight with acetyl coenzyme A and $C^{14}$-chloramphenicol. CAT enzyme activity was then visualized by thin layer chromatography ("TLC") following an ethyl acetate extraction. Enzyme activity was quantitated by comparison with a CAT standard curve.

The presence of the enzyme CAT will cause an acetyl group to be transferred from acetyl coenzyme A to $C^{14}$-chloramphenicol. The acetylated/radiolabeled chloramphenicol migrates faster on a TLC plate and thus its presence can be detected. The amount of CAT that had been necessary to generate the determined amount of acetylated chloramphenicol can then be calculated from standards.

Figure 10:
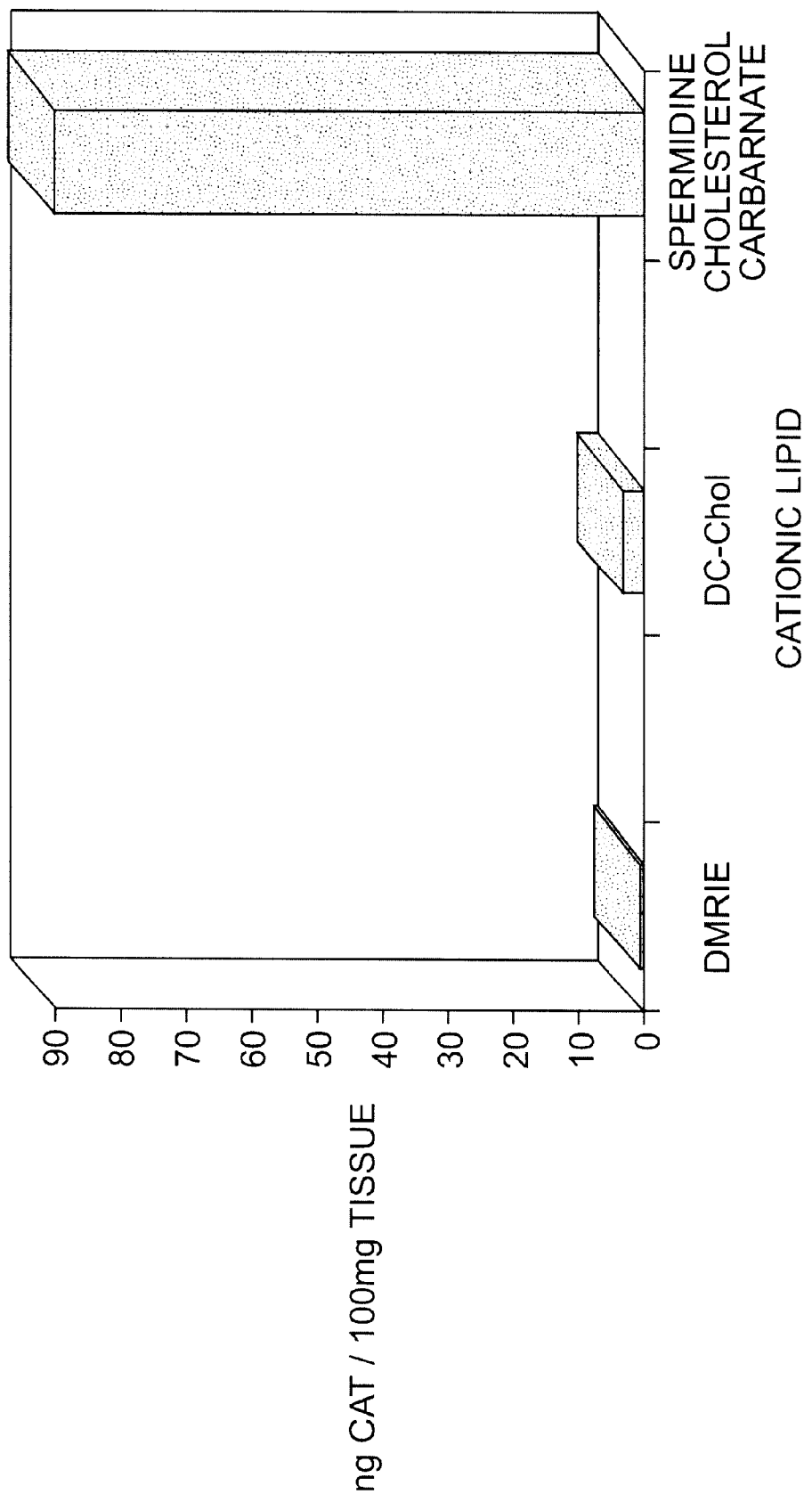
FIG. 10 provides a comparison of in vivo transfection efficiency for certain cationic amphiphiles under particular conditions.

The activity of spermidine cholesterol carbamate (amphiphile No.53) was determined in the CAT assay in relation to the recognized transfection reagents DMRIE and DC-Chol. FIG. 10 demonstrates dramatically (as ng CAT activity per 100 mg tissue) the enhanced ability of spermidine cholesterol carbamate (amphipile No. 53) to transfect cells in vivo, which enhancement is about 20-fold, or greater, in this assay. In the assay, activity was measured as ng CAT enzyme per 100 mg lung tissue. As a comparison, it is generally observed that DMRIE, a well known transfectant, when prepared as a 1:1 molar mixture with DOPE and then complexed with plasmid DNA (1.7 mM DMRIE, 1.7 mM DOPE, 1.2 mM plasmid DNA measured as nucleotide) gives about 1 to 2 ng activity per 100 mg lung tissue in this assay.

With respect to the comparison provided by FIG. 10, the following conditions are of note. The transfection solution for spermidine cholesterol carbamate contained 6 mM DNA measured as concentration of nucleotide, and 1.5 mM of cationic amphiphile. Following generally the procedure of Example 1, each amphiphile had also been premixed with DOPE, in this case at 1:1 molar ratio. For transfection with DC-chol, the molar ratio of DC-chol to DOPE was 3:2, and the concentrations of cationic amphiphile and of DNA (as nucleotide) were 1.3 mM and 0.9 mM, respectively. For transfection with DMRIE, the molar ratio of DMRIE to DOPE was 1:1 and the concentrations of cationic amphiphile and of DNA were 1.7 mM and 12 mM, respectively. These concentrations (and concentration ratios) for each amphiphile, and co-lipid and DNA, had been determined to be optimal for transfection for that respective amphiphile, and accordingly were used as the basis for the comparison presented herein.

Figure 11:
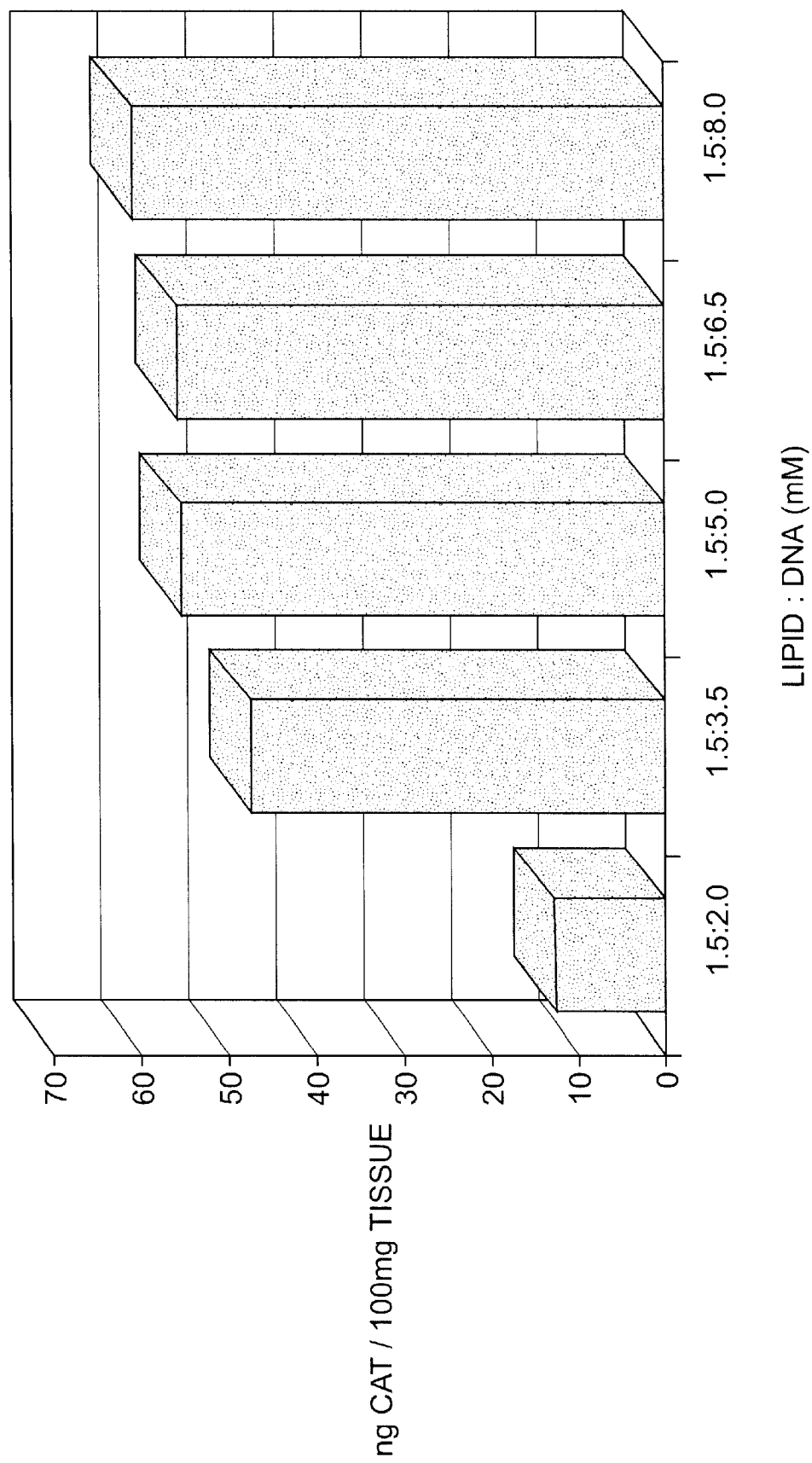
FIG. 11 is a depiction of in vivo transfection efficiency as a function of DNA concentration for a particular cationic amphiphile.
Figure 12:
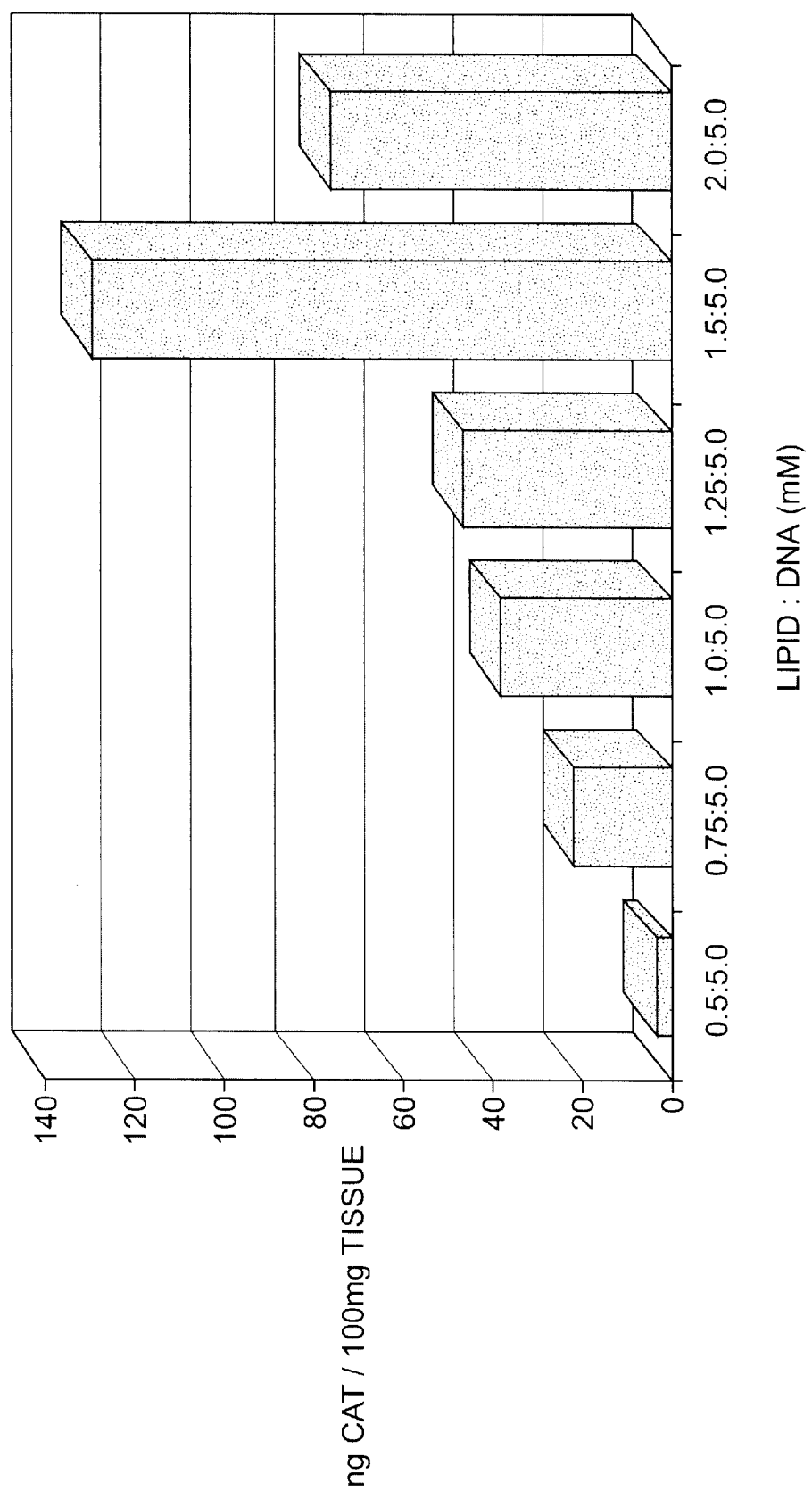
FIG. 12 is a depiction of in vivo transfection efeciency as a function of concentration of a particular cationic amphiphile.

For spermidine cholesterol carbamate (amphiphile No. 53), optimization experiments were also performed to determine preferred concentrations of plasmid for a particular amphiphile concentration (see FIG. 11), and also to determine preferred concentrations of the same amphiphile in relation to a particular plasmid concentration (see FIG. 12). Transfection efficiency was optimal at an amphiphile concentration of 1.5 mM (DOPE also being present at 1.5 mM); and about 6 mM (by nucleotide) of plasmid, or about at a ratio of 1:4. It was noted, however, that concentrations of about 0.75 mM of amphiphile, and 3.0 mM of plasmid were less toxic to the target cells.

Intra-nasal transfection with pCMVHI-CAT vector was also performed in mice using spermidine cholesterol carbamate as cationic amphiphile but with cholesterol as co-lipid In this experiment, the concentrations of spermidine cholesterol carbamate tested were between 1.0 and 1.5 mM (cholesterol being present at a 1:1 molar ratio in each case, with the mixing of amphiphile and co-lipid being performed as above). The DNA concentration (measured as nucleotide concentration) was between 4.0 and 6.0 mM. Transfection efficiency (again measured as ng CAT/100 mg tissue) was less effective than with DOPE as co-lipid; however, the transfections were substantially more effective than those achieved using DC-Chol/DOPE.

Part B

Figure 1B:
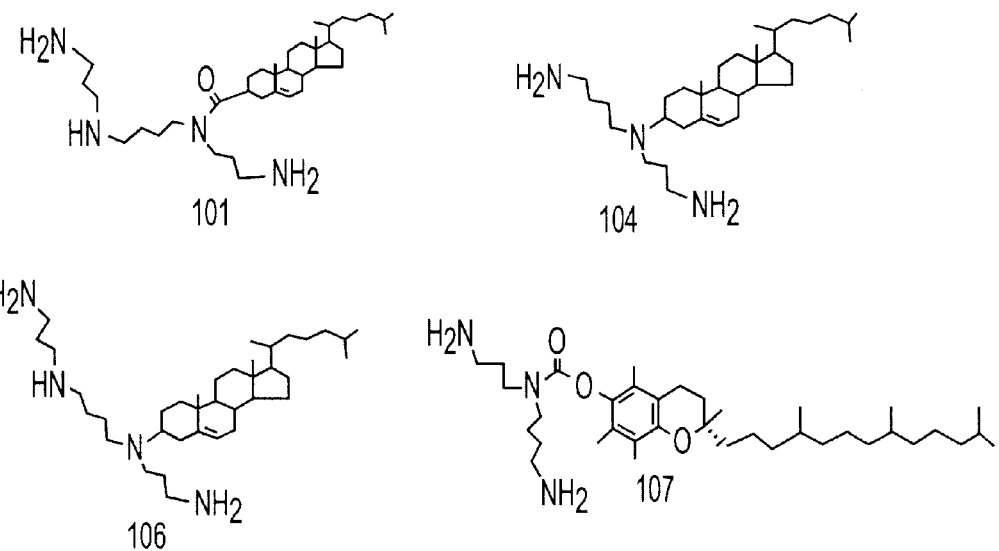
Figure 1C:
Figure 5:
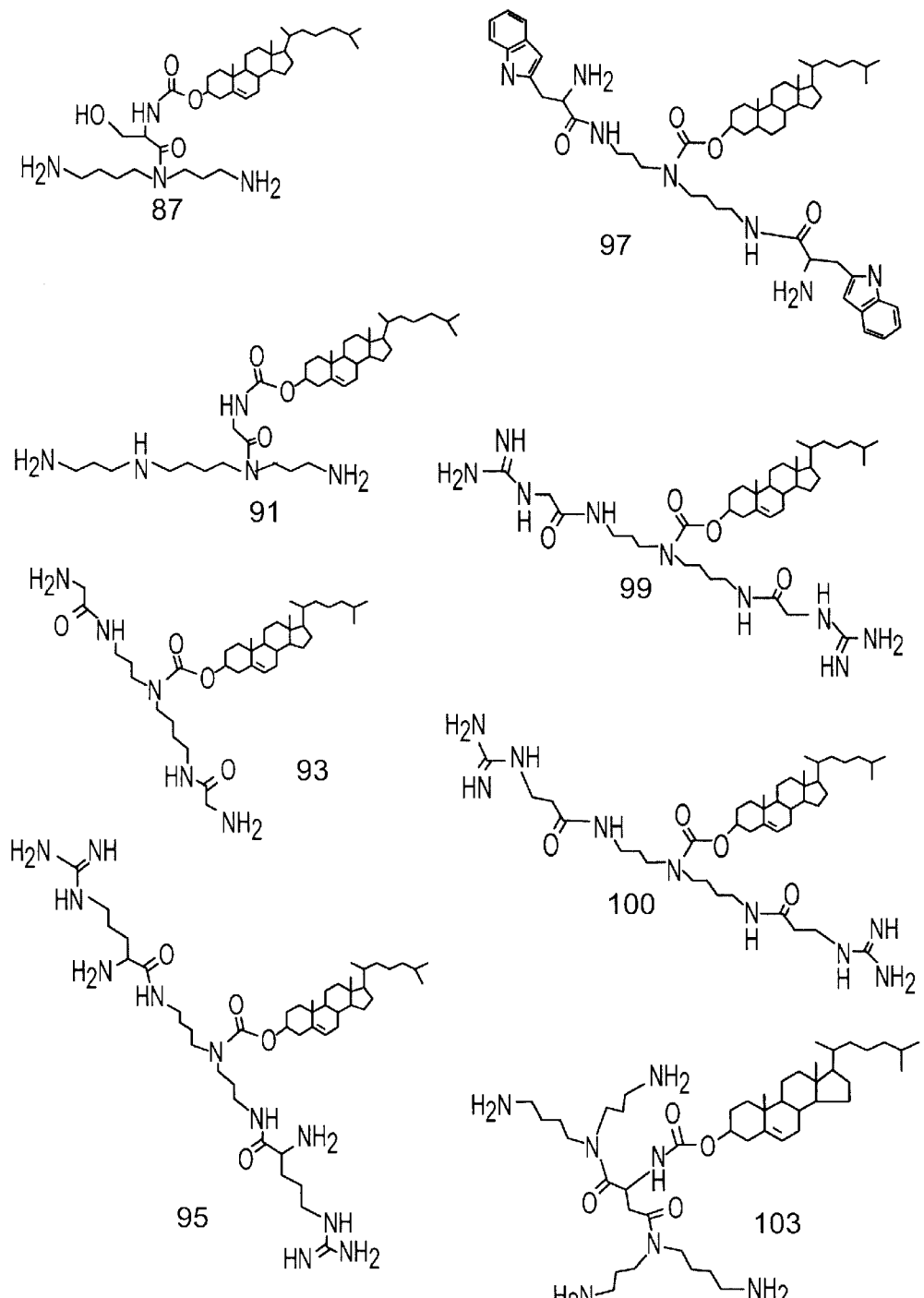
FIG. 5 depicts represenative Group II cationic amphiphiles.
Figure 7:
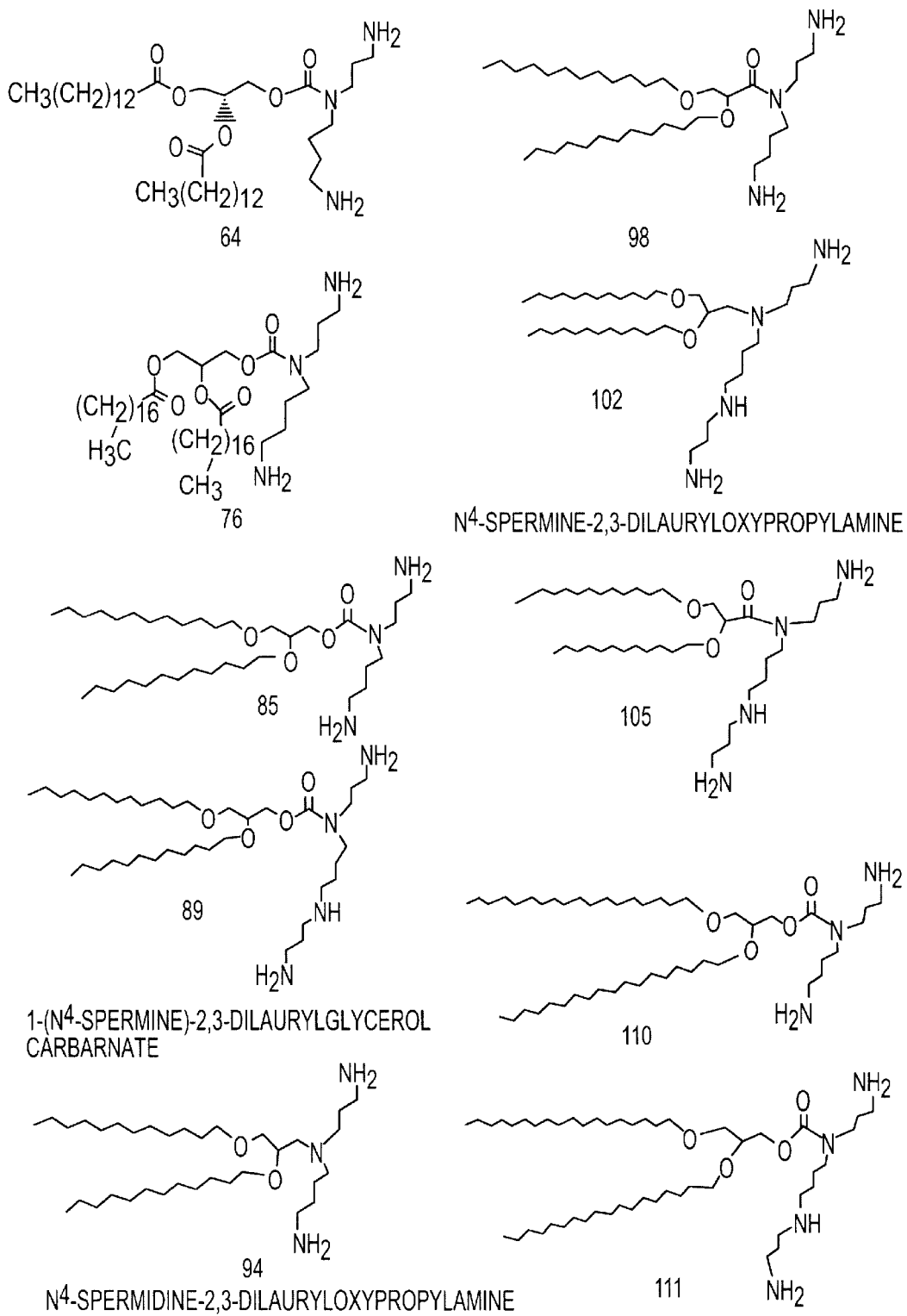
FIG. 7 depicts representative Group IV cationic amphiphiles.

Additional experiments were performed to compare in vivo the transfection efficiency of cationic amphiphiles depicted in FIGS. 1, 5 and 7. Results therefor are reported in FIGS. 13, 14 and 15 respectively. The compounds were administered intra-nasally using between 12 and 15 mice per compound. As in part A above, ng CAT activity was measured per 100 mg of tissue. However, improved vectors (pCF1/CAT and its near equivalent pCF2/CAT) were used. In part resulting from improved vector performance, incubations of lysate with acetyl coenzyme A and $C^{14}$-chloramphenicol were conducted for only 30 minutes. Construction of pCF1/CAT and pCF2/CAT is described below in Example 4.

The in vivo data reported in FIGS. 13, 14 and 15 were compiled generally as follows. As aforementioned, FIGS. 10 and 11 report data from the complete in vivo optimization of amphiphile No. 53. Amphiphile No. 67 was subjected to a similar partial optimization. With respect to all of the other cationic amphiphiles reported on, and taking advantage of numerous structural similarities, optimized compositions for in vivo testing were extrapolated from in vitro results. This facilitated the screening of large numbers of amphiphiles and produced broadly, if not precisely, comparable data. For all amphiphiles other than Nos. 53 and 67, the ratio, for in vivo testing, of amphiphile concentration to DOPE concentration was taken from the in vitro experiments, as was the optimized ratio of amphiphile concentration to DNA concentration (see Example 1). Accordingly, for such amphips the in vivo test concentration was fixed at 1 mM, thereby fixing also the co-lipid concentration. [Broadly, the molar ratio of the amphiphile to co-lipid DOPE ranged from 1:2 (for example, spermine cholesterol carbamate, No. 67) through 1:1 (for example, spermidine cholesterol carbamate, No. 53) to about 2:1 (for example, amphiphile No. 75)]. The concentration of plasmid DNA vaned for each amphiphile species tested in order to duplicate the optimized amphiphile/DNA ratio that had been determined in vitro.

Part C

That the novel amphiphiles of the invention are an important contribution to the art is immediately seen by comparing their performance—as in vivo transfection enhancers—to that of closely related cationic amphiphiles that lack the novel T-shape. It has been determined that spermidine cholesterol carbamate provides a much greater level of enhancement than $N^1$-spermidine cholesteryl carbamate which contains the same number of carbon and nitrogen atoms in its cationic alkylamine component but which is linear and not "T-shaped". Following generally the procedures of Example 3, part B, and using respectively 6 mM (as nucleotide), 1.5 mM, and 1.5 mM concentrations of DNA, amphiphile and of co-lipid, the transfection enhancement provided by spermidine cholesterol carbamate (amphiphile No.53), in relation to $N^1$-spermidine cholesteryl carbamate, was determined to be about 30 fold.

Also following the procedures of Example 3, part B, and using respectively 4 mM (as nucleotide), 1 mM, and 2 mM concentrations of DNA, amphiphile and of co-lipid, the transfection enhancement provided by spermine cholesterol carbamate (amphiphile No. 67)—in relation to $N^1$-thermospermine cholesteryl carbamate and $N^1$-spermine cholesteryl carbamate to which spermine cholesterol carbamate is similarly related—is at least about 30 fold.

Example 4

Construction of Vectors

As aforementioned, numerous types of biologically active molecules can be transported into cells in therapeutic compositions that comprise one or more of the cationic amphiphiles of the invention. In an important embodiment of the invention, the biologically active macromolecule is an encoding DNA. There follows a description of novel vectors (plasmids) that are preferred in order to facilitate expression of such encoding DNAs in target cells.

Part A—pCMVHI-CAT pCMVHI-CAT is representative of plasmid constructs useful in the practice of the invention. Although the plasmid is provided in a form carrying a reporter gene (see Example 3), transgenes having therapeutic utility may also be included therein.

The pCMVHI-CAT vector is based on the commercially available vector pCMVβ (Clontech). The pCMVβ construct has a pUC19 backbone (J. Vieira, et al., *Gene*, 19, 259–268, 1982) that includes a procaryotic origin of replication derived originally from pBR322. Basic features of the pCMVHI-CAT plasmid (as constructed to include a nucleotide sequence coding for CAT) are as follows. Proceeding clockwise—the human cytomegalovirus immediate early gene promoter and enhancer, a fused tripartite leader from adenovirus and a hybrid intron, a linker sequence, the CAT cDNA, an additional linker sequence, the late SV40 polyadenylation signal, and the pUC origin of replication and backbone that includes the gene for ampicillin resistance.

The human cytomegalovirus immediate early gene promoter and enhancer spans the region from nucleotides 1–639. This corresponds to the region from –522 to +72 relative to the transcription start site (+1) and includes almost the entire enhance region from –524 to –118 as orginally defined by Boshart et al., Cell 41:521–530, 1985. The CAAT box is located at nucleotides 487–491 and the TATA box is at nucdeotides 522–526 in pCMVHI-CAT. The CAT transcript is predicted to initiate at nucleotide 549, which is the transcriptional start site of the CMV promoter. The tripartite leader-hybrid intron is composed of a fused tripartite leader from adenovirus containing a 5' splice donor signal, and a 3' splice acceptor signal derived from an IgG gene. The elements in the intron are as follows: the first leader, the second leader, part of the third leader, the splice donor sequence and intron region from the first leader, and the mouse immunoglobulin gene splice donor sequence. The length of the intron is 230 nucleotides. The CAT coding region comprises nucleotides 1257–1913. The SV40 poly A signal extends from nucleotide 2020 to 2249.

Accordingly, construction of the pCMVHI-CAT plasmid proceeded as follows. The vector pCMVβ (Clontech, Palo Alto, Calif.) was digested with Not I to excise the β-galactosidase gene. The vector fragment iacking the β-galactosidase gene was isolated and ligated to form pCMV.

Figure 17:
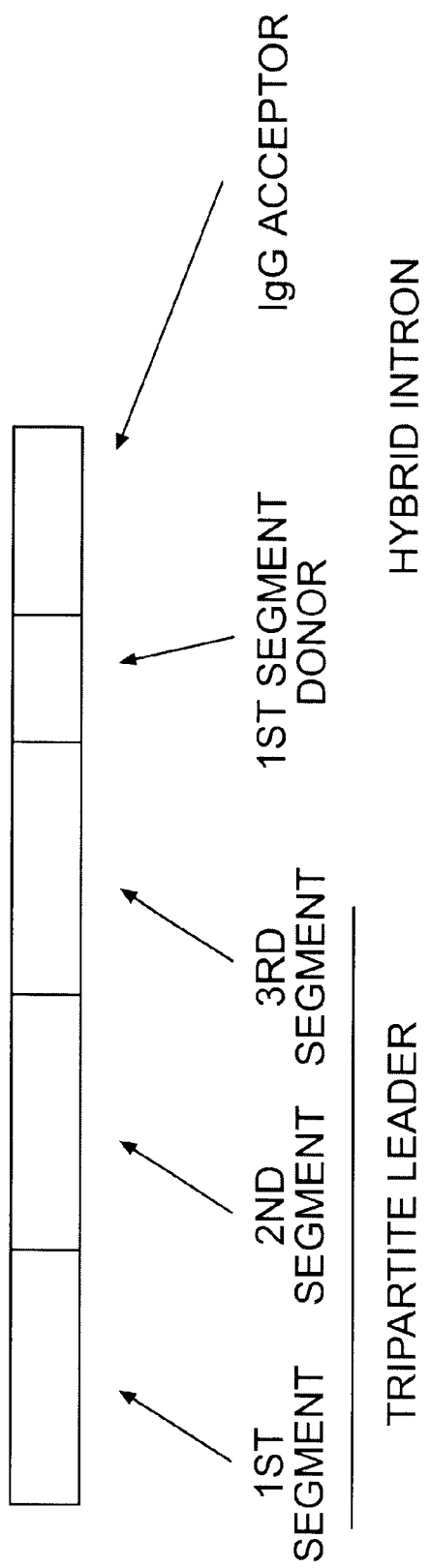
FIG. 17 shows the hybrid intron of pCMVHI-CAT.

The hybrid intron (FIG. 17) was obtained from the plasmid pADβ (Clontech). The hybrid intron had been isolated from a 695 base pair XhoI-EcoRI fragment of p91023(B), see Wong et al., *Science*, 228, 810–815 (1985). The hybrid intron contains the fused tripartite leader from adenovirus, the donor site from the first segment of the tripartite leader, and the acceptor site from an IgG gene, and has a length of 230 bp.

pADβ was digested with Pml I and Not I, and the ~500 base-pair (bp) fragment was isolated, and then ligated into the Not I site of pBluescriptII KS(–) (Stratagene, La Jolla, Calif.) to form pBlueII-HI.

pBlueII-HI was digested with XhoI and NotI to excise the hybrid intron fragment This fragment was ligated into the XhoI and NotI sites of pCMV, replacing the SV40 intron to form pCMVHI.

Figure 16:
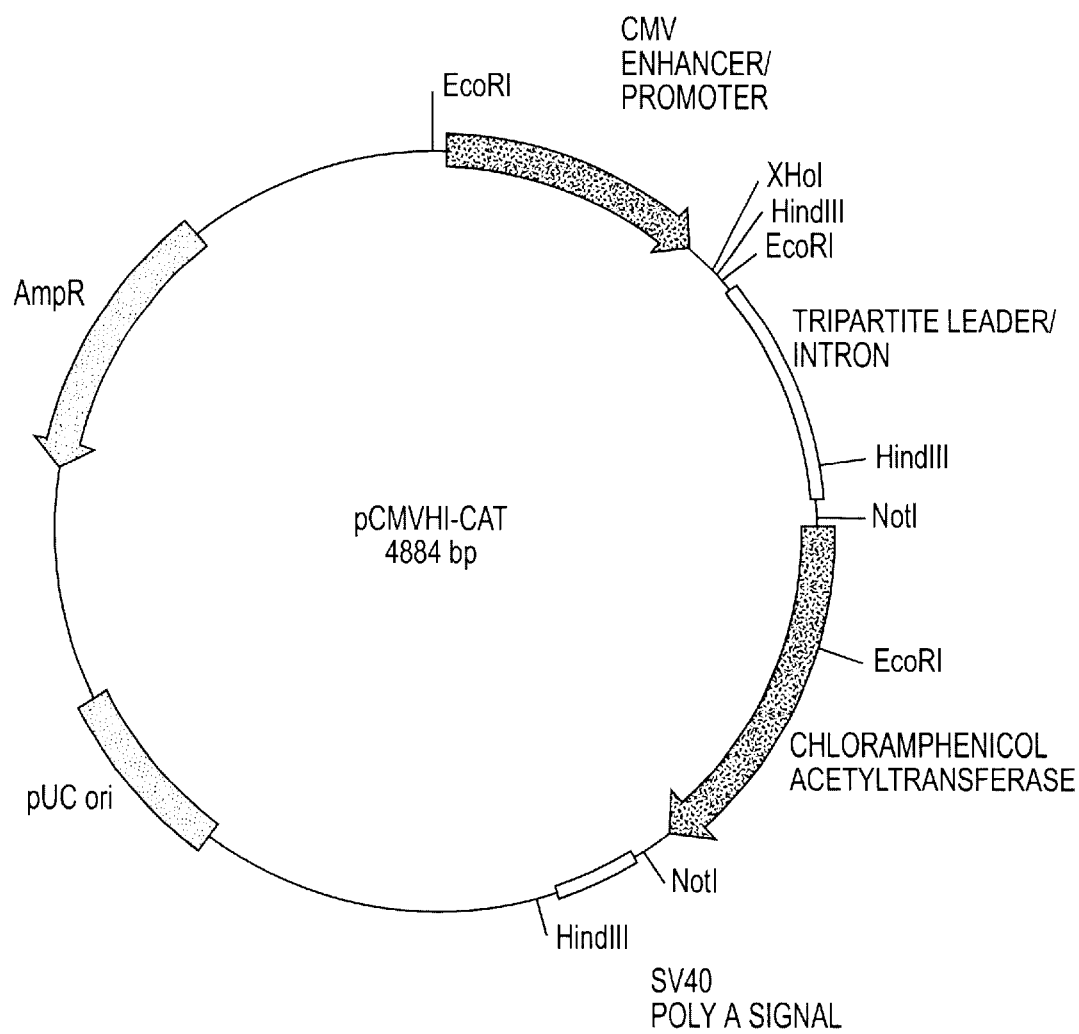
FIG. 16 provides a map of pCMVHI-CAT plasmid.

The CAT gene was obtained from the Chloramphenicol Acetyltransferase GenBlock (Pharmacia, Piscataway, N.J.). This 792 bp Hind III fragment was blunted with the klenow fragment of DNA Polymerase I, then Not I linkers (New England Biolabs) were ligated to each end. After digestion with Not I to expose the Not I sticky ends, the fragment was subc;oned into the Not I site of pCMV to form pCMV-CAT. pCMV-CAT was digested with Not I to excise the CAT fragment. The CAT fragment was ligated into pCMVHI to form pCMVHI-CAT which is depicted in FIG. 16.

Part B—pCF1 and pCF2

Figure 18A:
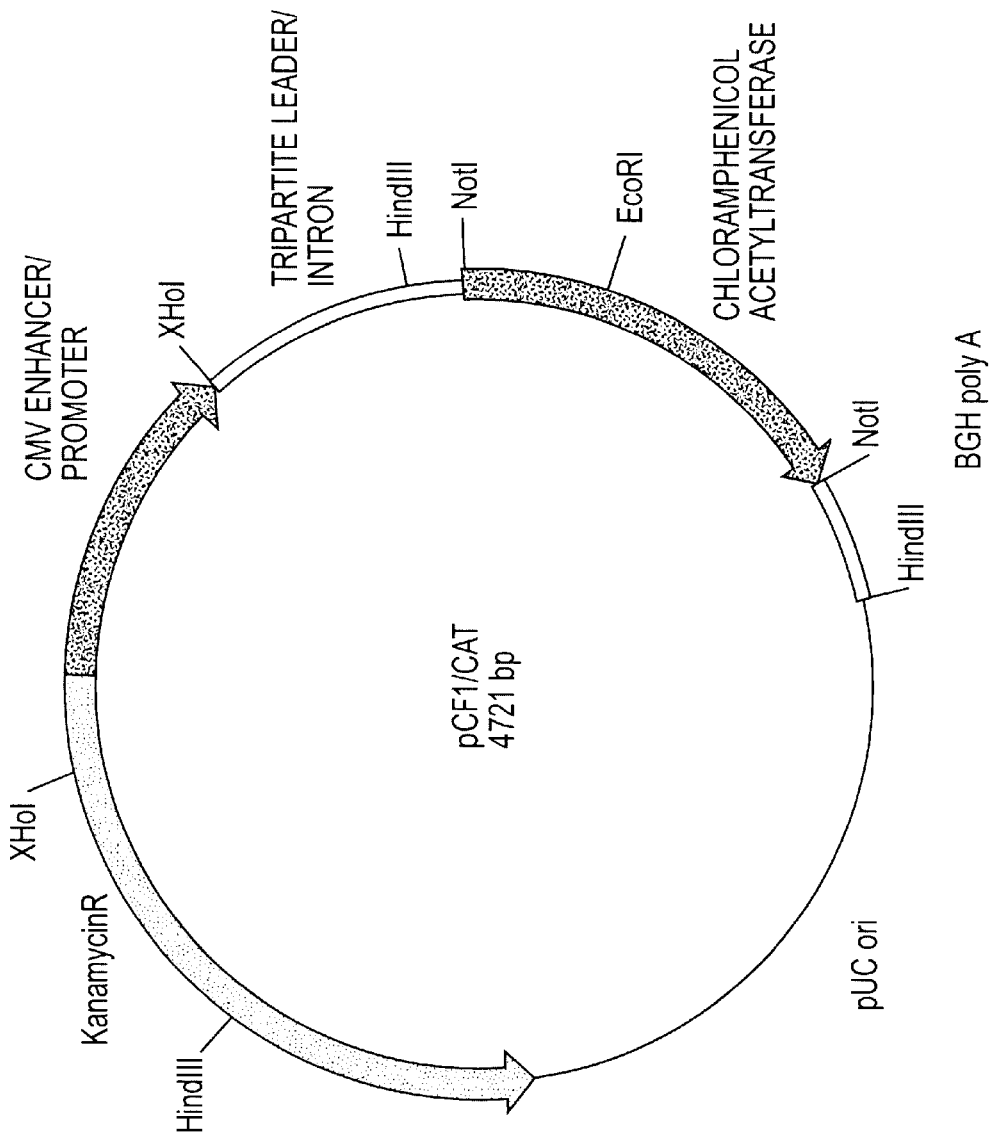
FIG. 18 (panel A) provides a map of pCF1/CAT plasmid.
Figure 18B:
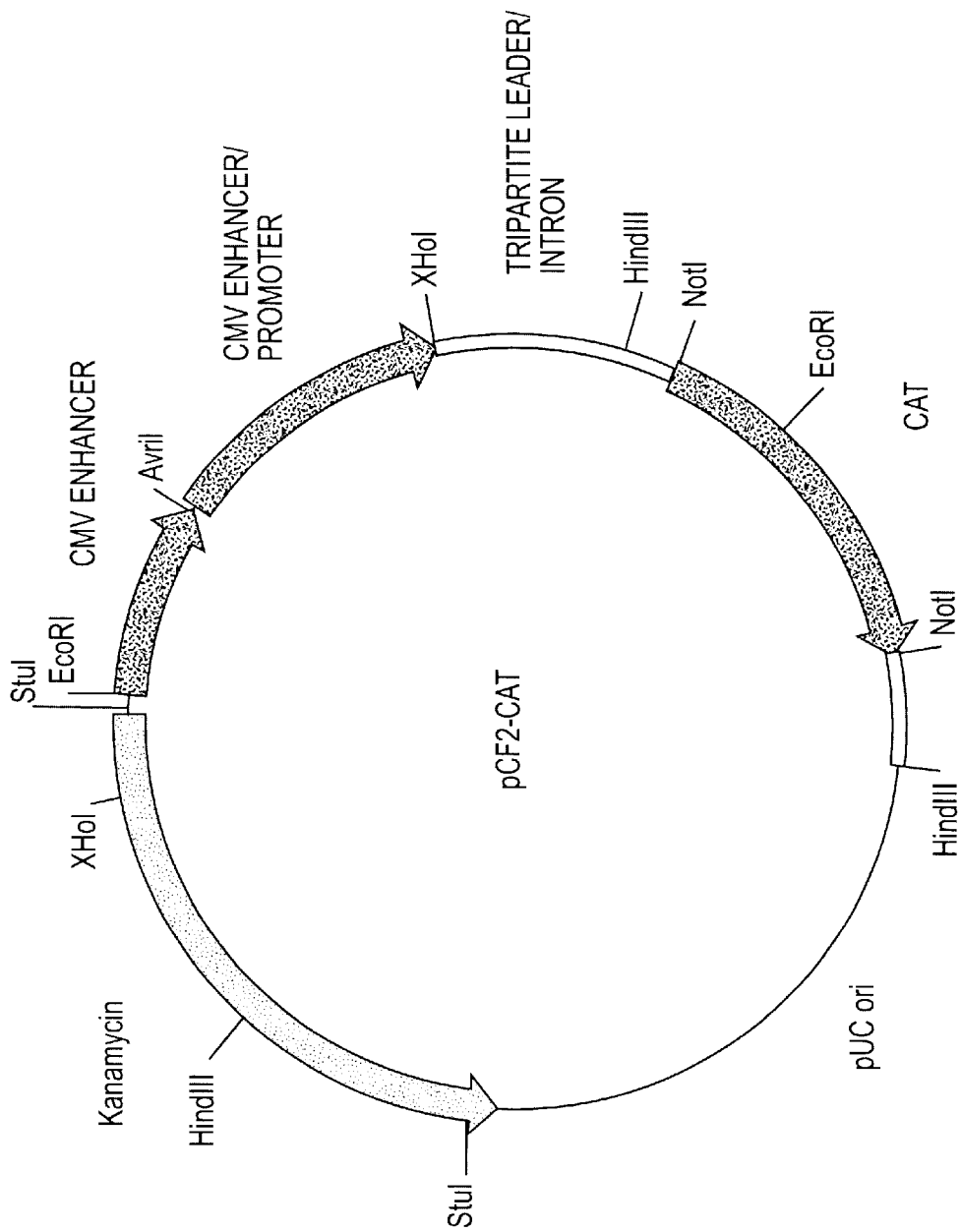

Although pCMVHI is suitable for therapeutic transfections, further performance enhancements (including increased expression of transgenes) are provided by the pCF1 and pCF2 plasmids. A map of pCF1/CAT is shown in FIG. 18, panel A, and a map of pCF2/CAT is shown in panel B.

Briefly, pCF1 contains the enhancer/promoter region from the immediate early gene of cytomegalovirus (CMV). A hybrid intron is located between the promoter and the transgene cDNA. The polyadenylation signal of the bovine growth hormone gene was selected for placement downstream from the transgene. The vector also contains a drug-resistance marker that encodes the aminoglycosidase 3'-phosphotransferase gene (derived from the transposon Tn903, A. Oka et al., *Journal of Molecular Biology*, 147, 217–226, 1981) thereby conferring resistance to kanamycin. Further details of pCF1 structure are provtded directly below, including description of placement therein of a cDNA sequence encoding for cystic fibrosis transmembrane conductance regulator (CFTR) protein.

The pCF1 vector is based on the commercially available vector PCMVβ (Clontech). The pCMVβ construct has a pUC19 backbone (J. Vieira, et al., *Gene*, 19, 259–268, 1982) that includes a procaryotic origin of replication derived originally from pBR322.

Basic features of the pCF1-plasmid (as constructed to include a nucleotide sequence coding for CFTR) are as follows. Proceeding clockwise—the human cytomegalovirus immediate early gene promoter and enhancer, a fused tripartite leader from adenovirus and a hybrid intron, a linker sequence, the CFTR cDNA, an additional linker sequence, the bovine growth hormone polyadenylation signal, pUC origin of replication and backbone, and the kanamycin resistance gene. The pCF1-CFTR plasmid has been completely sequenced on both strands.

The human cytomegalovirus immediate early gene promoter and enhancer spans the region from nucleotides 1–639. This corresponds to the region from –522 to +72 relative to the transcriptional start site (+1) and includes almost the entire enhancer region from –524 to –118 as origiay defined by Boshart et al., *Cell*, 41, 521–530 (1985). The CAAT box is located at nucleotides 486–490 and the TATA box is at nucleotides 521–525 in pCF1-CFTR. The CFTR transcript is predicted to initiate at nucleotide 548, which is the transcriptional start site of the CMV promoter.

The hybrid intron is composed of a fused tri-partite leader from adenovirus containing a 5' splice donor signal, and a 3' splice acceptor signal derived from an IgG gene. The elements in the intron are as follows: the first leader (nucleotides 705–745), the second leader (nucleotides 746–816), the third leader (partial, nucleotides 817–877), the splice donor sequence and intron region from the fist leader (nucleotides 878–1042), and the mouse immunoglobulin gene splice donor sequence (nucleotides 1043–1138). The donor site (G|GT) is at nucleotides 887–888, the acceptor site (AG|G) is at nucleotides 1128–1129, and the length of the intron is 230 nucleotides. The CFTR coding region comprises nucleotides 1183–5622.

Within the CFTR-encoding cDNA of pCF1-CFTR, there are two differences from the orginally-published predicted cDNA sequence (J. Riordan et al., *Science*, 245, 1066–1073, 1989); (1) an A to C change at position 1990 of the CFTR cDNA which corrects an error in the original published sequence, and (2) a T to C change introduced at position 936. The change at position 936 was introduced by site-directed mutagenesis and is silent but greatly increases the stability of the cDNA when propagated in bacterial plasmids (R. J. Gregory et al. et al., *Nature*, 347, 382–386, 1990). The 3' untranslated region of the predicted CFTR transit comprises 51 nucleotides of the 3' untranslated region of the CFTR cDNA, 21 nucleotides of linker sequence and 114 nucleotides of the BGH poly A signal.

The BGH poly A signal contains 90 nucleotides of flanking sequence 5' to the conserved AAUAAA and 129 nucleotides of flanking sequence 3' to the AAUAAA motif. The primary CFTR transcript is predicted to be cleaved downstream of the BGH polyadenylation signal at nucleotide 5808. There is a deletion in pCF1-CFTR at position +46 relative to the cleavage site, but the deletion is not predicted to effect either polyadenylation efficiency or cleavage site accuracy, based on the studies of E. C. Goodwin et al., *J. Biol. Chem.*, 267, 16330–16334 (1992). After the addition of a poly A tail, the size of the resulting transcript is approximately 5.1 kb.

pCF2 plasmid, FIG. 18 (B), contains a second CMV enhancer, in tandem with The first. Enhanced expression of transgenes from pCF1 or pCF2 results from the combination of a strong promoter, the presence of a highly efficient polyadenylation signal, a leader sequence that enhances translation, and an intron to increase message stability.

Example 5

Correction of Chloride Ion Transport Defect in Nasal Polyp Epithelial Cells of a Cystic Fibrosis Patient by Cationic Amphiphile-Mediated Gene Transfer Primary (non-immortalized) nasal polyp cells from an adult male cystic fibrosis patient (homozygous for the Δ F508mutation) were grown on collagen-coated permeable filter supports (Millicells) to form a polarized and confluent epithelial monolayer. Once the monolayer was electrically tight (about 5 to 7 days post seeding, and as indicated by the development of resistance across the cell sheet), the apical surface can be exposed to formulations of cationic amphiphile: DNA complex.

In this case, the amphiphile (spermidine cholesterol carbamate) was provided as a 1:1 (by mole) mixture with DOPE, and this mixture was then complexed with pCMV-CFTR plasmid vector (a construct encoding wild type human cystic fibrosis transmembrane conductance regulator protein, see above). Concentrations in the final mixture were 42 μmolar of spermidine cholesterol carbamate (and also of DOPE) and 60 μmolar (based on morality in nucleotides) of the plasmid expression vector.

Expression of CFTR was determined by measuring cAMP-stimulated transepithelial chloride secretion in a modified Ussing chamber, Zabner et al., *Nature Genetics*, 6, 75–83 (1984). The mucosal side of the epithelium was bathed in Ringer's bicarbonate solution bubbled with 95% $O_2$ and 5% $CO_2$. The composition of the submucosal solution was similar to the mucosal solution with the exception that sodium gluconate replaced sodium chloride. Transepithelial voltage was clamped to 0 m V and short circuit current was recorded. Amiloride (10 μM) was applied into the apical bath, followed by the mucosal addition of forskolin and IBMX (at 100 μM each). 5-nitro-2-(3-phenylpropylamino) benzoic acid ("NPPB"), an inhibitor of CFTR chloride charnels, was then added to the mucosal solution at 10 to 30 μM.

Figure 19A:
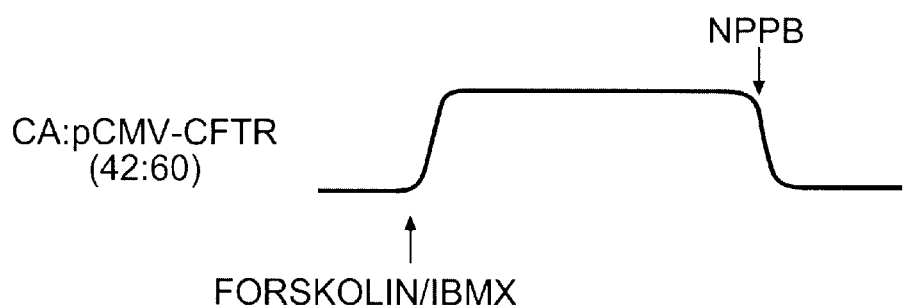
FIG. 19 (panel A) shows a plot of corrected chloride ion transport in PCMV-CFTR transfected nasal polyp epithelial cells from a cystic fibrosis patient.
Figure 19B:
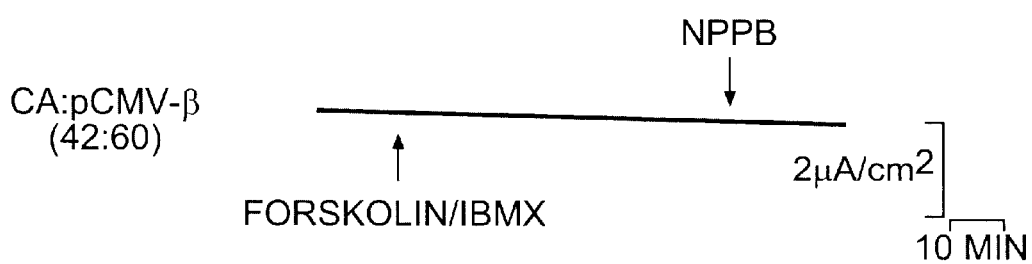

Chloride secretion (i.e. movement of chloride from the epithelial cells to the mucosal solution) is shown as an upward deflection (see FIG. 19A). The same plasmid vector, but containing a reporter gene, was used as a negative control (FIG. 19B). A cAMP-stimulated current (0.5 to 2.5 μampere/$cm^2$) was observed in monolayers transfected with wild type CFTR gene. Current was not detected with the pCMV-β-galactosidase control.

Example 6
Correction of Chloride Ion Transport Defect in Airway Epithelial Cells of a Cystic Fibrosis Patient by Cationic Amphiphile-Mediated Gene Transfer A recommended procedure for formulating and using the pharmaceutical compositions of the invention to treat cystic fibrosis in human patients is as follows.

Following generally the procedures described in Example 1, a thin film (evaporated from chloroform) is produced wherein spermine cholesterol carbamate (amphiphile No. 67) and DOPE are present in the molar ratio of 1:2. The amphiphile-containing film is rehydrated in water-for-injection with gentle vortexing to a resultant amphiphile concentration of about 3 mM. However, in order to increase the amount of amphiphile/DNA complex that may be stably delivered by aerosol as a homogeneous phase (for example, using a Puritan Bennett Raindrop nebulizer from Lenexa Medical Division, Lenexa, Kans., or the PARI LC Jet™ nebulizer from PARI Respiratory Equipment, Inc., Richmond, Va.), it may be advantageous to prepare the amphiphile-containing film to include also one or more further ingredients that act to stablize the final amphiphile/DNA composition. Accordingly, it is presently preferred to prepare the amphiphile-containing film as a 1:2:0.05 molar mixture of amphiphile No. 67, DOPE, and $PEG_{(5000)}$-DMPE. [A suitable source of PEG-DMPE, polyethylene glycol 5000-dimyristoylphoshatidyl ethanolamine, is Catalog No. 880210 from Avanti Polar Lipids, Alabaster, Ala.]. Additional fatty acid species of PEG-PE may be used in replacement therefor.

Without being lnimted as to theory, $PEG_{(5000)}$-DMPE is believed to stablize the therapeutric compositions by preventing further agrregation of formed amphiphile/DNA complexes. Additionally it is noted that $PEG_{(2000)}$-DMPE was found to be less effective in the practice of the invention.

pCF1-CFTR plasmid (containing an encoding sequence for human cystic fibrosis transmembrane conductance regulator, see Example 4) is provided in water-for-injection at a concentration, measured as nucleotide, of 4 mM. Complexing of the plasmid and amphiphile is then allowed to proceed by gentle contacting of the two solutions for a period of 10 minutes.

It is presently preferred to deliver aerosolized DNA to the lung at a concentration thereof of between about 2 and about 12 mM (as nucleotide). A sample of about 10 to about 40 ml is generally sufficient for one aerosol administration to the lung of an adult patient who is homozygous for the Δ F508 mutation in the CFTR-encoding gene.

It is expected that this procedure (using a freshly prepared sample of amphiphile/DNA) will need to be repeated at time intervals of about two weeks, but depending considerably upon the response of the patient, duration of expression from the transfected DNA, and the appearance of any potential adverse effects such as inflammation, all of which can be determined for each individual patient and taken into account by the patient's physicians.

One important advantage of the cationic amphiphiles of the present invention is that they are substantially more effective—in vivo—than other presently available amphiphiles, and thus may be used at substantially lower concertrations than known cationic amphiphiles. There results the opportunity to substantially mininize side effects (such as amphiphile toxicity, inflammatory response) that would otherwise affect adversely the success of the gene therapy.

A further particular advantage associated with use of many of the amphiphiles of the invention should again be mentioned. Many of the amphiphiles of the invention were designed so that the metabolism thereof would rapidly proceed toward relatively harmless biologically-compatible components. In this regard, highly active amphiphiles 53, 67, and 75 are of particular note.

Example 7
Further Enhancements in Plasmid Design for Gene Therapy: Replicating Episomal Plasmids Although the above design feature substantially enhance the performance of available plasmids, further modifications are desirable in order that therapeutic compositions comprising such plasmids and cationic amphiphiles have optimal performance for gene therapy.

It is desirable that plasmids for gene therapy also be able to replicate in the cells of patients, since continued presence of the plasmid will provide correction of the genetic defect (in the case of cystic fibrosis, lack of functioning CFTR protein in the cell membrane of lung epithelial cells or other cells) over an extended period of time. There is concern that plasmids representative of the current art (that is, those that cannot replicate in the targeted cells of a patient) may be degraded after only a relatively short period of maintenance in the patient, thus requiring excessive repeat administrations.

Long term correction could perhaps be achieved using a vector designed to integrate into chromosomes in the patient's targeted cells (for example, vectors patterned on retrovirus). Such a strategy, however, involves risks including (1) that the vector will integrate into an essential region of a chromosome, or (2) that the vector will integrate adjacent to an oncogene and activate it.

Accordingly, it would be desirable to provide for continued maintenance of gene therapy vectors (plasmids) in target cells by other means. One such strategy is to construct a plasmid capable of being maintained separately in the nucleus of a target cell, and that is also able to replicate there (i.e. an episome).

Plasmids provided according to this aspect of the invention can be constructed as follows. It has been determined (C. McWhinney et al., *Nucleic Acids Research*, 18, 1233–1242, 1990) that the 2.4 kb HindIII-XhoI fragment that is present immediately 5' to exon 1 of the human c-myc gene contains an origin of replication. The fragment was then cloned into a plasmid that if transfected into HeLa cells was shown to persist therein for more than 300 generations under drug selection. Replication was shown to be semi-conservative (C. McWhinney et al.). Although approximately 5% of the plasmid population was lost per cell generation without drug selection in those elements, this result nonetheless demonstrates substantial stabilization would be of benefit with respect to the design of therapeutic plasmids for gene therapy.

Accordingly, in one example of a replicating episomal vector, a variant of pCF1-CFTR (or pCF1-CAT) can be constructed in which a copy of the 2.4 kb HindIII-XhoI fragment is placed just 5' to the CMV enhancer/promoter region of the pCF1 backbone. Alternatively, between 2 and about 4—in tandem—copies of the 2.4 kb fragment may be similarly positioned. The increase in plasmid size that results from insertion of the 2.4 kb fragment (or multiple copies thereof) is predicted to provide an additional benefit, that is, to facilitate plasmid unwinding, thus facilitating the activity of DNA polymerase.

Use of this origin of replication, or multiple copies thereof, allows the resultant plasmid to replicate efficiently in human cells. Other DNA sequences containing other origins of replication may also be used (for example, as found in the human β-globin gene, or the mouse DHFR gene.

Figure 20:
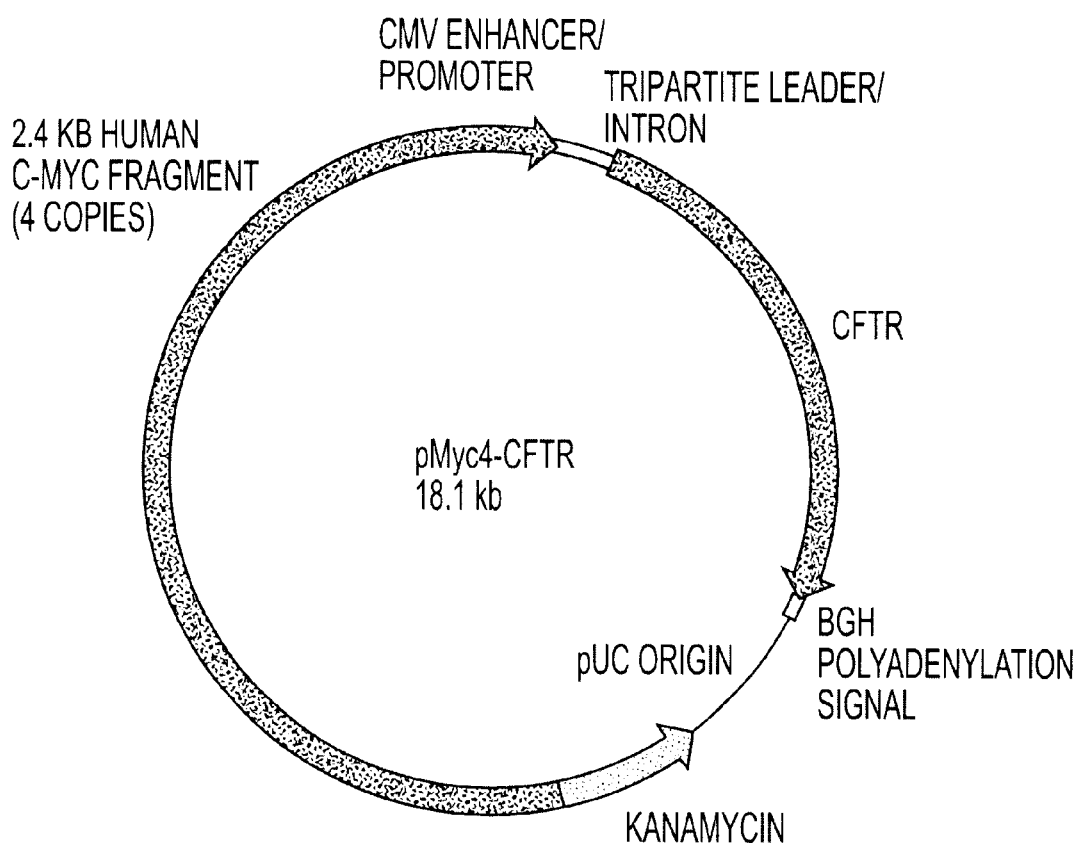
FIG. 20 provides a map of pMyc4-CFTR plasmid.

A plasmid that can be constructed according to this aspect of the invention and containing the cytomegalovirus promoter and enhancer, an intron, the CFTR cDNA, the bovine growth hormone polyadenylation signal, the kanamycin resistance transposon Tn903, and 4 copies of the 2.4 kb 5' flanking region of the human c-myc gene is shown in FIG. 20.

Example 8
Further Enhancements in Plasmid Design for Gene Therapy:
Use of Cytokine Promoters to Modulate Expression of Transgenes in Gene Therapy Chronic inflammation is associated with numerous of the disease states that can be treated by gene therapy. Representative of such disease states are cystic fibrosis (using CFTR), bronchitis, adult respiratory distress syndrome (using alpha-1 antitrypsin), and metastatic cancers (through up regulation of p53, TIMP-1, and TIMP-2). Inflammatory conditions typically involve many interrelated processes (for example, involvement by many types of immune system cells and liver proteins), whereby the body attempts to heal a damaged or infected tissue. However, chronic inflammation which persists as a result of an unresolved condition may lead to permanent tissue damage, as is the case with respect to lung tissue affected by cystic fibrosis and associated and unresolved lung infections. In fact, permanent damage to the lung tissue of cystic fibrosis patients is a leading cause of their mortality. It would be desirable to provide gene therapy in such a manner as to treat inflammatory conditions associated with the targeted disease state.

Accordingly, a further aspect of the present invention involves construction of gene therapy vectors in which the therapeutic transgene is placed under control of an RNA polymerase promoter from a cytokine gene (or a gene that encodes another simila regulatory protein) such as, for example, the promoter for any of interleukin 2, interleukin 8, interleukin 1, interleukin 11, interleukin 6, endothelin-1, monocyte chemoattractant protein-1, IL-1ra (receptor agonist), or for GM-CSF.

Cytokines may be defined as hormone-like intercellular signal proteins that are involved in regulation of cell proliferation, differentiation, and function, such as concerning haematopoiesis and lymphopoiesis. The interleukins are a particular group of cytokines having promoters that are useful in the practice of the invention. The interleukins are proteins, typically of unrelated origin, which act as intercellular signals mediating reactions between immunoreactive cells. However, it is understood that many "interleukins" have effects upon additional cell types including endothelial cells, epithelial cells, and fibroblasts.

Since the concentration of many cytokines is upregulated at an affected site in response to the level of inflammation that is present, gene therapy vectors can be designed wherein the level of therapeutic transgene expressed therefrom is determined, in part, by the level of inflammation present. There follows hereafter description of how such vectors are designed using primarily properties of the interleukin 8 gene as an example.

It has been determined that numerous biologically active molecules are present in tissues at concentrations thereof that increase with the severity of an inflammatory condition (for example, tumor necrosis factor "TNF" and potentially transcription factors such as NF-kB, AP-1, NF-IL6 and octamer binding protein). It has also been determined that interleukin 8, a polypeptide of 8,500 MW, is upregulated by inflammation and acts as a potent chemoattractant for T lymphocytes and neutrophil cells that are themselves involved in the inflammation response. The interleukin 8 gene is regulated primarily at the transcriptional level, and it has also been determined (H. Nakamura et al., *Journal of Biological Chemistry*, 266, 19611–19617, 1991) that TNF can increase interleukin 8 transcription by more than 30-fold in vitro in bronchial epithelial cells. Accordingly, there follows description of gene therapy vectors which take advantage of the above.

A plasmid can be constructed that is substantially similar to pCF1, that is, derived from a pUC plasmid containing a bacterial-derived origin of replication and a gene conferring resistance to kanamycin. The resultant plasmid contains also, in sequence, a CMV enhancer, a promoter, a hybrid intron, a cDNA sequence encoding CFTR, and the bovine growth hormone polyadenylation signal. As RNA polymerase promoter there is selected the −335 to +54 region of the interleukin 8 promoter. This region gave the highest ratio in terms of promoter activity plus TNF over minus TNF (Nakamura, 1991)

Such a plasmid has particularly valuable performance attributes. As inflammation increases in a cystic fibrosis-affected lung (and therefore the need to treat the lung with gene therapy also increases), the concentration of various inflammation-related molecules (such as TNF) will increase. By placing the CFTR-encoding cDNA of the therapeutic plasmid under the control of a transcriptional promoter (that of interleukin 8, for example) that is itself sensitive to the concentration of inflammation-related substances in contact with the cell, the promoter will function as a natural gene switch such that the amount of beneficial CFTR transcription will be tailored to the amount of inflammation. As aforementioned, RNA polymerase promoter sequences derived from the other aforementioned genes are also useful in the practice of the invention.

Example 9
Intravenous Delivery of Transgenes

For some disease states, such as cystic fibrosis, it is desirable to deliver transgenes to the lung. Delivery by aerosol is the most direct approach to achieve this goal. However, given the difficulties inherent with the delivery of an aerosol together with the potential need to target organs other than the lung (for example, the pancreas for cystic fibrosis), it is important to evaluate the feasibility of lung delivery using non-aerosol delivery formats. Accordingly, intravenous delivery of a reporter transgene was performed using a mouse model and the feasibility of intravenous organ targeting was assessed. A comparison was made of feasibility of delivery to the lung and the heart.

The reporter plasmid pCF-1CAT (Example 4) was used and was purified to minimize endotoxin (<1 EU/mg pDNA), and also chromosomal DNA contamination (<2%). Amphiphile No. 53 (1:1 with DOPE)/DNA complex was prepared according to the procedures of Example 3. The amphiphile was provided as the free base, the plasmid was prepared as a sodium salt in water, and the DOPE was provided in zwitterionic form.

The animal model was the BALB/c mouse. Females 6–8 weeks old weighing 16–18 g were injected intravenously using the tail vein, using 5 animals per group. The volume of lipid:pDNA complex used was 100 µl in all experiments. Unless noted otherwise, mice were sacrificed 48 h following administration of the complex. Organs were frozen immediately on dry ice to store for subsequent analysis.

Expression of chloramphenicol acetyl transferase (CAT) was quantitated using a radiochemical assay for CAT enzymatic activity. Organs Were weighed and homogenized on ice in a lysis buffer containing protease inhibitors. The lysate was freeze-thawed 3×, centrifuged, and heated to 65° C. to inactivate deacetylases before adding it to a reaction mixture containing $^{14}$C-chloraamphenicol. After an incubation at 37° C., the mixture was extracted with ethyl acetate, concentrated, spotted onto TLC plates and eluted with CHCl$_3$/MeOH. Spots corresponding to the acylated reaction products were quantitated (Betagen) and converted to ng CAT activity using authentic CAT standards.

Figure 21:
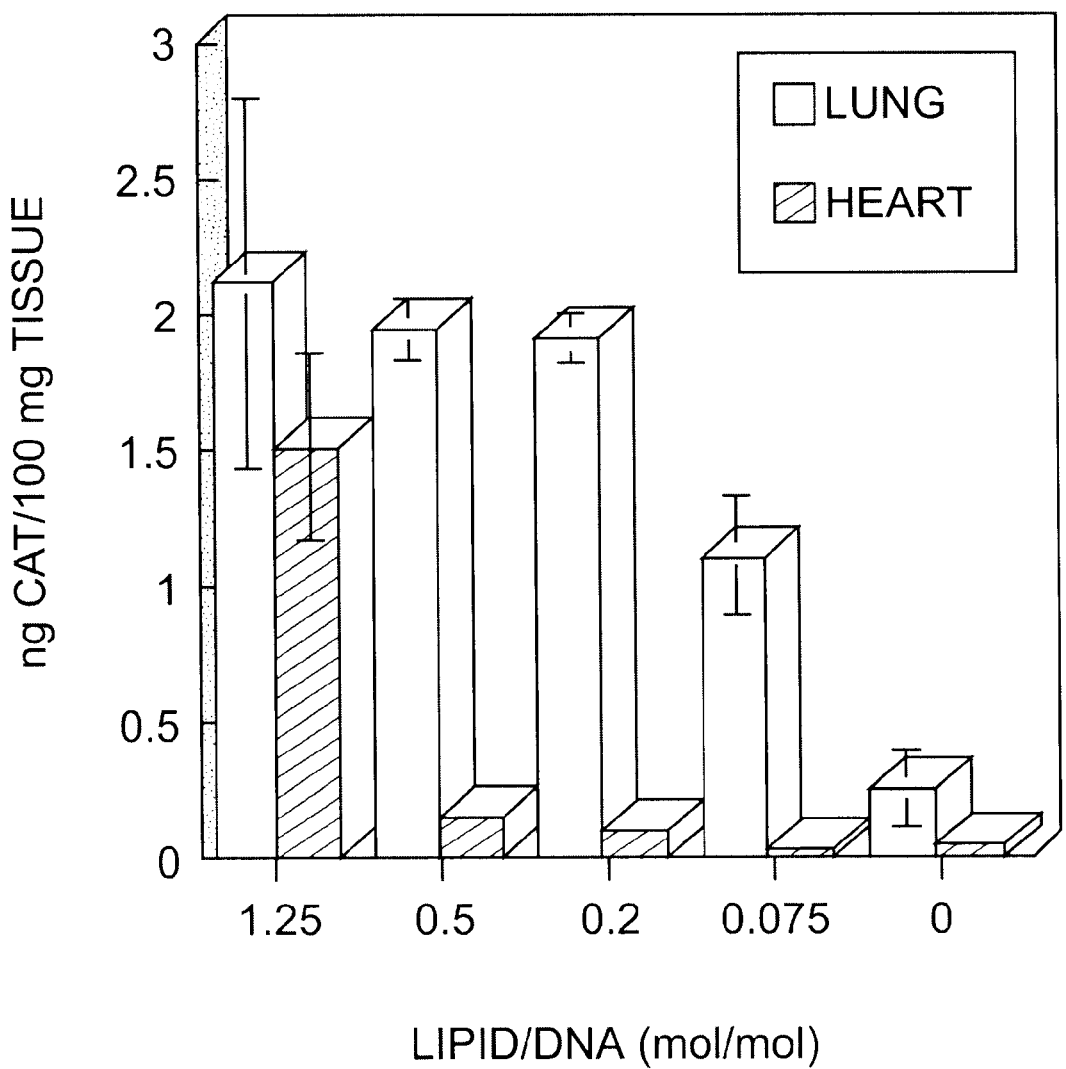
FIG. 21 demonstrates intravenous targeting of the heart and lung.

It was surprisingly determined that targeting to the heart could be substantially improved by altering the molar ratio (at a constant DNA concentration of 0.9 mM, measured as nucleotide) of amphiphile/DNA in the therapeutic composition. This information is of value in connection with gene therapy for the heart, such as for coronary disease. However, targeting to the lung remained relatively constant over a range of amphiphile/DNA ratios, all at constant DNA concentration (FIG. 21).

At molar ratios of less than about 0.5, the organ distribution was found to be strongly weighted toward the lung. At tis molar ratio, the zeta potential of the complex is negative (about −30 mV) due, in part, to excess negative charge from the DNA relative to the amphiphile. At an amphiphile/DNA ratio of 1.25, however, where the complex has a positive zeta potential (about +30 mV), organ distribution was remarkably altered and substantial expression was found in the heart (FIG. 21).

Zeta potentials of the samples can be measured (using typically 5 measurements per sample) employing a Malvem Zetasizer 4 (Malvern Instruments, Southborough, Mass.) and a zeta cell (AZ-104 cell, Malvern Instruments Co.).

Dried lipid films containing the cationic lipid and DOPE are hydrated in distilled water (dH$_2$O). DNA typically should be diluted to a concentration of about 300 µM in dH$_2$O. The DNA solution (1.5 mL) can then be added to an equal volume of cationic lipid vesicles and incubated at room temperature for 10 min. Enough NaCl (for example, 4 mM stock) may be added to result in a final concentration of 1 mM NaCl. If necessary, the sample can be diluted further with 1 mM NaCl (to maintain a photomultiplier signal below 4000 counts per second), and distilled water can be used in place of the NaCl solutions.

According to this aspect of the invention, amphiphiles No. 53 and No. 67 are among those preferred for use in intravenous targeting of the heart, as are many other amphiphiles selected from Groups I and II.

Example 10
Additional Experimental Procedures (A) Additional synthesis procedure for N$^4$-spermine cholesterol carbamate, amphiphile No 67
(Synthesis of N$^1$,N$^{12}$-diCbz-spermine di-HCl salt)

Benzylchloroformate (15 mL, 105 mmol) was dissolved in methylene chloride (335 mL) and placed in a tree neck flask under a nitrogen atmosphere. Imidazole (14 g, 206 mmol) was dissolved in methylene chloride (200 mL). The three neck flask was cooled to 0–2° C. using an ice-water bath and the imidazole solution was added gradually over 30 min. The cooling bath was removed and the mixture stirred at room temperature for 1 hour. Methylene chloride (250 mL) and aqueous citric acid (10%, 250 mL) were added to the mixture. The layers were separated and the organic layer was washed with aqueous citric acid (10%, 250 mL). The organic fraction was dried over magnesium sulfate and concentrated in vacuo. The resulting oil was vacuum dried for 2 hours at ambient temperature. To the oil was added dimethylaminopyridine (530 mg, 4.3 mmol) and methylene chloride (250 mL). The mixture was cooled to 0–2° C. and kept under a nitrogen atmosphere. A solution of spermine (10 g, 49 mmol) in methylene chloride (250 mL) was added gradually over 15 minutes, maintaining a reaction temperature of 0–2° C. The reaction mixture was stirred overnight at ambient temperature and then concentrated in vacuo. To the resulting material was added 1M hydrochloric acid (67 mL) and methanol (400 mL). The solution was cooled overnight at 4° C. yielding a white precipitate. The precipitate was isolated by vacuum filtration using Whatman #1 filter paper. The N$^1$,N$^{12}$-diCbz-spermine di HCl salt (13.38 g, 24.7 mmol, 50% yield) thus obtained was dried under vacuum at ambient temperature for 17 hours.

(Synthesis of N$^1$,N$^{12}$-diCbz-N$^4$-spermine cholesteryl carbamate) N$^1$,N$^{12}$-diCbz-spermine di HCl salt (13.38 g, 24.7 mmol) was dissolved in a chloroform, methanol and water mixture in the ratio 65:25:4 (940 mL). The solution was stirred at room temperature and cholesteryl chloroformate (11 g, 24.5 mmol) was added. The solution was stirred at ambient temperature for 1.5 hours and then diluted with 1M sodium hydroxide solution (165 mL). The organic and aqueous layers were separated and the organic layer containing the product was washed with water (110 mL). The organic fraction was dried over sodium sulfate, concentrated in vacuo and vacuum dried. The crude oil was purified by chromatography using silica gel (60Å, 1 Kg). The silica was packed in 10% MeOH/CHCl$_3$ and the column was eluted with 25% MeOH/CHCl$_3$. Fractions of 900 mL were collected and analyzed by thin layer chromatography. Fractions containing the product (Rf.=0.5 in 20% MeOH/CHCl$_3$) were combined and concentrated in vacuo. The resulting oil was dried under vacuum for 17 hours to give 8.5 g (9.67 mmol, 39% yield) of product.

(Synthesis of $N^4$-spermine cholesteryl carbamate)

$N^1,N^{12}$-diCbz-$N^4$-spermine cholesteryl carbamate (8.5 g, 9.67 mmol) was dissolved in 200 mL of acetic acid and 1.66 g of 10% Pd on carbon was added. The solution was purged with nitrogen and stirred under hydrogen at atmospheric pressure. The hydrogen was supplied to the reaction flask using a balloon filled with hydrogen gas. The hydrogenolysis was allowed to proceed for 3 hours. The reaction mixture was filtered through Whatman #1 filter paper and the catalyst was washed with 250 mL of 10% acetic acid in ethyl acetate. The filtrate was concentrated in vacuo to give a residue, coevaporation with chloroform aids removal of the acetic acid. To the crude product was added 1M sodium hydroxide solution (400 mL) and the solution was extracted three times with 10% MeOH/CHCl$_3$ (700 mL). The combined organic fractions were washed with water (600 mL) and dried over sodium sulfate. The solution was filtered, concentrated in vacuo and vacuum dried at ambient temperature for 48 hours. The crude material was purified by chromatography on silica gel (500 g). The column was packed in 40:25 MeOH: CHCl$_3$ and eluted with 40:25 MeOH: CHCl$_3$ and then 40:25:10 MeOH: CHCl$_3$: NH$_4$OH. The fractions collected were analyzed by thin layer chromatography and the product containing fractions were combined and concentrated in vacuo (the evaporation was assisted by the addition of iso-propanol in order to azeotrope the residual water). The material was vacuum dried at ambient temperature for 48 hours to give $N^4$-spermine cholesteryl carbamate (4 g, 6.5 mmol, 67% yield).

(B) $N^4$-(N'-cholesteryl carbamate glycineamide (amphiphile No. 91)

N-t-BOC-glycine-N-hydroxysuccinimide ester (0.5 g, 1.83 mmol) was added to a solution of diCbz-spermine•2HCl (1.0 g, 1.94 mmol) and N,N-diisopropylethylamine (0.3 mL, 1.72 mmol) in 65/25/4 chloroform/methanol/water (50 mL). The solution was stirred overnight at room temperature. Analysis of the reaction by TLC (20% methanol/chloroform) indicated the presence of a new spot. The reaction was washed first with 1M NaOH (10 mL) then with H$_2$O (10 mL). The organic layer was separated, dried over sodium sulfate, vacuum filtered, and reduced in vacuo to an oil. The crude material was purified by flash column chromatography (85 g silica gel) eluting with 20% methanol/chloroform. The desired product was isolated and characterized by $^1$H NMR as $N^1,N^{12}$-diCbz-$N^4$-(N'-t-BOC-glycineamide)-spermine (402 mg, 0.65 mmol, 35%).

Benzyl chloroformate (100 mg, 0.58 mmol) was added to a solution of $N^1,N^{12}$-diCbz-$N^4$-(N'-t-BOC-glycineamide)-spermine (220 mg, 0.354 mmol) and triethylamine (4 drops) in methylene chloride (20 mL). The reaction was stirred overnight at room temperature. Analysis of the reaction by TLC (20% methanol/chloroform) indicated the presence of a new, higher running spot. The reaction was quenched by the addition of 1M HCl (5 mL). The organic layer was isolated, washed with H$_2$O (5 mL), dried over sodium sulfate, filtered, and reduced in vacuo.

The resulting crude material was dissolved in chloroform (30 mL) and anhydrous HCl gas was bubbled through the solution for 2 hours. Analysis of the reaction by TLC (10% methanol/chloroform) indicated the complete disappearance of the staring material. The reaction was purged with dry nitrogen, and washed with 1M NaOH (2×10 mL) and dH2O (10 mL). The organic layer was isolated, dried over sodium sulfate, filtered, and reduced in vacuo to give $N^1,N^9,N^{12}$-triCbz-$N^4$-glycineamide-spermine (219 mg, 0.33 mmol, 93% yield for two steps).

Cholesteryl chloroformate (148 mg, 0.33 mmol) was added to a solution of $N^1,N^9,N^{12}$-triCbz-$N^4$-glycineamide-spermine (219 mg, 0.33 mmol) and triethylamine (0.3 mL, 2.15 mmol) in methylene chloride (30 mL). The reaction was stirred at room temperature for 3 hours. The reaction was washed with H$_2$O (10 mL). The organic layer was separated, dried over sodium sulfate, filtered, and reduced in vacuo. The crude material was purified by flash column chromatography (30 g silica gel) eluting with 65% ethyl acetate/hexanes. The desired product was isolated and characterized by $^1$H NMR as $N^1,N^9,N^{12}$-triCbz-$N^4$-(N'-cholesteryl carbamate glycineamide)-spermine (221 mg, 0.2 mmol, 62% yield).

$N^1,N^9,N^{12}$-tri-Cbz-$N^4$-(N'-cholestryl carbamate glycineamide)-spermine (221 mg, 0.2 mmol) was stirred with 10% Pd/C (50 mg) in glacial acetic acid (10 mL) under a hydrogen atmosphere for 2.5 hours. Analysis of the reaction by TLC (65% ethyl acetate/hexanes) indicated the complete disappearance of the starting material. The flask was purged with nitrogen and the catalyst was removed by vacuum filtration through filter paper rinsing with 10% acetic acid ethyl acetate (20 mL). The filtrate was reduced in vacuo to an oil which was dissolved in 10% methanol/chloroform (100 mL) and washed with 1M NaOH (20 mL) and H$_2$O (15 mL). The organic layer was separated, dried over sodium sulfate, filtered, and reduced in vacuo. The isolated product was characterized by $^1$H NMR as $N^4$-(N'-cholesteryl carbamate glycineamide)-spermine (128 mg, 0.19 mmol, 95% yield).

(C) Sythesis of $N^4$-spermidine-2,3-dilauryloxypropylamine, amphiphile No. 94.

2,3 Dimyristoylglycerol (600 mg, 1.4 mmol) was dissolved in pyridine and the solution cooled to 0° C. The solution was stirred under a nitrogen atmosphere and p-toluenesulfonyl chloride (300 mg, 1.57 mmol) was added. The solution was allowed to warm to room temperature and was then stirred overnight at ambient temperature. To the solution was added hydrochloric acid (2.5M, 20 mL) and the solution was extracted three times with methylene chloride (25 mL). The combined organic extracts were dried over sodium sulfate, filtered and concentrated in vacuo to give a crude oil. The oil was purified by flash chromatography (50 g of silica gel, 60 Å) eluting with 5% ethyl acetate/hexane. The oil obtained by flash chromatography was dried under high vacuum at ambient temperature to give 2,3-Dimyristoylglycerol-tosylate 630 mg, 77% yield).

2,3-Dimyristoylglycerol-tosylate (300 mg, 0.51 mmol) and $N^1,N^8$-diCbz-spermidine (1.5 g, 3.6 mmol) were dissolved in toluene (15 mL). The solution was stirred under a nitrogen atmosphere and heated at reflux (110° C.). The reaction was heated for 5 days at reflux temperature. The reaction was cooled to room temperature and then filtered through Whatman #1 filter paper. The filtrate was concentrated in vacuo. The residue was dissolved in chloroform (50 mL) and washed with sodium hydroxide solution (1 M, 10 mL) and water (10 mL). The organic fraction was dried over sodium sulfate, filtered and concentrated in vacuo. The crude material was purified by flash chromatography (30 g silica gel, 60Å) eluting with 5% methanol/chloroform. The product containing fractions were concentrated in vacuo. The material was purified by a second flash chromatography column (20 g silica, 60Å) eluting with 50% ethyl acetate/hexane. Chromatography gave, after drying the product under high vacuum at ambient temperature, $N^4$-($N^1,N^8$)-diCbz-spermidine2,3-dilauryloxypropylamine, as an oil (142 mg, 35% yield).

$N^4$-($N^1,N^8$-diCz-spermidine-2,3-dilauryloxypropylamine (142 mg, 0.18 mmol) in glacial acetic acid (5 mL) was stirred with 10% Pd/C (50 mg) under a hydrogen atmosphere, for 2 hours. The catalyst was removed by vacuum filtration through Whatman #1 filter paper. The catalyst was washed with ethyl/acetate hexane (10%, 10 mL). The filtrate was concentrated in vacuo and dried for 2 hours under high vacuum. To the residue was added sodium hydroxide solution (1 M, 8 mL) and the solution was extracted three times with methanol/chloroform (10%, 20 mL). The combined organic extracts were dried over sodium sulfate, filtered and concentrated in vacuo to give after drying under high vacuum $N^4$-spermidine-2,3-dilauryloxypropylamine (52 mg, 52% yield).

(D) Synthesis of $N^4$-spermine-2,3-dilauryloxypropylamine, amphiphile No. 102

$N^1,N^{12}$-diCbz-spermine (0.87 g, 1.85 mmol) and 2,3-dyristoylglycerol-tosylate (280mg, 0.48 mmol) were dissolved in toluene (25 mL) and heated at reflux temperature (110° C.) for 3 days. The solution was concentrated in vacuo and the resulting material was purified by flash chromatography (30 g silica gel, 60 Å) eluting with 10% methanol/chloroform. The material isolated was dissolved in methanol/chloroform (10%, 85 mL) and washed twice with sodium hydroxide solution (1 M, 15 mL) and water (10 mL). The organic fraction was dried over sodium sulfate, filtered and concentrated in vacuo. The material was dried under high vacuum overnight, at ambient temperature, to yield $N^4$-($N^1,N^{12}$-diCbz-spermine)-2,3-dilauryloxypropylamine 180 mg, 43% yield).

$N^4$-($N^1,N^{12}$-diCbz-spermine)-2,3-dilauryloxypropyle (180 mg, 0.2 mmol) in glacial acetic acid (10 mL) was stirred with 10% Pd/C (50 mg) under a hydrogen atmosphere, for 3 hours. The catalyst was removed by vacuum filtration through Whatman #1 filter paper. The catalyst was washed with ethyl/acetate hexane (10%, 30 mL). The filtrate was concentrated in vacuo and dried for 2 hours under high vacuum. To the residue was added methanol/chloroform (10%, 85 mL) and the organic layer was washed twice with sodium hydroxide solution (1 M, 15 mL) and water (10 mL). The organic fraction was dried over sodium sulfate, filtered and concentrated in vacuo to give after drying under high vacuum $N^4$-spermine-2,3-dilauryloxypropylamine (50 mg, 40% yield).

The above descriptions of preferred embodiments of the invention have been presented to illustrate the invention to those skilled in the art. They are not intended to limit the invention to the precise forms disclosed.

What is claimed is:

1. An aerosolized solution comprising:
   (1) at least one cationic amphiphile effective for facilitating transport of a biologically active molecule into a cell;
   (2) at least one biologically active molecule; and
   (3) at least one fatty acid species of PEG-PE
   wherein said at least one biologically active molecule comprises at least one nucleic acid and wherein said cationic amphiphile and said biologically active molecule interact through ionic charge.

2. The aerosolized solution according to claim 1 further comprising at least one co-lipid.

3. The aerosolized solution according to claim 2 wherein said co-lipid is at least one of phosphatidyl-ethanolamines, phosphatidylcholines, lyso-phosphatidylcholines, and cholesterol.

4. The aerosolized solution according to claim 2 wherein said co-lipid is phosphatidyl-ethanolamine co-lipid selected from DOPE, diphytanoyl phosphatidyl-ethanolamines, and lyso-phosphatidyl ethanolamines.

5. The aerosolized solution according to claim 2 comprising a 1:2:0.05 molar mixture of the cationic amphiphile $N^4$-spermine cholesteryl carbamate, the co-lipid DOPE, and the fatty acid species of PEG-PE, $PEG_{(5000)}$-DMPE.

6. The aerosolized solution according to claim 1 wherein the cationic amphiphile effective for facilitating transport of said biologically active molecule into a cell is at least one of $N^4$-spermidine cholesteryl carbamate, $N^4$-spermine cholesteryl carbamate, $N^4$-($N'$-cholesteryl carbamate serineamide)-spermidine,

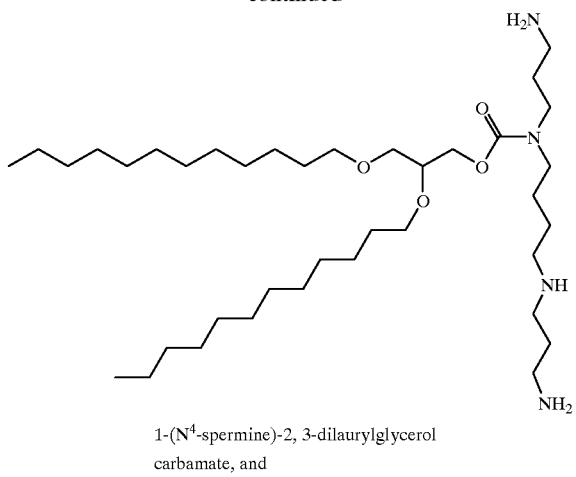

-continued 1-($N^4$-spermine)-2, 3-dilaurylglycerol carbamate, and

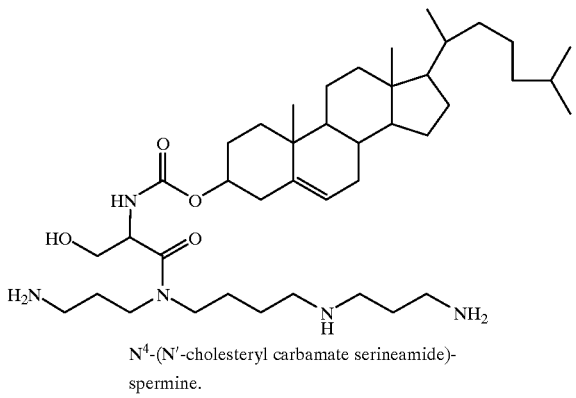

$N^4$-(N′-cholesteryl carbamate serineamide)-spermine.

7. The aerosolized solution according to claim 1 wherein said fatty acid species of PEG-PE is at least one of PEG $_{(5000)}$-PE, PEG$_{(5000)}$-DMPE, PEG$_{(2000)}$-PE, and PEG$_{(2000)}$-DMPE.

8. The aerosolized solution according to claim 1 wherein said biologically active molecule is a genetically expressible polynucleotide present at a concentration ranging from about 2 mM to about 12 mM.

9. A method of delivering a biologically active molecule to a cell of a mammal comprising: administering an aerosolized solution to said mammal wherein said aerosolized solution comprises:

(1) at least one cationic anphiphile effective for facilitating transport of a biologically active molecule into said cell;

(2) at least one biologically active molecule; and (3) at least one fatty acid species of PEG-PE wherein said at least one biologially active molecule comprises at least one nucleic acid and wherein said cationic amphiphile and said biologically active molecule interact through ionic charge.

10. The method of delivering a biologically active molecule to a cell of a mammal according to claim 9, wherein said solution further comprises at least one co-lipid.

11. The method of delivering a biologically active molecule to a cell of a mammal according to claim 10 wherein said co-lipid is at least one of phosphatidyl-ethanolamines, phosphatidylcholines, lyso-phosphatidylcholines, and cholesterol.

12. The method of delivering a biologically active molecule to a cell of a mammal according to claim 10 wherein said co-lipid is phosphatidyl-ethanolamine co-lipid selected from DOPE, diphytanoyl phosphatidyl-ethanolamines, and lyso-phosphatidyl ethanolamines.

13. The method of delivering a biologically active molecule to a cell of a mammal according to claim 10 wherein said solution comprises a 1:2:0.05 molar mixture of the cationic amphiphile $N^4$-spermine cholesteryl carbamate, the co-lipid DOPE, and the fatty acid species of PEG-PE, PEG$_{(5000)}$-DMPE.

14. The method of delivering a biologically active molecule to a cell of a mammal according to claim 9 wherein the cationic amphiphile effective for facilitating transport of said biologically active molecule into a cell is at least one of $N^4$-spermidine cholesteryl carbamate, $N^4$-spermine cholesteryl carbamate,

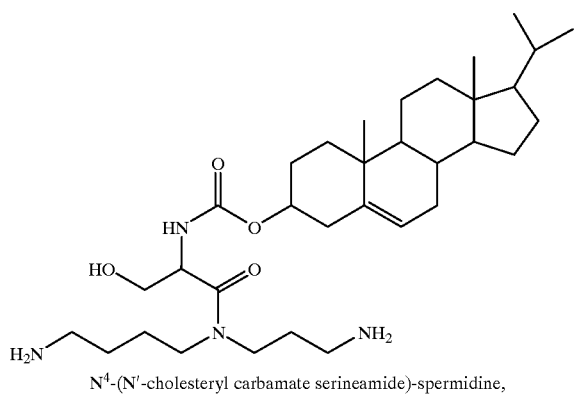

N⁴-(N'-cholesteryl carbamate serineamide)-spermidine,

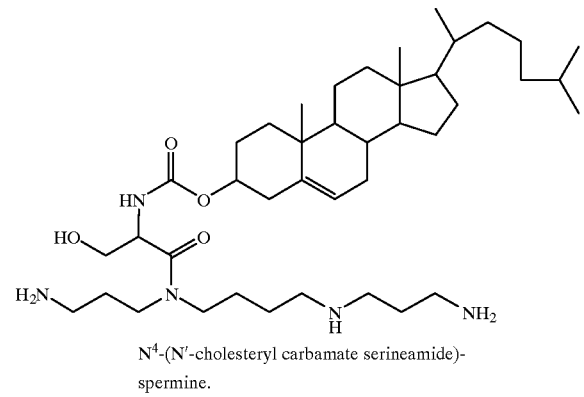

N⁴-(N'-cholesteryl carbamate serineamide)-spermine.

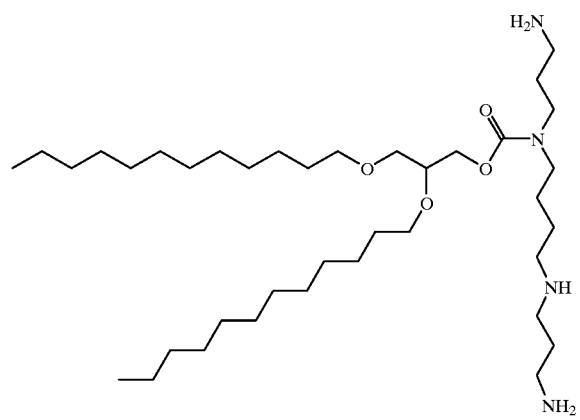

1-(N⁴-spermine)-2,3-dilaurylglycerol carbamate, and

15. The method of delivering a biologically active molecule to a cell of a mammal according to claim 9 wherein said fatty acid species of PEG-PE is at least one of PEG$_{(5000)}$-PE, PEG$_{(5000)}$-DMPE, PEG$_{(2000)}$-PE, and PEG$_{(2000)}$-DMPE.

16. The method of delivering a biologically active molecule to a cell of a mammal according to claim 9 wherein said biologically active molecule is a genetically expressible polynucleotide present at a concentration ranging from about 2 mM to about 12 mM.

\* \* \* \* \*